(12) United States Patent
Sanford et al.

(10) Patent No.: US 8,779,089 B2
(45) Date of Patent: Jul. 15, 2014

(54) METHODS AND COMPOSITIONS FOR SOFT TISSUE REPAIR

(75) Inventors: Isaac Gilliam Sanford, Durham, NC (US); Michelle Steffen Jansen, Durham, NC (US); Paul Theodore Hamilton, Cary, NC (US); Jonathan Allen Hodges, Durham, NC (US); Shrikumar Ambujakshan Nair, Cary, NC (US); Yuchen Chen, Chapel Hill, NC (US); Martyn Kerry Darby, Chapel Hill, NC (US); Hanne Gron, Durham, NC (US); Ganesan Sathya, Cary, NC (US)

(73) Assignee: Affinergy, LLC, Durham, NC (US)

( * ) Notice: Subject to any disclaimer, the term of this patent is extended or adjusted under 35 U.S.C. 154(b) by 478 days.

(21) Appl. No.: 12/949,104

(22) Filed: Nov. 18, 2010

(65) Prior Publication Data
US 2011/0117167 A1      May 19, 2011

Related U.S. Application Data

(60) Provisional application No. 61/262,353, filed on Nov. 18, 2009, provisional application No. 61/368,849, filed on Jul. 29, 2010, provisional application No. 61/370,723, filed on Aug. 4, 2010.

(51) Int. Cl.
| | |
|---|---|
| *A61K 38/10* | (2006.01) |
| *C07K 17/00* | (2006.01) |
| *C07K 17/12* | (2006.01) |
| *C07K 7/08* | (2006.01) |
| *C07K 17/08* | (2006.01) |
| *C07K 17/10* | (2006.01) |
| *A61K 47/48* | (2006.01) |
| *A61K 47/02* | (2006.01) |
| *A61K 9/00* | (2006.01) |
| *A61L 27/54* | (2006.01) |
| *A61L 27/58* | (2006.01) |
| *A61K 47/42* | (2006.01) |
| *A61L 27/42* | (2006.01) |

(52) U.S. Cl.
CPC ..... *A61K 47/48992* (2013.01); *A61K 47/48246* (2013.01); *A61K 47/02* (2013.01); *A61K 9/0024* (2013.01); *A61K 38/10* (2013.01); *A61L 27/54* (2013.01); *A61L 27/58* (2013.01); *A61K 47/42* (2013.01); *A61L 27/427* (2013.01); *A61L 27/425* (2013.01); *A61L 2430/02* (2013.01); *A61L 2300/414* (2013.01)
USPC .......................... 530/326; 514/21.3; 424/423

(58) Field of Classification Search
None
See application file for complete search history.

(56) References Cited

U.S. PATENT DOCUMENTS

| | | |
|---|---|---|
| 4,987,085 A | 1/1991 | Allen et al. |
| 6,284,503 B1 | 9/2001 | Caldwell et al. |
| 2004/0043450 A1 | 3/2004 | Farach-Carson et al. |
| 2006/0115515 A1 | 6/2006 | Pirhonen et al. |
| 2006/0286066 A1 | 12/2006 | Basran |
| 2008/0033572 A1 | 2/2008 | D'Antonio et al. |
| 2008/0176247 A1 | 7/2008 | Chou et al. |
| 2009/0098175 A1 | 4/2009 | Buehrer et al. |
| 2009/0098177 A1 | 4/2009 | Werkmeister et al. |
| 2009/0215640 A1 | 8/2009 | West et al. |

FOREIGN PATENT DOCUMENTS

| | | |
|---|---|---|
| WO | 2004035732 A2 | 4/2004 |
| WO | WO/2007/089084 | 8/2007 |

OTHER PUBLICATIONS

Restriction Requirement dated Aug. 24, 2012 for related U.S. Appl. No. 13/109,802, filed May 17, 2011, status pending.
Applicant's Response dated Sep. 24, 2012 to Restriction Requirement for related U.S. Appl. No. 13/109,802, filed May 17, 2011.
Restriction Requirement dated Dec. 15, 2011 for related U.S. Appl. No. 12/949,767, filed Nov. 18, 2010.
Applicant's Response dated Feb. 14, 2012 to Restriction Requirement dated Dec. 15, 2011 for related U.S. Appl. No. 12/949,767, filed Nov. 18, 2010.
Non-Final Office Action dated Apr. 17, 2012 for related U.S. Appl. No. 12/949,767, filed Nov. 18, 2010.
Response dated Jul. 16, 2012 to Non-final Office Action for related U.S. Appl. No. 12/949,767, filed Nov. 18, 2010.
Apr. 25, 2011, ISR and WO for PCT Appn. No. PCTUS1057283.
Apr. 22, 2011, ISR and WO for PCT Appn. No. PCTUS1057304.
Jun. 10, 2011, ISR and WO for PCT Appn. No. PCTUS1057266.
Altman, et al (2010). "Adipose tissue-derived stem cells enhance bioprosthetic mesh repair of ventral hernias." Plast Reconstr Surg 126(3): 845-54.
Cherubino et al (2011). "Adipose-derived stem cells for wound healing applications." Ann Plast Surg 66(2): 210-5.
Cunningham et al (2009). "Ceramic granules enhanced with B2A peptide for lumbar interbody spine fusion." J Neurosurg Spine 10(4): 300-7.
Garcia-Olmo et al (2009). "Expanded adipose-derived stem cells for the treatment of complex perianal fistula: a phase II clinical trial." Dis Colon Rectum 52(1): 79-86.
Hanson et al (2010). "Mesenchymal stem cell therapy for nonhealing cutaneous wounds." Plast Reconstr Surg 125(2): 510-6.

(Continued)

*Primary Examiner* — Karlheinz R Skowronek
*Assistant Examiner* — Lianko Garyu
(74) *Attorney, Agent, or Firm* — NK Patent Law, PLLC

(57) ABSTRACT

Compositions and methods for tissue repair are provided including cell binding peptides and growth factor binding peptides. The cell binding peptides bind to one or more of stem cells, fibroblasts, or endothelial cells. The growth factor binding peptides include platelet derived growth factor (PDGF) binding peptides and growth differentiation factor (GDF) binding peptides. The tissue for repair includes tendon, muscle, connective tissue, ligament, cardiac tissue, vascular tissue, or dermis. Implantable devices for tissue repair are provided to which the cell and growth factor binding peptides are attached, such as acellular extracellular matrix having attached binding peptide.

24 Claims, 33 Drawing Sheets

(56) References Cited

OTHER PUBLICATIONS

Hersel et al. (2003). "RGD modified polymers: biomaterials for stimulated cell adhesion and beyond." Biomaterials 24(24): 4385-415.
Price et al. (2004). "The role of allogenic fibroblasts in an acute wound healing model." Plast Reconstr Surg 113(6): 1719-29.
Pu et al (2010). "The use of flow perfusion culture and subcutaneous implantation with fibroblast-seeded PLLA-collagen 3D scaffolds." Biomaterials 31(15): 4330-40.
Trombelli & Farina (2008). "Clinical outcomes with bioactive agents alone or in combination." J Clin Periodontol 35(8 Suppl): 117-35.
Franz et al., 2001, "Transforming Growth Factor beta2 lowers the incidence of incisional hernias." J. Surgical Res., 97:109-16.
Franz, M.G., "The biology of hernia fomation" Surg Clin North Am, 2008, 88:1-15, vii.
Non-Final Office Action dated Nov. 26, 2012, for related U.S. Appl. No. 13/109,802, filed May 17, 2011 and references included therein.
Applicant's Response filed May 23, 2013, to Non-final Office Action dated Nov. 26, 2012, for related U.S. Appl. No. 13/109,802, filed May 17, 2011.
Rudinger, J. In: Peptide Hormones, JA Parson, Ed. (1976) 1-7 (not provided with Office Action).
Sigma, Designing Custom Peptides. http://www.sigma-genosys.com/peptide_design.asp (Accessed Dec. 16, 2004, 2 pages).
Berendsen, HJC, A Glimpse of the Holy Grail?, Science (1998) 282, pp. 642-643.
Voet and Voet, Biochemistry, 2nd Edition (1995) pp. 235-241.
Smilek, DE et al., Proc. Natl. Acad. Sci USA (1991) 88, pp. 9633-9637.
Messer, WS, "Vasopressin and Oxytocin" web document updated Apr. 3, 2000, http://www.neurosci.pharm.utoledo.edu/MBC3320/vasopressin.htm; 5 pages.

Figure 14

| | | | | | | | | | | | | | | | |
|---|---|---|---|---|---|---|---|---|---|---|---|---|---|---|---|
| SEQ ID NO: 1 | | | M | Y | F | S | P | L | H | T | W | Q | S | A | P | S | T | S | G |
| SEQ ID NO: 2 | | | F | R | F | Q | R | L | E | D | W | N | Y | P | S | N | T | D | N |
| SEQ ID NO: 5 | V | A | N | P | F | T | Y | L | S | A | W | S | N | P | L | - | - | - | - |
| SEQ ID NO: 6 | E | T | L | I | F | S | K | L | G | Q | W | G | N | S | L | - | - | - | - |
| SEQ ID NO: 7 | G | Y | M | Q | F | G | H | L | L | D | W | T | G | S | P | - | - | - | - |
| SEQ ID NO: 8 | S | V | Y | R | F | D | S | L | T | T | W | S | S | N | Q | - | - | - | - |
| SEQ ID NO: 9 | G | S | W | S | F | G | T | L | G | P | W | S | S | S | Q | - | - | - | - |
| SEQ ID NO: 10 | W | L | G | N | F | N | A | L | T | D | W | P | T | D | S | - | - | - | - |
| SEQ ID NO: 11 | T | S | G | F | F | G | S | L | D | T | W | P | P | T | L | - | - | - | - |
| SEQ ID NO: 12 | N | Y | W | N | F | G | P | L | E | D | Y | S | - | - | - | - | - | - | - |
| SEQ ID NO: 13 | S | V | L | H | F | H | P | M | K | S | Y | D | - | - | - | - | - | - | - |
| SEQ ID NO: 14 | N | S | I | Y | F | S | P | L | R | D | Y | Q | - | - | - | - | - | - | - |
| SEQ ID NO: 15 | G | H | F | E | Y | G | R | L | Q | S | I | L | - | - | - | - | - | - | - |
| Consensus | | | | | F | | | L | | | W | | | | | | | | |

A.

B.

C.

A.

B.

METHODS AND COMPOSITIONS FOR SOFT TISSUE REPAIR

CROSS-REFERENCE TO RELATED APPLICATIONS

This application claims the benefit of U.S. Provisional Application No. 61/262,353, filed Nov. 18, 2009; U.S. Provisional Application No. 61/368,849, filed Jul. 29, 2010; and U.S. Provisional Application No. 61/370,723, filed Aug. 4, 2010, each of which is hereby incorporated in its entirety by reference herein. In addition, this application is related to co-pending U.S. application Ser. No. 12/949,767, filed Nov. 18, 2010 and co-pending U.S. application Ser. No. 13/109,802, filed May 17, 2011, and is related to International Application No. PCT/US10/57283, filed Nov. 18, 2010; International Application No. PCT/US10/57304, filed Nov. 18, 2010; and International Application No. PCT/US10/57266, filed Nov. 18, 2010.

GRANT STATEMENT

The invention was made with government support under Grant No. 1R43GM083380-01, under Grant No. 1R43AR054229-01, under Grant No. R43GM087751-01, under Grant No. R44AR053753-02A1, under Grant No. R43HL087501-02, and under Grant No. R43HL091590-01A1, each awarded by the National Institute of Health. The government has certain rights in the invention.

FIELD

The presently disclosed subject matter relates to the capture of cells and growth factors onto implantable devices for tissue repair.

BACKGROUND

Multipotent stem cells are known to play a role in healing and repair in response to trauma, disease or disorder. Stem cell mediated repair and healing are achieved by proliferation and differentiation of the stem cells into specialized cell types. For example, mesenchymal stem cells can differentiate into cell types such as bone, cartilage, fat, ligament, muscle, and tendon. In the case of defects in bone, mesenchymal stem cells from the bone marrow, periosteum, and surrounding soft tissue proliferate and differentiate into specialized bone cells. Stem cells can be obtained from embryonic or adult tissues of humans or other animals. As a result of the healing activity of stem cells, much focus has been placed on using stem cells as a treatment to aid in the remodeling of damaged tissue into healthy tissue.

In addition to stem cells, certain growth factors have shown clinical benefit in treatment of bone defects, injuries, disorders, or diseases. Growth and differentiation factors (GDFs) are members of the family of growth factors belonging to the family of bone morphogenetic proteins (BMPs). GDF-5, GDF-6, and GDF-7 (also known as BMP-14, BMP-13, and BMP-12, respectively) are involved in fibrous connective tissue development and healing, as GDFs stimulate production of fibrous connective tissue in vitro and in vivo. However, use of exogenous GDF to aid in tissue repair has been associated with ectopic differentiation of joints, tendon, cartilage, and bone.

Platelet derived growth factor-BB (PDGF-BB) is known to be involved in wound healing (Pierce et al., 1992, Am. J. Pathol., 140:1375-88) and a product containing PDGF-BB has been approved by the FDA for wound healing indications. The data support the safety and benefits of PDGF-BB in healing diabetic ulcers (Smiell et al., 1999, Wound Rep. Reg., 7:335-46). However, PDGF-BB therapy requires repeated applications to achieve clinical efficacy, and PDGF is a potent initiator of fibroblast proliferation which has been linked to tumor growth (Alvarez et al., 2006, Mayo Clin. Proc., 81:1241-57).

In addition to stem cells, fibroblast cells have a role in soft tissue repair. Hernia repair is one of the most common surgical procedures world-wide, with over 20 million repairs performed each year (Kingsnorth, A. and K. LeBlanc, Lancet, 2003, 362:1561-71). In the US there are approximately 100,000 incisional hernia repairs performed annually costing an estimated 1.7 billion dollars (Finan et al., Hernia, 2009, 13:173-82). Despite advances, recurrence rates remain high and range from 3-60% with an average rate of 25% for an initial repair and 44% after a second repair (Afifi, R. Y., Hernia, 2005, 9:310-5; Gray et al., Am J Surg, 2008, 196:201-6). Biocompatible materials have triggered a rapid evolution of hernia repair techniques over the past 10 years. High-tension fascial suturing to strengthen the abdominal wall has been replaced by low-tension repair using biocompatible synthetic mesh (Luijendijk et al., N Engl J Med, 2000, 343:392-98; Flum et al., Ann Surg, 2003, 237:129-35). While a modest improvement over basic suturing, synthetic mesh harbors all the potential pitfalls of implanting a permanent foreign body: adhesions, potential infection, chronic pain, and subsequent mesh removal (Flum et al., Ann Surg, 2003, 237:129-35; Conze et al., Langenbecks Arch Surg, 2007. 392:453-37). Allograft and xenograft materials such as, for example, acellular dermal matrix (ADM) and porcine small intestine submucosa have emerged as favorable alternatives to synthetics, especially in patients with comorbidities, for many types of soft tissue repair including wound, abdominal wall, tendon, breast, dura matter, and rotator cuff repair (Diaz et al., Am Surg, 2006, 72:1181-88; Kim et al., Am J Surg, 2006, 192:705-9; Kish et al., Am Surg, 2005, 71:1047-50; Butler, C. E., Clin Plastic Surg, 2006, 33:199-211; Badylak, S. F., Biomaterials, 2007, 28:3587-93; Longo et al., British Medical Bulletin, 2010, 94:165-88), maintaining an intact elastin lattice, as well as channels for capillary microvascularization. These collagen-based materials promote key components of wound healing and are bioabsorbable. However, complication rates of 24% with recurrence being the most common complication have been reported with these materials, and design improvements are needed (Gupta, A., et al., Hernia, 2006, 10:419-25; Misra, S., et al., Hernia, 2008, 12:247-50). Wound breaking strength represents the amount of force a surgical wound can withstand before failing, and failure occurs when there is a deficient quantity and quality of tissue repair (Franz, M. G., Surg Clin North Am, 2008, 88:1-15, vii). Previous studies have suggested that wound repair integrity reaches a normal breaking strength in 30 days (Franz et al., J Surg Res, 2001, 97: 109-16; Robson, M. C., Surg Clin North Am, 2003, 83:557-69). Fibroblasts are responsible for collagen synthesis and deposition and recovery of wound breaking strength (Franz, M. G., Surg Clin North Am, 2008, 88:1-15, vii). Two days post surgery the inflammatory response subsides and fibroblasts infiltrate the wound, out numbering other cell types by day 4 (Dubay, D. A. and M. G. Franz, Surg Clin North Am, 2003, 83:463-81). Wounds are increasingly challenged during the recovery period as patients return to normal activity. Therefore, a medical device that can become populated with fibroblasts and vascularize faster than other bioprosthetics would reduce the recovery time and increase healing rates to improve repair outcomes.

The leading cause of death in the world today is cardiovascular disease (CVD)(Lopez et al., 2006, 367:1747-57), and the vast majority of CVD is related to impairment of blood flow through diseased atherosclerotic arteries. Stenting and bypass surgery are the most common interventions used to treat occluded arteries. Ideally, the patients own internal mammary artery or the saphenous vein are used as the graft material, but often autologous tissue conduits are not available (Faries et al., J Vasc Surg, 2000, 31:1119-27; Zhang et al., J Cell Mol Med, 2007, 11:945-57). Alternatively, synthetic conduits such as expanded polytetrafluoroethylene (ePTFE) or polyethylene terephthalate (Dacron) are used. For large caliber arteries (≥8 mm) Dacron grafts have largely been successful. In contrast, ePTFE, which is commonly used for small caliber arteries (≤6 mm), has a high incidence of failure due to intimal hyperplasia and ongoing surface thrombogenicity (Chlupac et al., Physiol Res, 2009, 58 Suppl 2:S119-39; Zilla et al., Biomaterials, 2007, 28:5009-27). The absence of a selectively permeable and thrombo-resistant endothelium is the main reason for the failure of medium to small-caliber prosthetic vascular grafts (Zhang et al., J Cell Mol Med, 2007, 11:945-57). Ingrowth of a vascular graft from neighboring endothelial cells (EC), and colonization of circulating endothelial progenitor cells (EPC) have resulted in endothelialization of vascular grafts in animal models (Zilla et al., Biomaterials, 2007, 28:5009-27; Shi et al., *Blood,* 1998, p. 362-67). Successful pre-clinical studies have not translated to the clinic in localizing these cell types to grafts to generate a non-thrombotic surface (Walter et al., *Circulation,* 2002, p. 3017-24; Werner et al., *Circ Res.* 2003, p. e17-24; Bhattacharya et al., in *Blood,* 2000, p. 581-5; Kaushal et al., in *Nat. Med.* 2001, p. 1035-40; Griese et al., in *Circulation,* 2003, p. 2710-5). Furthermore, new tissue engineering technologies are being developed to generate grafts made of both natural and/or synthetic scaffold material that promote endothelialization (Amiel et al., Tissue Eng, 2006, 12:2355-65; L'Heureux et al., Nat Med, 2006, 12:361-65; Tillman et al., Biomaterials, 2009, 30:583-8). Positive preclinical and clinical studies involving the seeding of cells at the luminal surface of prosthetic vascular grafts prior to implantation supports the concept that ECs and EPCs can improve functional outcomes in vivo (Bhattacharya et al., in *Blood.* 2000. p. 581-5; Deutsch et al., Surgery, 1999, 126:847-55; Meinhart et al., in *Ann Thorac Surg.* 2001. p. S327-31; Zilla et al., in *J Vasc Surg.* 1994. p. 540-8; Parikh, S. A. and E. R. Edelman, Adv Drug Deliv Rev, 2000, 42:139-61). However, EC seeding is laborious, expensive, can introduce contaminants, and is not always possible. Alternatively, mobilizing EPCs from bone marrow followed by capture of EPCs on a vascular graft represents an exciting alternative that eliminates most of the complications associated with cell seeding, and is currently being explored in the clinic with bare metal stents (Aoki et al., J Am Coll Cardiol, 2005, 45:1574-9). In animal models, small numbers of circulating EPCs have been shown to passively attach to implanted grafts and decrease neointima formation following vascular injury (Walter et al., in *Circulation.* 2002. p. 3017-24; Werner et al., in *Circ Res.* 2003. p. e17-24). A vascular graft that would promote better endothelialization would reduce intimal hyperplasia and thrombosis.

Therefore, while tissue remodeling can theoretically be achieved by application of cells and/or growth factors at the site of damaged tissue, several obstacles stand in the way of this regenerative technology becoming reality. One obstacle is that cells and/or growth factors injected into many tissues are rapidly cleared via the lymphatics or vascular drainage. In addition, the growth factors can have undesirable ectopic effects. Another obstacle is that the most widely used source of stem cells, bone marrow aspirate, often provides an inadequate amount of stem cells. As a result, use of allogeneic stem cells or culturing of stem cells to increase their number prior to use is frequently still required.

Thus, there remains a need for systems to locally bind, deliver, and retain cells and growth factors to a site of tissue in need of healing or repair. The presently disclosed subject matter provides such systems.

SUMMARY

The presently disclosed subject matter provides compositions and methods for tissue repair including cell binding peptides and implantable devices for tissue repair comprising the attached cell binding peptides. The tissue for repair includes tendon, muscle, connective tissue, ligament, cardiac tissue, vascular tissue, or dermis. The cell binding peptides bind to one or more of stem cells, fibroblasts, or endothelial cells.

In one embodiment, the presently disclosed subject matter provides compositions and methods for tissue repair including growth factor binding peptides and implantable devices for tissue repair comprising the attached growth factor binding peptides. The growth factor binding peptides include platelet derived growth factor (PDGF) binding peptides and growth differentiation factor (GDF) binding peptides. The tissue for repair includes tendon, muscle, connective tissue, ligament, cardiac tissue, vascular tissue, or dermis.

In one embodiment, the presently disclosed subject matter provides compositions and methods for tissue repair including implantable devices for tissue repair comprising the attached cell binding and more or more of the growth factor binding peptides. The tissue for repair includes tendon, muscle, connective tissue, ligament, cardiac tissue, vascular tissue, or dermis.

In one embodiment, the presently disclosed subject matter provides a method for tissue repair comprising delivering to a subject an implantable device comprising an attached cell binding peptide, wherein the implantable device serves as a scaffold for tissue repair. In one embodiment, the implantable device being delivered to the subject for tissue repair further comprises one or more of the growth factor binding peptides. The tissue for repair includes tendon, muscle, connective tissue, ligament, cardiac tissue, vascular tissue, or dermis.

In one embodiment, the presently disclosed subject matter provides a method for tissue repair comprising delivering to a subject an implantable device comprising an attached growth factor binding peptide, wherein the implantable device serves as a scaffold for tissue repair. The tissue for repair includes tendon, muscle, connective tissue, ligament, cardiac tissue, vascular tissue, or dermis.

In one embodiment, the presently disclosed subject matter provides a method for capturing cells onto an implantable device for tissue repair, the method comprising contacting a sample comprising cells with the implantable device comprising an attached cell binding peptide, wherein the cells comprised in the sample are captured onto the implantable device through binding to the attached cell binding peptide. In one embodiment, the sample comprising cells comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof. In one embodiment of the method for capturing cells, the implantable device further comprises an attached growth factor binding peptide, and the sample comprising cells also comprises the growth factor which is captured onto the implantable device through binding to the attached growth factor binding peptide.

In one embodiment, the presently disclosed subject matter provides a method for capturing a growth factor onto an implantable device for tissue repair, the method comprising contacting a sample comprising the growth factor with the implantable device comprising an attached growth factor binding peptide, wherein the growth factor comprised in the sample is captured onto the implantable device through binding to the attached growth factor binding peptide. In one embodiment, the sample comprising a growth factor comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof.

In one embodiment, the presently disclosed subject matter provides a method for tissue repair, the method comprising contacting a sample comprising cells with an implantable device comprising an attached cell binding peptide, wherein the cells comprised in the sample are captured onto the implantable device through binding to the attached cell binding peptide; and delivering to a subject the implantable device having the captured cells for tissue repair. In one embodiment, the implantable device further comprises an attached growth factor binding peptide, the sample comprising cells also comprises growth factor, and the growth factor comprised in the sample is captured onto the implantable device through binding to the attached growth factor binding peptide. The tissue for repair includes tendon, muscle, connective tissue, ligament, cardiac tissue, vascular tissue, or dermis. In one embodiment, the sample comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof.

In one embodiment, the presently disclosed subject matter provides a method for tissue repair, the method comprising contacting a sample comprising growth factor with an implantable device comprising an attached growth factor binding peptide which captures the growth factor comprised in the sample onto the implantable device; and delivering to a subject the implantable device for tissue repair. The tissue for repair includes tendon, muscle, connective tissue, ligament, cardiac tissue, vascular tissue, or dermis. In one embodiment, the sample comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof.

BRIEF DESCRIPTION OF THE DRAWINGS

FIG. 14 is a table showing an alignment of cell binding peptides from a phage display library selection.

FIG. 21A shows a peptide dependent increase in cell retention on peptide-modified collagen, with a 3-fold increase in cell retention for the peptide-modified collagen over unmodified collagen. The data in FIG. 21B show that the collagen coating was similar for all the samples shown in FIG. 21A. Peptide-modified collagen retained 7-fold more HUVECs than unmodified collagen (FIG. 21C).

In FIG. 27, sections from the periphery (panels A and B) or center (panels C and D) were incubated with an antibody against aggrecan (ABCAM) (panels B and D) or with secondary detection reagents only as a control (panels A and C), then counterstained with DAPI to reveal cell nuclei.

DETAILED DESCRIPTION

Figure 1:
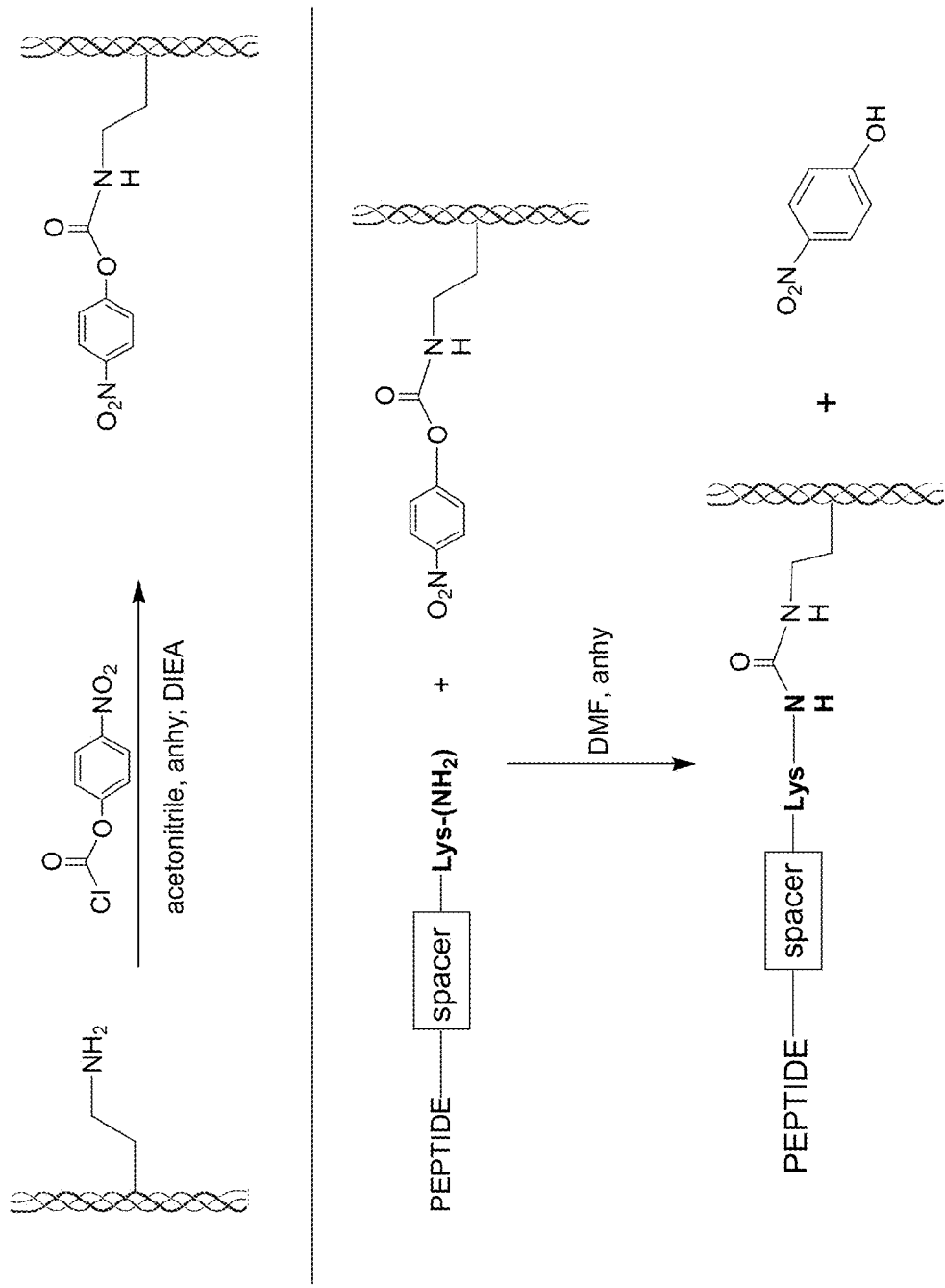
FIG. 1 is a schematic diagram depicting one method for covalently attaching a binding peptide to a substrate comprising amino functional groups.

The methods and compositions of the presently disclosed subject matter are described in greater detail herein below.

Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims. Thus, for example, reference to "a cell binding peptide" or reference to "a 1 unit polyethylene glycol ("mini-PEG" or "MP")" includes a plurality of such cell binding peptides or such polyethylene glycol units, and so forth.

The term "adipose tissue" as used herein, for the purposes of the specification and claims, includes the term "liposuction aspirate". Therefore, the term "stromal vascular fraction of adipose tissue" also means "stromal vascular fraction of liposuction aspirate".

The cell binding peptides and the growth factor binding peptides of the presently disclosed subject matter are herein collectively referred to as the "binding peptides". The term "cell binding peptide" is used herein, for the purposes of the specification and claims, to refer to an amino acid chain comprising a peptide that can bind to a cell and is set forth in any one of SEQ ID NOs: 1-20 described in Example 1 (i.e., the cell is the binding "target" of the cell binding peptide). The cell binding peptides of the presently disclosed subject matter bind one or more of stem cells, fibroblasts, or endothelial cells. In addition, the term "stem cell binding peptide" is in some cases herein used interchangeably, for the purposes of the specification and claims, with the terms "cell binding peptide" and "endothelial cell binding peptide" and "fibroblast binding peptide" as certain of the stem cell binding peptides described in Example 1 also bind to fibroblast and endothelial cells (see, e.g., Example 3).

The term "growth factor binding peptide" is used herein, for the purposes of the specification and claims, to refer to an amino acid chain comprising a peptide that can bind to a growth factor (i.e., the growth factor is the binding "target" of the growth factor binding peptide). In one embodiment, the growth factor is platelet derived growth factor (PDGF) or growth and differentiation factor (GDF) (a family of growth factors belonging to the family of BMPs including GDF-5 (BMP-14), GDF-6 (BMP-13), and GDF-7 (BMP-12)). In one embodiment, the growth factor is PDGF and the PDGF binding peptide is set forth in any one of SEQ ID NOs: 25, 28-33, 36, 38, 39 and peptide sequence motifs #1-5 (see Example 14). In one embodiment, the growth factor is GDF and the GDF binding peptide is set forth in US Patent Application Publication No. US 2009/0098175 A1 and is set forth therein as one of SEQ ID No's: 1-12 (i.e., these are the SEQ ID NO identifiers for the previously published patent application rather than this current one). In one embodiment, the GDF binding peptide is set forth in US Patent Application Publication No. US 2009/0098175A1 and is any one of SEQ ID NOs: 40-43 shown herein at Table 5.

The term "substrate" is used, for the purposes of the specification and claims, to refer to any material that is biologically compatible with cells and/or growth factors and to which a binding peptide can be attached for the purpose of capturing target cells and/or growth factors onto the substrate. The binding peptide attached to the substrate can be one or more of a cell binding peptide or a growth factor binding peptide, or combinations thereof. In one embodiment the substrate is in the form of an implantable device. Therefore, the terms "substrate" and "implantable device" are herein used interchangeably, for the purposes of the specification and claims. In one embodiment, the implantable device for tissue repair comprises a polymer having an attached binding peptide. Accordingly, the term "substrate" is used interchangeably herein with the term "polymer" for the purposes of the specification and claims when referring to the attachment of a binding peptide to a "substrate" it is meant that attachment of the binding peptide is to a polymer comprised in the substrate. Therefore, the attachment of a binding peptide to a "substrate" is referring to attachment of the binding peptide to the polymer comprised in the substrate.

In one embodiment, the substrate or implantable device can comprise any material and can be present in any form that is desirable and conducive to capturing cells onto the substrate such that the cells retain their native activity such as, for example, stem cells retaining their ability to differentiate into one or more cells of mesenchymal tissue lineage. Similarly, the substrate or implantable device can comprise any material and can be present in any form that is desirable and conducive to capturing growth factors onto the substrate such that the growth factors retain their biological growth factor activity. The term "implantable device" generally refers to a structure that is introduced into a human or animal body to restore a function of a damaged tissue or to provide a new function. Representative implantable devices include, but are not limited to, a gel, a hydrogel, an injectable polymeric material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft or mesh for breast reconstruction, a composite surgical mesh comprising a synthetic polymer and a biopolymer, and derivatives and combinations thereof.

In one embodiment, the implantable device for tissue repair comprises a polymer having an attached binding peptide. The term "polymer" is used herein, for the purposes of the specification and claims, to refer to a biopolymer or a synthetic polymer suitable for use in the compositions and methods of the presently disclosed subject matter. In one embodiment, a binding peptide is covalently attached to the biopolymer. In one embodiment, a binding peptide is covalently attached to the synthetic polymer. Biopolymers of the of the presently disclosed subject matter include, by non-limiting example, a collagen, an injectable collagen, a keratin, a silk, a polysaccharide, a dextran, an agarose, a cellulose derivative, an oxidized cellulose, an oxidized regenerated cellulose, a carboxymethylcellulose, a hydroxypropylmethylcellulose, a chitosan, a chitin, a hyaluronic acid, and derivatives and combinations thereof. Synthetic polymers of the presently disclosed subject matter include, by non-limiting example, a polyanhydride polymer where the anhydride groups are not present in the backbone of the polymer and the portion of the polyanhydride polymer chain that will not be hydrolyzed in vivo is small enough to allow efficient clearance through the renal system. Polymaleic anhydride (PMA) having molecular weight of about 5,000 Dalton or less is one example of a resorbable polyanhydride polymer for the purposes of the specification and claims. In another example, the synthetic polymer to which the binding peptide is attached is a block co-polymer of polymaleic anhydride having molecular weight of about 5,000 Dalton or less and a co-polymer comprising a biodegradable functionality, wherein the co-polymer is selected from the group consisting of polylactic acid (PLA), polyglycolic acid (PGA), polylactic-co-glycolic acid (PLGA), polycaprolactone, poly-3-hydroxybutyrate, poly(p-dioxanone) and copolymers thereof, polyhydroxyalkanoate, poly(propylene fumarate), poly(ortho esters), and polyanhydrides, and combinations thereof.

The implantable devices for tissue repair of the presently disclosed subject matter comprise a polymer having an attached binding peptide. A number of extracellular matrices and composites of absorbable and non-absorbable materials for soft tissue repair that comprise one or more of the biopolymers or synthetic polymers listed herein above are discussed in Grevious et al., Clin Plastic Surg, 2006, 33:181-97; Butler, C. E., Clin Plastic Surg, 2006, 33:199-211; Badylak, S. F., Biomaterials, 2007, 28:3587-93; and Longo et al., British Medical Bulletin, 2010, 94:165-88, each of which is herein incorporated by reference in its entirety. The extracellular matrices and composites described in the foregoing articles that comprise one or more of the biopolymers or synthetic polymers listed herein above are implantable devices to which a binding peptide of the presently disclosed subject matter is covalently attached (see, e.g., Example 8).

The term "attached" in reference to a binding peptide of the presently disclosed subject matter being "attached" to a polymer means, for the purposes of the specification and claims, a binding peptide being immobilized on the substrate by means that will enable capture of the binding peptide target onto the polymer. In the case of the cell binding peptides, the cell binding peptides can be "attached" to the polymer by means that will enable capture of cells onto the polymer such that the stem cells retain their native activity. In the case of the growth factor binding peptides, the growth factor binding peptides can be "attached" to the polymer by any means that will enable capture of growth factors onto the implantable device such that the growth factors retain their biological growth factor activity. A binding peptide can be attached to a polymer by any one of covalent bonding, non-covalent bonding including, one or more of hydrophobic interactions, Van der Weals forces, hydrogen bonds, ionic bonds, magnetic force, or avidin-, streptavidin-, and Neutravidin-biotin bonding.

The binding peptides of the presently disclosed subject matter can include naturally occurring amino acids, synthetic amino acids, genetically encoded amino acids, non-genetically encoded amino acids, and combinations thereof; however, an antibody is specifically excluded from the scope and definition of a binding peptide of the presently disclosed subject matter. A binding peptide used in accordance with the presently disclosed subject matter can be produced by chemical synthesis, recombinant expression, biochemical or enzymatic fragmentation of a larger molecule, chemical cleavage of larger molecule, a combination of the foregoing or, in general, made by any other method in the art, and preferably isolated.

Binding peptides useful in the presently disclosed subject matter also include peptides having one or more substitutions, additions, and/or deletions of residues relative to the sequence of an exemplary cell binding peptide or growth factor binding peptide shown herein at Tables 1-5, as long as the binding properties of the exemplary binding peptides to their targets are substantially retained. Thus, the binding peptides include those that differ from the exemplary sequences by about 1, 2, 3, 4, 5, 6, 7, 8, 9, or 10 amino acids, and include binding peptides that share sequence identity with the exemplary peptide of at least 65%, 66%, 67%, 68%, 69%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity can be calculated manually or it can be calculated using a computer implementation of a mathematical algorithm, for example, GAP, BESTFIT, BLAST, FASTA, and TFASTA, or other programs or methods known in the art. Alignments using these programs can be performed using the default parameters. A binding peptide can have an amino acid sequence consisting essentially of a sequence of an exemplary binding peptide or a binding peptide can have one or more different amino acid residues as a result of substituting an amino acid residue in the sequence of the exemplary binding peptide with a functionally similar amino acid residue (a "conservative substitution"); provided that the peptide containing the conservative substitution will substantially retain the binding activity of the exemplary binding peptide not containing the conservative substitution. Examples of conservative substitutions include the substitution of one non-polar (hydrophobic) residue such as alanine, isoleucine, valine, leucine, or methionine for another; the substitution between asparagine and glutamine, the substitution of one large aromatic residue such as tryptophan, tyrosine, or phenylalanine for another; the substitution of one small polar (hydrophilic) residue for another such as between glycine, threonine, serine, and proline; the substitution of one basic residue such as lysine, arginine, or histidine for another; or the substitution of one acidic residue such as aspartic acid or glutamic acid for another.

Accordingly, binding peptides useful in the presently disclosed subject matter include those peptides that are conservatively substituted variants of the binding peptides set forth in SEQ ID NOs: 1-16 (cell binding peptides), SEQ ID NOs: 25, 28-33, 36 (PDGF binding peptides), and SEQ ID NOs: 40-42 (GDF binding peptides), and those peptides that are variants having at least 65% sequence identity or greater to the binding peptides set forth in SEQ ID NOs: 1-16, SEQ ID NOs: 25, 28-33, 36, and SEQ ID NOs: 40-42, wherein all of the variant binding peptides useful in the presently disclosed subject matter substantially retain the ability to bind to their target.

Binding peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

Further, a binding peptide according to the presently disclosed subject matter can include one or more modifications, such as by addition of chemical moieties, or substitutions, insertions, and deletions of amino acids, where such modifications provide for certain advantages in its use, such as to facilitate attachment to the polymer with or without a spacer or to improve peptide stability. The term "spacer" is used herein, for the purposes of the specification and claims, to refer to a compound or a chemical moiety that is optionally inserted between a binding peptide and the polymer. In some embodiments, the spacer also serves the function of a linker (i.e. to attach the binding peptide to the polymer). Therefore, the terms "linker" and "spacer" can be used interchangeably herein, for the purposes of the specification and claims, when performing the dual functions of linking (attaching) the peptide to the polymer and spacing the binding peptide from the polymer. In some cases the spacer can serve to position the binding peptide at a distance and in a spatial position suitable for binding and capture and/or in some cases the spacer can serve to increase the solubility of the binding peptide. Spacers can increase flexibility and accessibility of the binding peptide to its target, as well as increase the binding peptide density on the polymer surface. Virtually all chemical compounds, moieties, or groups suitable for such a function can be used as a spacer unless adversely affecting the binding behavior to such an extent that binding of the target to the binding peptides is prevented or substantially impaired. Thus, the term "binding peptide" encompasses any of a variety of forms of binding peptide derivatives including, for example, amides, conjugates with proteins, conjugates with polyethylene glycol or other polymers, cyclic peptides, polymerized peptides, peptides having one or more amino acid side chain group protected with a protecting group, and peptides having a lysine side chain group protected with a protecting group. Any binding peptide derivative that has substantially retained target binding characteristics can be used in the practice of the presently disclosed subject matter.

Further, a chemical group can be added to the N-terminal amino acid of a binding peptide to block chemical reactivity of the amino terminus of the peptide. Such N-terminal groups for protecting the amino terminus of a peptide are well known in the art, and include, but are not limited to, lower alkanoyl groups, acyl groups, sulfonyl groups, and carbamate forming groups. Preferred N-terminal groups can include acetyl, 9-fluorenylmethoxycarbonyl (Fmoc), and t-butoxy carbonyl (Boc). A chemical group can be added to the C-terminal amino acid of a synthetic binding peptide to block chemical reactivity of the carboxy terminus of the peptide. Such C-terminal groups for protecting the carboxy terminus of a peptide are well known in the art, and include, but are not limited to, an ester or amide group. Terminal modifications of a peptide are often useful to reduce susceptibility by protease digestion, and to therefore prolong a half-life of a binding peptide in the presence of biological fluids where proteases can be present. In addition, as used herein, the term "binding peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO), and a thiopeptide bond (CS—NH).

In one embodiment, the binding peptides are covalently attached to the polymer comprised in the implantable device. In one embodiment, the linkers/spacers for use in attaching binding peptides to polymers have at least two chemically active groups (functional groups), of which one group binds to the polymer, and a second functional group binds to the binding peptide or in some cases it binds to the "spacer" already attached to the binding peptide. Preferably, the attachment of the binding peptides to the polymer is effected through a spacer. Virtually all chemical compounds, moieties, or groups suitable for such a function can be used as a spacer unless adversely affecting the peptide binding behavior to such an extent that binding of the target to the binding peptides is prevented or substantially impaired.

Again, the terms "linker" and "spacer" can be used interchangeably herein, for the purposes of the specification and claims, when performing the dual functions of linking (attaching) the binding peptide to the polymer and spacing the peptide from the polymer. In many embodiments herein, the linkers used to attach the binding peptide to the polymer function as both a linker and a spacer. For example, a linker molecule can have a linking functional group on either end while the central portion of the molecule functions as a spacer. The binding peptides of the presently disclosed subject matter can comprise a functional group that is intrinsic to the binding peptide (e.g., amino groups on lysine), or the functional group can be introduced into the binding peptide by chemical modification to facilitate covalent attachment of the binding peptide to the polymer. Similarly, the polymer can comprise a functional group that is intrinsic to the polymer (e.g., amino groups on collagen), or the polymer can be modified with a functional group to facilitate covalent attachment to the binding peptide. The binding peptide can be covalently attached to the polymer with or without one or more spacer molecules.

For example, linkers/spacers are known to those skilled in the art to include, but are not limited to, chemical compounds (e.g., chemical chains, compounds, reagents, and the like). The linkers/spacers may include, but are not limited to, homobifunctional linkers/spacers and heterobifunctional linkers/spacers. Heterobifunctional linkers/spacers, well known to those skilled in the art, contain one end having a first reactive functionality (or chemical moiety) to specifically link a first molecule (e.g, polymer), and an opposite end having a second reactive functionality to specifically link to a second molecule (e.g, binding peptide). It is evident to those skilled in the art that a variety of bifunctional or polyfunctional reagents, both homo- and hetero-functional can be employed as a linker/spacer with respect to the presently disclosed subject matter such as, for example, those described in the catalog of the PIERCE CHEMICAL CO., Rockford, Ill.; amino acid linkers/spacers that are typically a short peptide of between 3 and 15 amino acids and often containing amino acids such as glycine, and/or serine; and wide variety of polymers including, for example, polyethylene glycol. In one embodiment, representative linkers/spacers comprise multiple reactive sites (e.g., polylysines, polyornithines, polycysteines, polyglutamic acid and polyaspartic acid) or comprise substantially inert peptide spacers (e.g., polyglycine, polyserine, polyproline, polyalanine, and other oligopeptides comprising alanyl, serinyl, prolinyl, or glycinyl amino acid residues). In one embodiment, representative spacers between the reactive end groups in the linkers include, by non-limiting example, the following functional groups: aliphatic, alkene, alkyne, ether, thioether, amine, amide, ester, disulfide, sulfone, and carbamate, and combinations thereof. The length of the spacer can range from about 1 atom to 200 atoms or more. In one embodiment, linkers/spacers comprise a combination of one or more amino acids and another type of spacer or linker such as, for example, a polymeric spacer.

Suitable polymeric spacers/linkers are known in the art, and can comprise a synthetic polymer or a natural polymer. Representative synthetic polymer linkers/spacers include but are not limited to polyethers (e.g., poly(ethylene glycol) ("PEG"), 11 unit polyethylene glycol ("PEG10"), or 1 unit polyethylene glycol ("mini-PEG" or "MP"), poly(propylene glycol), poly(butylene glycol), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, and polyhexanoic acid, and combinations thereof. Polymeric spacers/linkers can comprise a diblock polymer, a multi-block copolymer, a comb polymer, a star polymer, a dendritic or branched polymer, a hybrid linear-dendritic polymer, a branched chain comprised of lysine, or a random copolymer. A spacer/linker can also comprise a mercapto(amido)carboxylic acid, an acrylamidocarboxylic acid, an acrlyamido-amidotriethylene glycolic acid, 7-aminobenzoic acid, and derivatives thereof.

In one embodiment, the binding peptide comprises one or more modifications to the peptide N-terminus, peptide C-terminus, or within the peptide amino acid sequence, to facilitate covalent attachment of the binding peptide to a polymer device with or without a spacer. The binding peptides can comprise one or more modifications including, but not limited to, addition of one or more groups such as hydroxyl, thiol, carbonyl, carboxyl, ester, carbamate, hydrazide, hydrazine, isocyanate, isothiocyanate, amino, alkene, dienes, maleimide, $\alpha,\beta$-unsaturated carbonyl, alkyl halide, azide, epoxide, N-hydroxysuccinimide (NHS) ester, lysine, or cysteine. In addition, a binding peptide can comprise one or more amino acids that have been modified to contain one or more chemical groups (e.g., reactive functionalities such as fluorine, bromine, or iodine) to facilitate linking the binding peptide to a spacer molecule or to the substrate to which the binding peptide will be attached.

The binding peptides can be covalently attached to the substrate through one or more anchoring (or linking) groups on the substrate and the binding peptide. The binding peptides of the presently disclosed subject matter can comprise a functional group that is intrinsic to the binding peptide, or the binding peptide can be modified with a functional group to facilitate covalent attachment to the substrate with or without a spacer. Representative anchoring (or linking) groups include by non-limiting example hydroxyl, thiol, carbonyl, carboxyl, ester, carbamate, hydrazide, hydrazine, isocyanate, isothiocyanate, amino, alkene, dienes, maleimide, $\alpha,\beta^\sim$-unsaturated carbonyl, alkyl halide, azide, epoxide, NHS ester, lysine, and cysteine groups on the surface of the substrate. The anchoring (or linking) groups can be intrinsic to the material of the substrate (e.g., amino groups on a collagen or on a polyamine-containing polymer) or the anchoring groups can be introduced into the substrate by chemical modification.

By way of non-limiting example, in one embodiment, a binding peptide is attached to a substrate in a two step process (see FIG. 1; Mikulec & Puleo, 1996, J. Biomed. Mat. Res., Vol 32, 203-08). In the first step, the anchoring (or linking) groups (i.e., amino groups on a collagen for example) on the surface of a substrate are activated by an acylating reagent (4-nitrophenyl chloroformate). In the second step, a lysine residue which has been introduced along with a PEG10 spacer at the C-terminus of a binding peptide is reacted with the activated chloroformate intermediate on the substrate surface, resulting in attachment of the binding peptide to the substrate.

Figure 2:
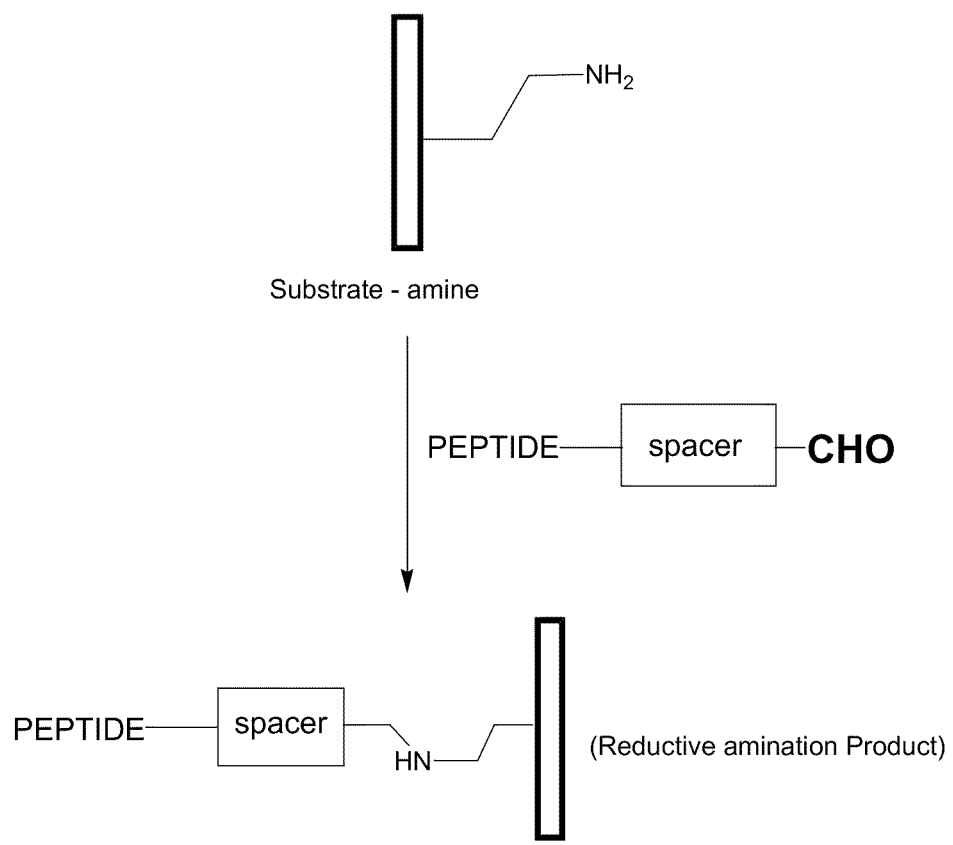
FIG. 2 is a schematic diagram depicting one method for covalently attaching a binding peptide to a substrate comprising amino functional groups.

By way of non-limiting example, in one embodiment, a binding peptide is covalently attached to a substrate comprising an amino functional group (see FIG. 2). FIG. 2 exemplifies attachment of a binding peptide comprising an aldehyde group at one terminus to a substrate that comprises an amino functional group. The binding peptide comprising an aldehyde functional group is treated with the substrate amino groups under reductive amination conditions to give attached binding peptide. In another embodiment not depicted in FIG. 2, a binding peptide comprising an amine functional group is reacted with the substrate amino groups via a homobifunctional linker such as, for example, glutaraldehyde, to yield a covalently attached binding peptide (Simionescu et. al., 1991, J. Biomed Mater. Res., 25:1495-505).

Figure 3:
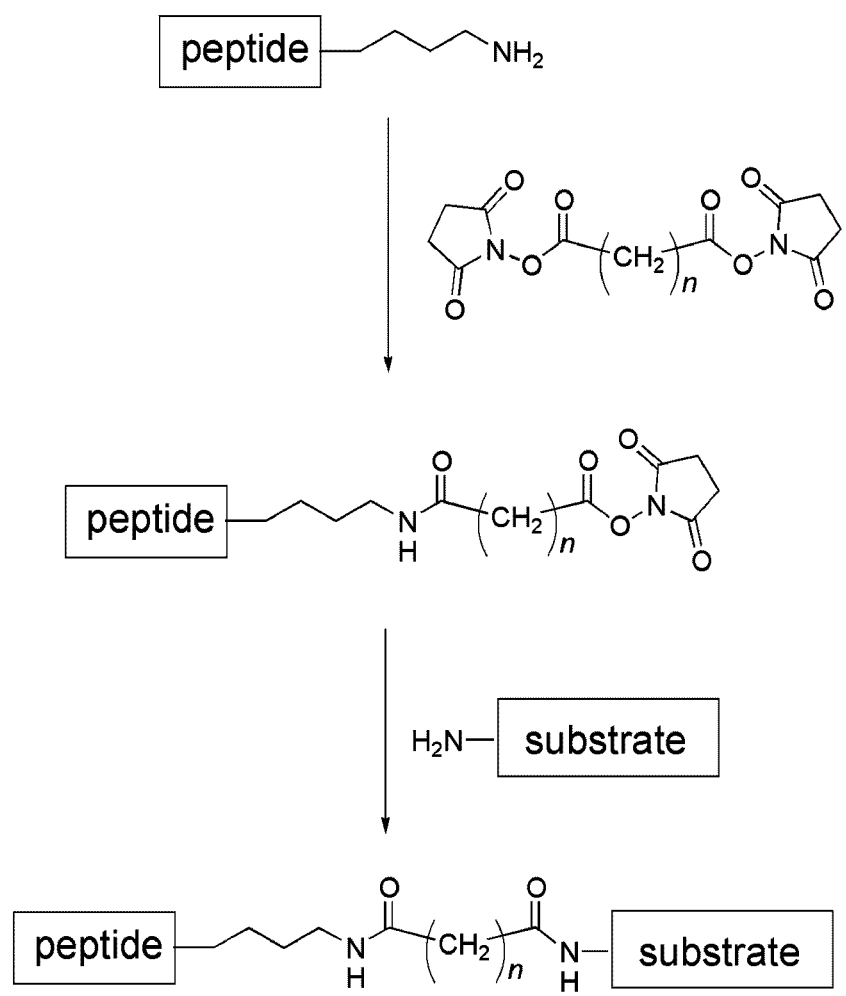
FIG. 3 is a schematic diagram depicting methods for covalently attaching a binding peptide to a substrate having an amino functional group.

By way of non-limiting example, in one embodiment, a homobifunctional linker possessing N-hydroxysuccinimide esters at both ends is reacted at one end with the binding peptide having an amino group (FIG. 3). The binding peptide with attached linking group is then reacted through the remaining N-hydroxysuccinimide ester with an amino group on the substrate to form a peptide-substrate conjugate (FIG. 3). The homobifunctional N-hydroxysuccinimide ester depicted in FIG. 3 is $BS^3$ crosslinking reagent (THERMO SCIENTIFIC, Rockford, Ill.). As stated herein previously, the length and type of spacer groups between the two reactive end groups on the NHS ester can vary.

Figure 4:
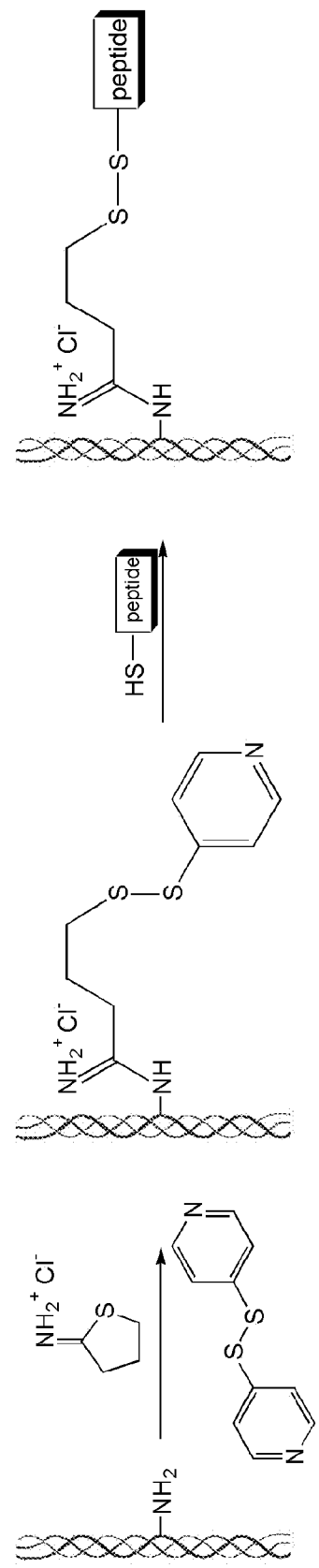
FIG. 4 is a schematic diagram depicting one method for covalently attaching a binding peptide to a substrate comprising amino functional groups.

By way of non-limiting example, in one embodiment, a binding peptide is covalently attached to a substrate having amino functional groups in a two-step process using a disulfide linkage (see FIG. 4; Hermanson, G. T. *Bioconjugate Techniques; Academic Press: San Diego,* 1996; pp. 150-151). First, the substrate containing amino groups is reacted with 2-iminothiolane resulting in the introduction of thiol groups on the substrate. Simultaneous addition of 4,4'-dithiodipyridine or 6,6'-dithiodinicotinic acid results in rapid capping of the newly-introduced thiol as a pyridyl disulfide. Second, the binding peptide containing a free thiol is attached covalently to the substrate through a thiol-disulfide exchange resulting in a disulfide bond between the substrate and binding peptide.

Figure 5:
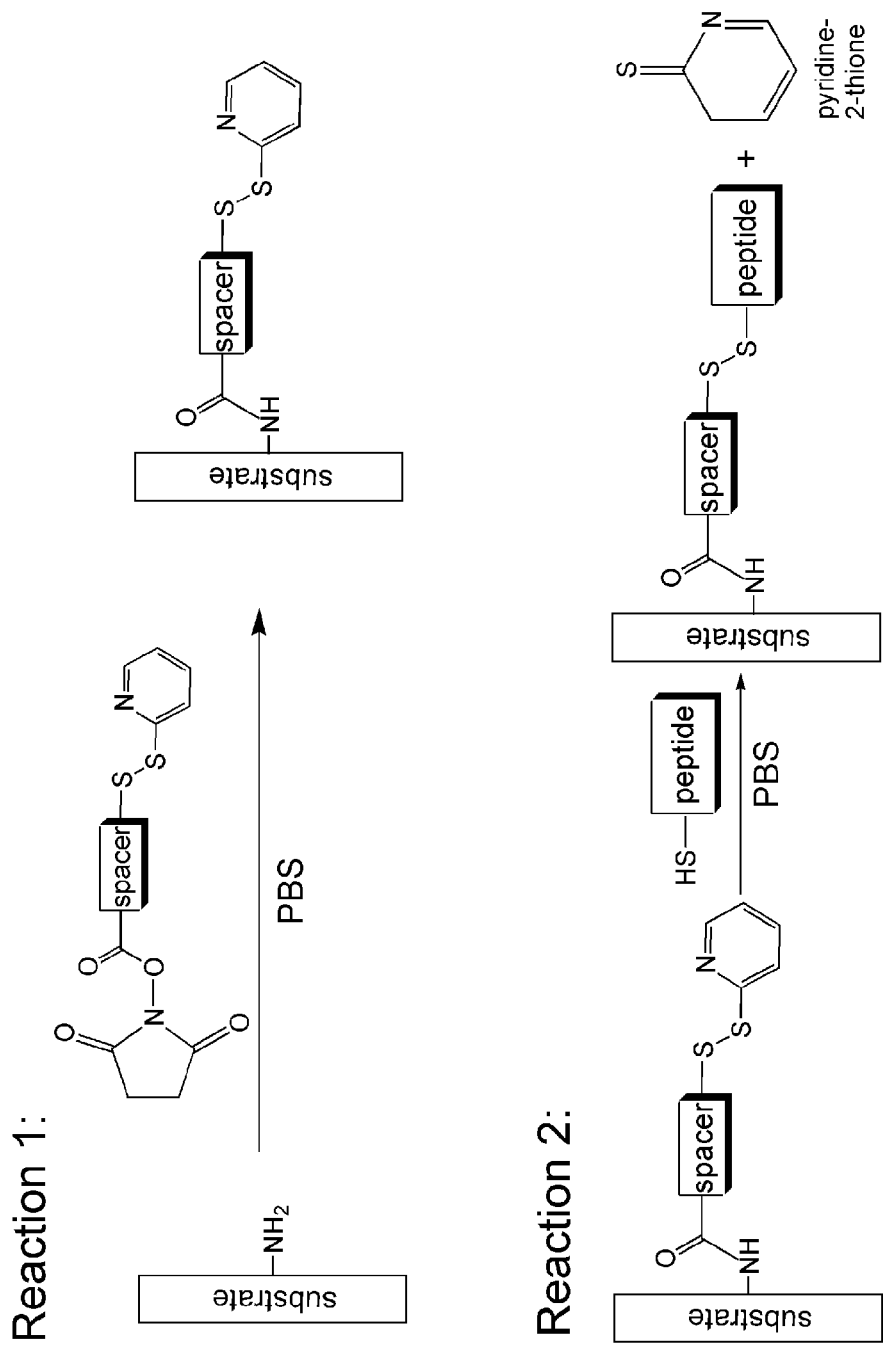
FIG. 5 is a schematic diagram depicting one method for covalently attaching a binding peptide to a substrate comprising amino functional groups.

By way of non-limiting example, in one embodiment, a binding peptide is attached covalently to a substrate comprising amino functional groups in a similar process using a disulfide linkage (see FIG. 5; Carlsson et al., 1978, Biochem. J., 173:723-37). The substrate is first functionalized with amine groups using known methods (if the amino groups are not intrinsic to the material of the substrate). Next, a thiol-cleavable, heterobifunctional (amine- and sulfhydryl-reactive) compound (LC-SPDP; THERMO SCIENTIFIC, Rockford, Ill.) is reacted with the amino-functionalized substrate. The binding peptide is reacted with the LC-SPDP modified substrate.

By way of non-limiting example, in one embodiment, a binding peptide is attached covalently to a substrate via a thioether bond formed by reaction of a thiol and maleimide (O'Sullivan et al., 1979, Anal. Biochem., 100:100-8). In one embodiment, the maleimide is added to a substrate comprising amino functional groups and then the modified substrate is reacted with a binding peptide having a free thiol group. Alternatively, in one embodiment, the same chemical scheme is utilized but with the substrate modified with a thiol group and the binding peptide modified with the maleimido group.

Figure 6:
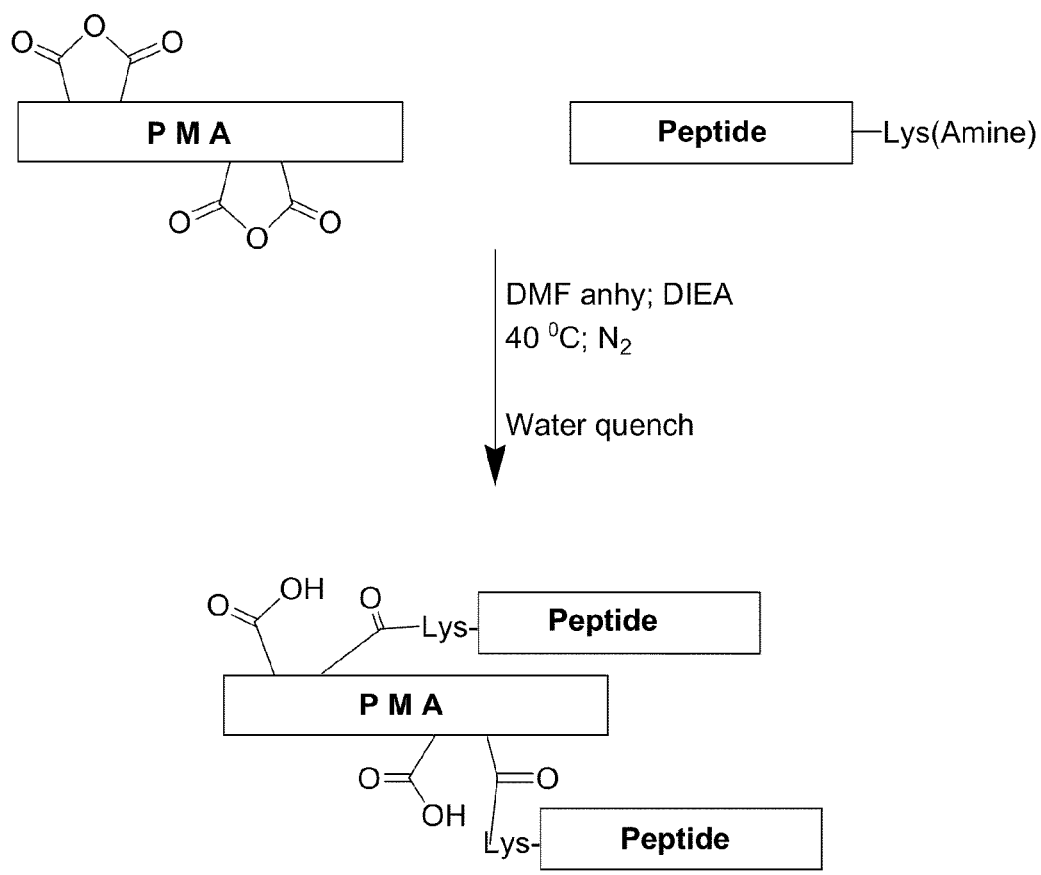
FIG. 6 is a schematic diagram depicting the chemistry for covalently attaching a binding peptide to a polyanhydride polymer, polymaleic anhydride (PMA), through the reactive amines on the peptide.

By way of non-limiting example, in one embodiment, a binding peptide is covalently attached through a non-backbone anhydride group of a polyanhydride polymer, polymaleic acid (PMA), through a reactive lysine group on the binding peptide shown in the schematic diagram in FIG. 6 (Pompe, et al., 2003, Biomacromolecules, 4(4):1072-9).

Figure 7:
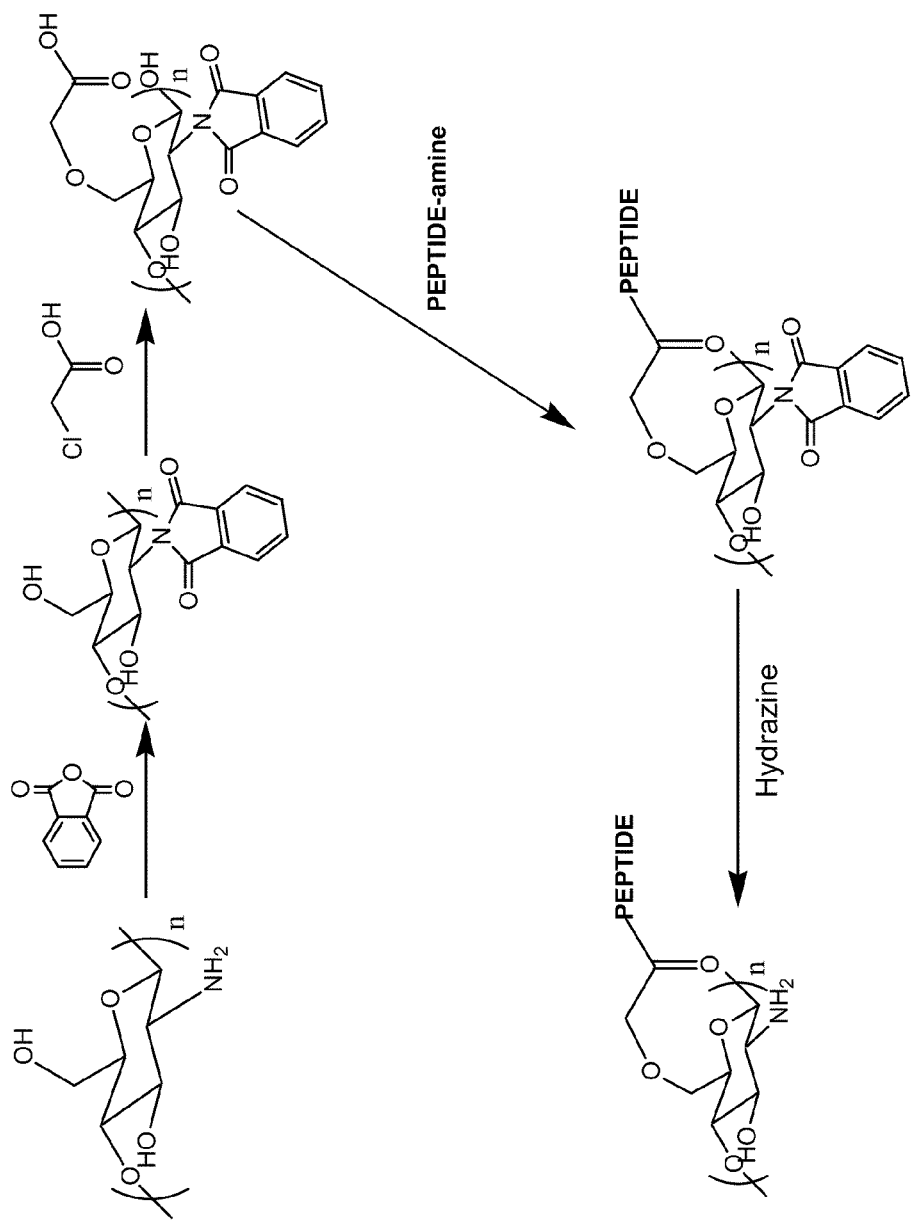
FIG. 7 is a schematic diagram depicting exemplary chemistry for covalently attaching a binding peptide to chitosan.

By way of non-limiting example, in one embodiment, a binding peptide is covalently attached to a chitosan. The chemical scheme is shown in FIG. 7. First, the amino group on chitosan is protected with phthaloyl group. The hydroxyl group on chitosan is then reacted with chloroacetic acid to give an acid handle on chitosan. The binding peptide amine is coupled to the acid group on the chitosan to give the binding peptide-chitosan conjugate. The phthaloyl group is then removed using hydrazine.

Figure 8:
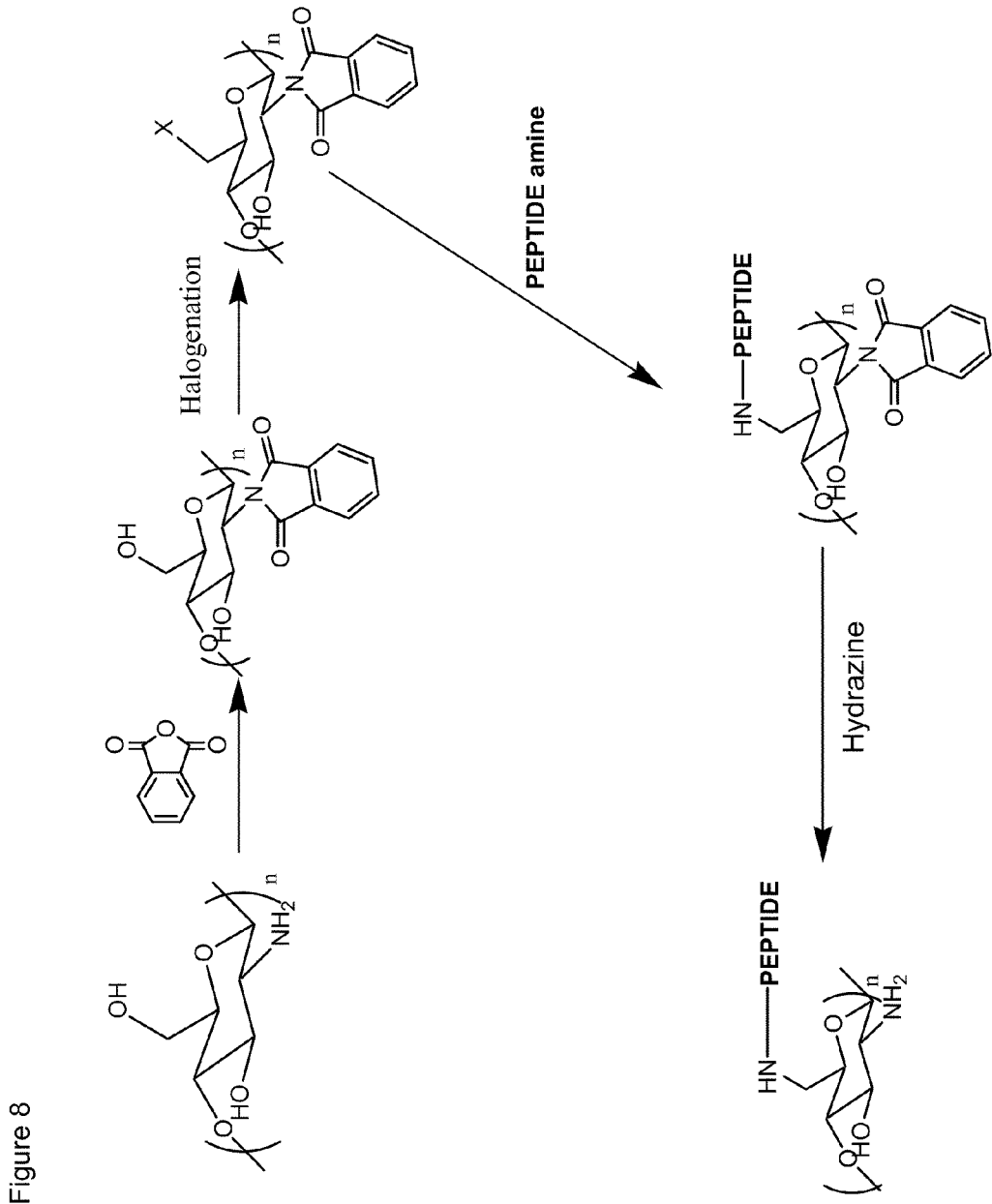
FIG. 8 is a schematic diagram depicting exemplary chemistry for covalently attaching a binding peptide to chitosan.

By way of non-limiting example, in one embodiment a binding peptide is covalently attached to a chitosan. The chemical scheme is shown in FIG. 8. First, the amino group on chitosan is protected with a phthaloyl group. The hydroxyl group on chitosan is then converted to a bromo group under standard halogenation conditions. The binding peptide amine is reacted with halogenated chitosan to give the binding peptide-chitosan conjugate. The phthaloyl group is finally removed by reacting with hydrazine.

By way of non-limiting example, in one embodiment a binding peptide is covalently attached to chitosan through the amino group on chitosan. For example, a chemical scheme using a homobifunctional N-hydroxysuccinimide ester, such as that described for FIG. 3, is useful for attaching the binding peptide through the amino group on chitosan.

Figure 9:
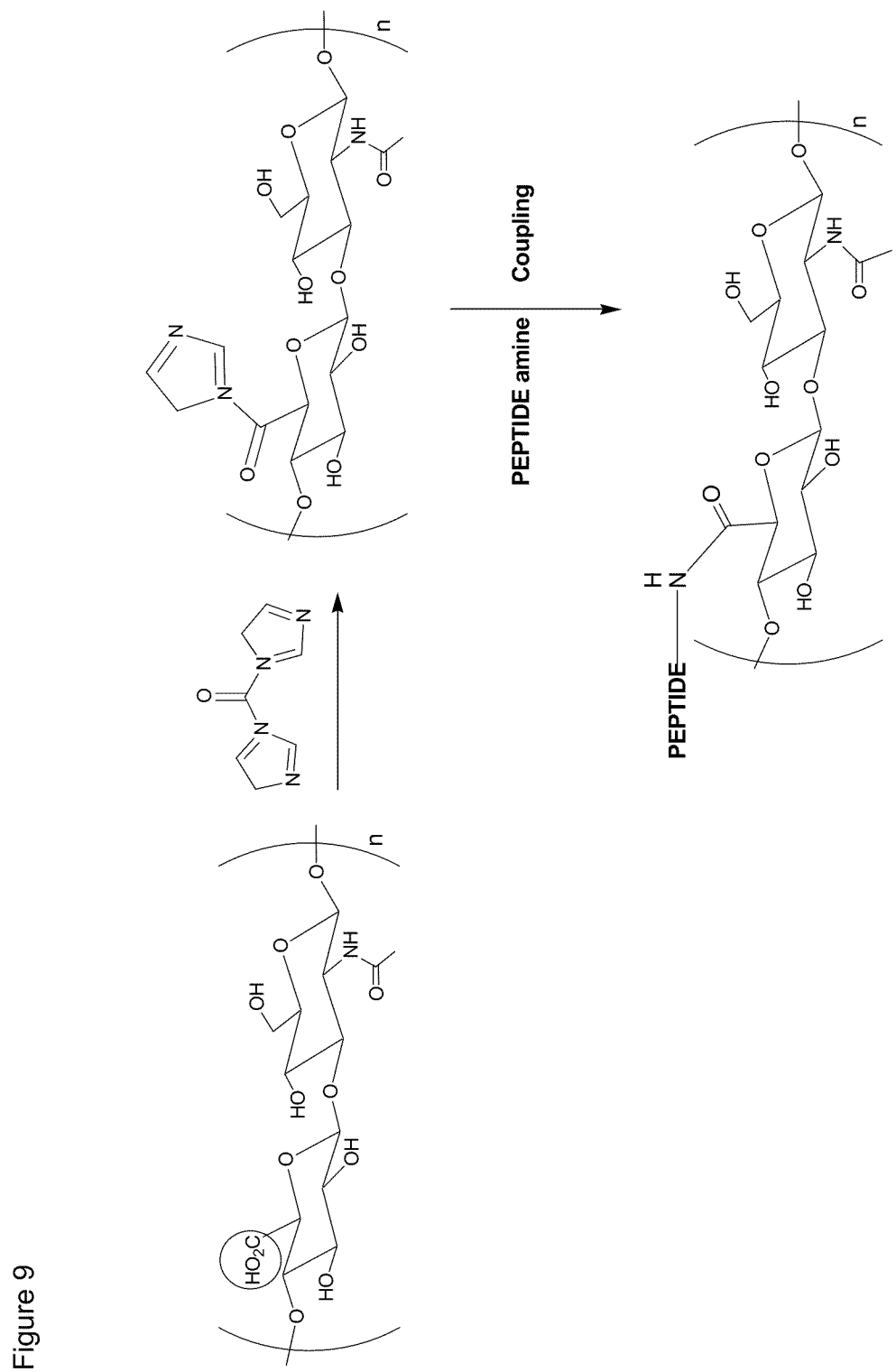
FIG. 9 is a schematic diagram depicting exemplary chemistry for covalently attaching a binding peptide to hyaluronic acid.

By way of non-limiting example, in one embodiment a binding peptide is covalently attached to a hyaluronan (HA). The chemical scheme is shown in FIG. 9. The hyaluronan is chemically modified at the carboxylic acid group on the glucuronate units. The carboxylic group is activated using carbonyl diimidazole (CD). The activated HA is then reacted with the amino group of binding peptide to yield the peptide-HA conjugate.

Figure 10:
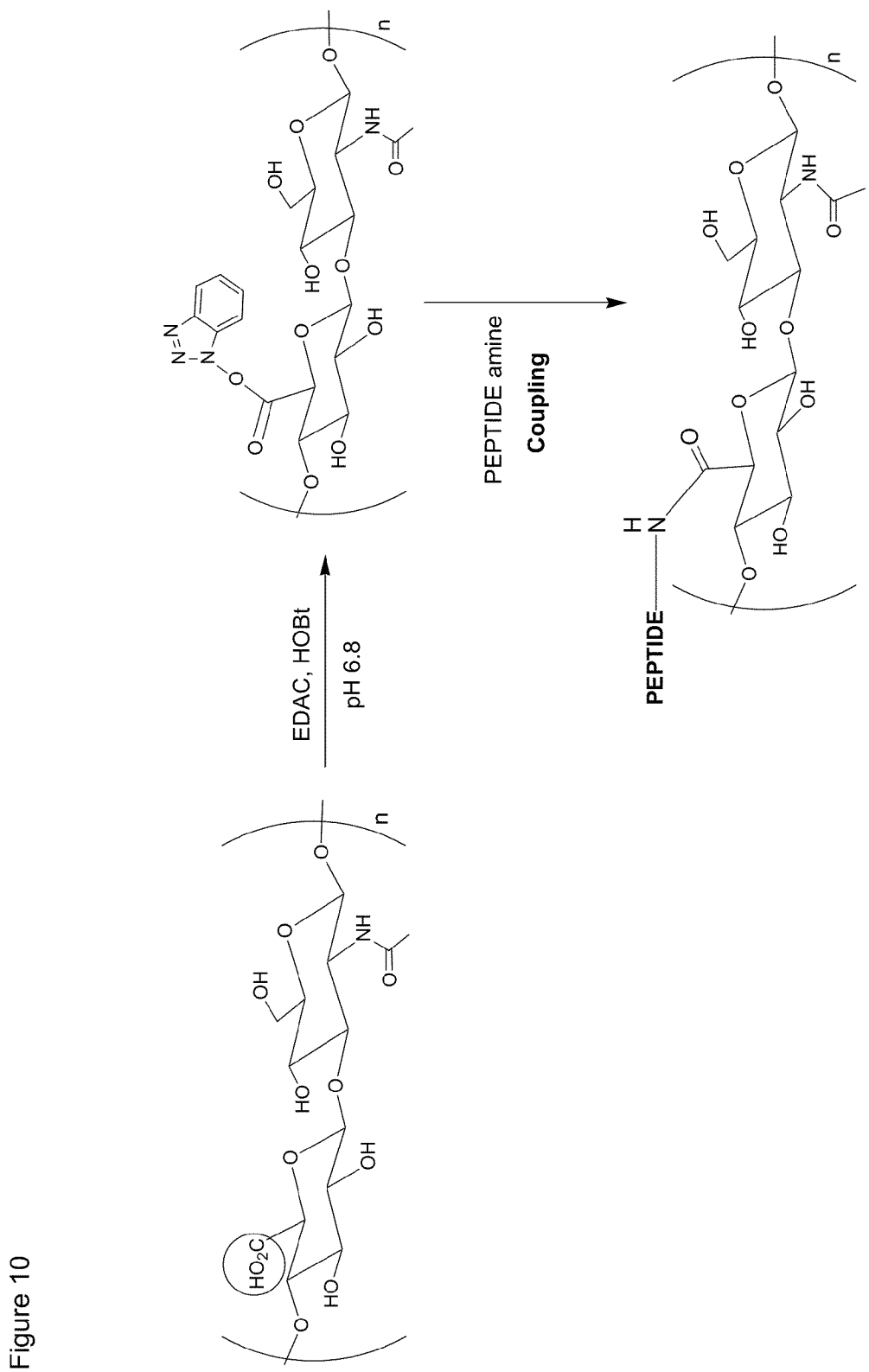
FIG. 10 is a schematic diagram depicting exemplary chemistry for covalently attaching a binding peptide to hyaluronic acid.

By way of non-limiting example, in one embodiment, a binding peptide is covalently attached to a hyaluronan (HA). The chemical scheme is shown in FIG. 10. Hyaluronan is chemically modified at the carboxylic acid group on the glucuronate units. The carboxylic group is activated using water soluble carbodiimide such as 1-ethyl-3-(3-dimethylaminopropyl) carbodiimide (EDC) along with HOBt. The activated HA is coupled with the amino group of a binding peptide to yield the peptide-HA conjugate.

Figure 11:
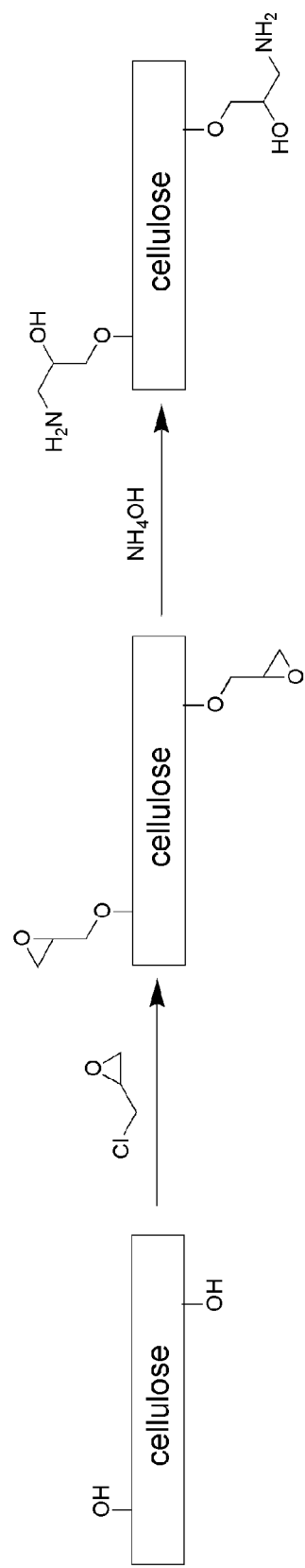
FIG. 11 is a schematic diagram depicting exemplary chemistry for introducing an amino functional group on cellulose for subsequent covalent attachment of a binding peptide.

By way of non-limiting example, in one embodiment, a binding peptide is covalently attached to cellulose. The chemical scheme is shown in FIG. 11. Hydroxyl groups on the polysaccharide are first reacted with epichlorohydrin to introduce an epoxide. Ring opening of the epoxide by reaction with aqueous ammonia provides free amino groups that can function as anchors for peptide conjugation using chemistry described in previous embodiments (Matsumoto, et al. (1980) *J. Biochem.*, 87: 535-540).

Figure 12:
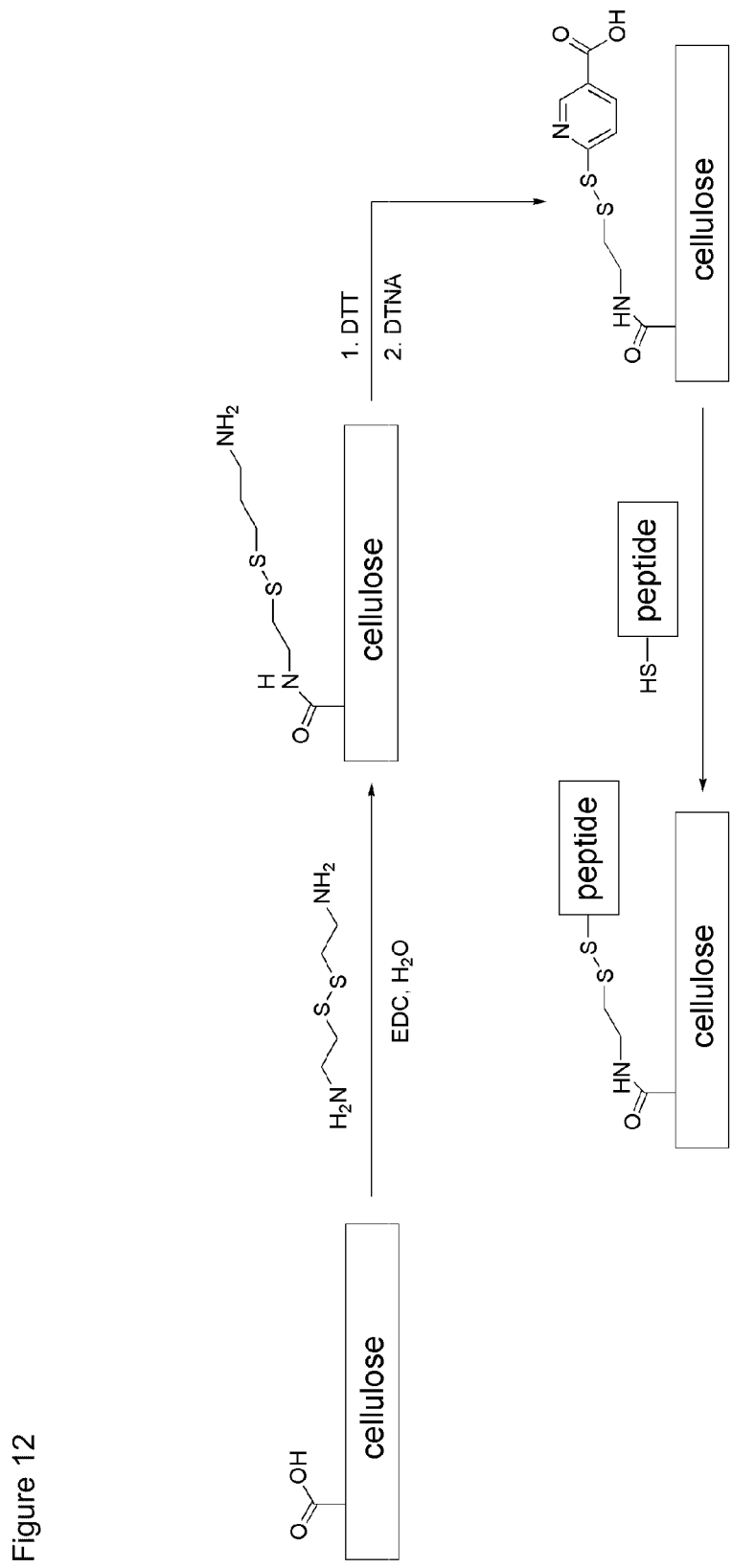
FIG. 12 is a schematic diagram depicting exemplary chemistry for covalently attaching a binding peptide to oxidized cellulose.

By way of non-limiting example, in one embodiment, a binding peptide is covalently attached to oxidized cellulose. The chemical scheme is shown in FIG. 12. Sulfhydryl groups are introduced by reaction of carboxylates on the oxidized cellulose with cystamine and EDC followed by reduction with dithiothreitol (DTT). Activation of sulfhydryls with 6,6'-dithiodinicotinic acid (DTNA) followed by a sulfhydryl-containing binding peptide results in covalent attachment of the peptide to the oxidized cellulose through a disulfide bond. In another embodiment not depicted in FIG. 12, the sulfhydryl modified oxidized cellulose is reacted with a maleimide or other Michael acceptor on the binding peptide resulting in covalent attachment through a thioether bond. In another embodiment not depicted in FIG. 12, carboxyl groups on oxidized cellulose are activated with EDC and 1-hydroxybenzotriazole (HOBt) followed by reaction with cell binding peptide containing a free amine group. This results in conjugation of peptide to the oxidized cellulose through an amide bond (this chemistry is exemplified in FIG. 10). In another embodiment not depicted in FIG. 12, a cell binding peptide can be covalently attached to oxidized cellulose through the aldehyde groups on the oxidized cellulose. In this example, a cell binding peptide having a free amine undergoes reductive amination with the aldehyde group on the polymer substrate to yield an amine bond as shown in FIG. 2 (the chemistry is the same as that in FIG. 2 except that the functional groups on the polymer substrate and cell binding peptide are reversed).

By way of non-limiting example, in one embodiment, a cell binding peptide can be covalently attached to an oxidized dextran polymer substrate by reductive amination as described above for oxidized cellulose. More specifically, a cell binding peptide having a free amine undergoes reductive amination with the aldehyde group on the polymer substrate to yield an amine bond as shown in FIG. 2 (the chemistry is the same as that in FIG. 2 except that the functional groups on the polymer substrate and cell binding peptide are reversed).

By way of non-limiting example, in one embodiment, more than one binding peptide is attached to a substrate. Attaching multiple binding peptides to a single substrate is only limited by practical considerations related to the method of attachment. For example, in one embodiment, two different binding peptides are covalently attached to a substrate using any of the chemical schemes shown in FIGS. 1-12. In each of the chemical schemes depicted in FIGS. 1-12, the substrate having a functional group is reacted with two or more different binding peptides that each comprise a functional group to covalently attach the two or more binding peptides to the substrate based on simple competition between the binding peptides. In particular, for example, in the case of the chemical schemes depicted in FIGS. 1 and 2, the modified substrate is reacted with two or more different binding peptides that each comprise an amino group or an aldehyde group (i.e., the two different binding peptides replace the single peptide depicted in FIGS. 1 and 2), to covalently attach the two or more binding peptides to the substrate through the amino or aldehyde group, respectively. In the case of the chemical schemes depicted in FIGS. 4 and 5, the modified substrate is reacted with two or more different binding peptides that each comprise a thiol group, to covalently attach the two or more binding peptides to the substrate through the thiol group (i.e., the "HS-Peptide" in FIGS. 4 and 5 in this embodiment represents two or more different binding peptides).

Figure 13:
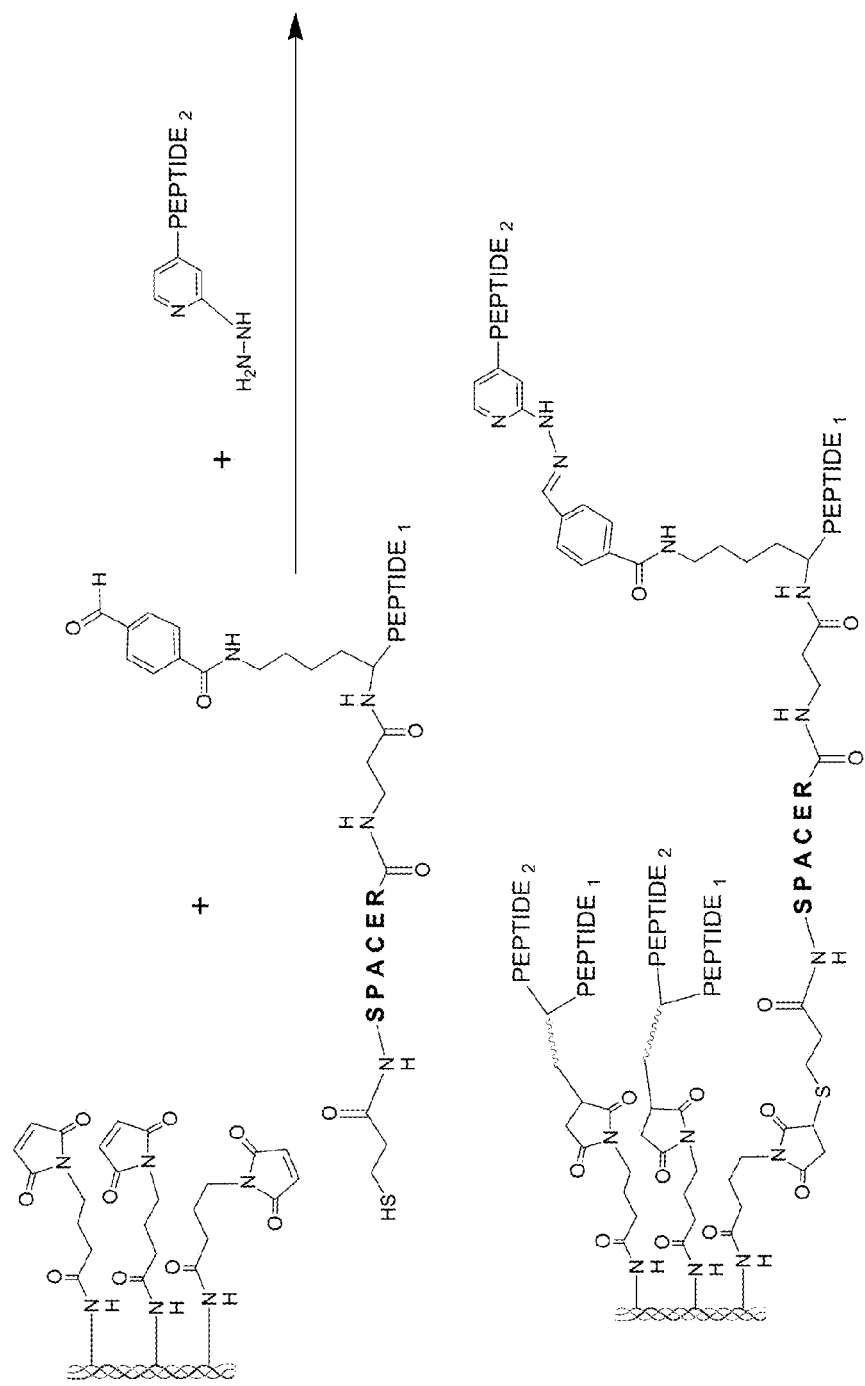
FIG. 13 is a schematic diagram depicting one method for covalently attaching more than one binding peptide to a substrate comprising amino functional groups.
Figure 15:
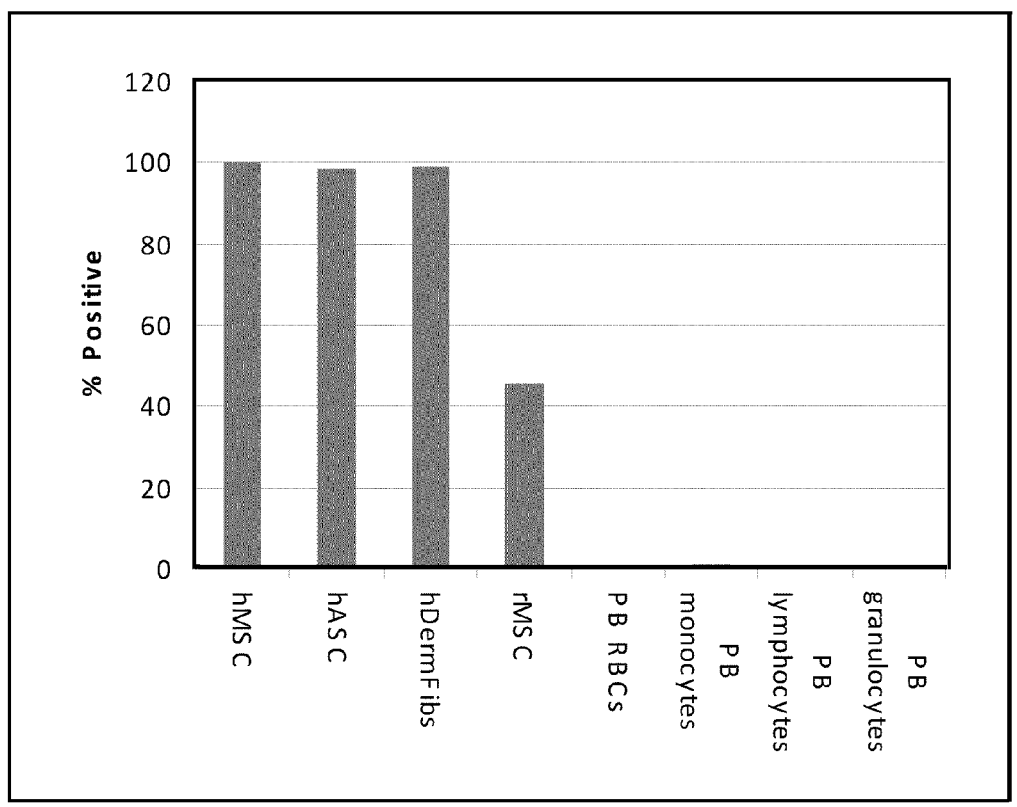
FIG. 15 is a bar graph showing the ability of stem cell binding peptide SEQ ID NO: 4 to specifically bind human mesenchymal stem cells (hMSCs) from bone marrow compared to a number of other cells types including human adipose-derived mesenchymal stem cells (hASCs), human dermal fibroblasts, rodent MSCs, red blood cells (RBCS), monocytes, lymphocytes and granulocytes. The y axis shows biotinylated stem cell binding peptide SEQ ID NO: 4 reactivity as percent positively relative to Neutravidin-PE staining without the addition of biotinylated peptide.
Figures 16A, 16B, 16C:
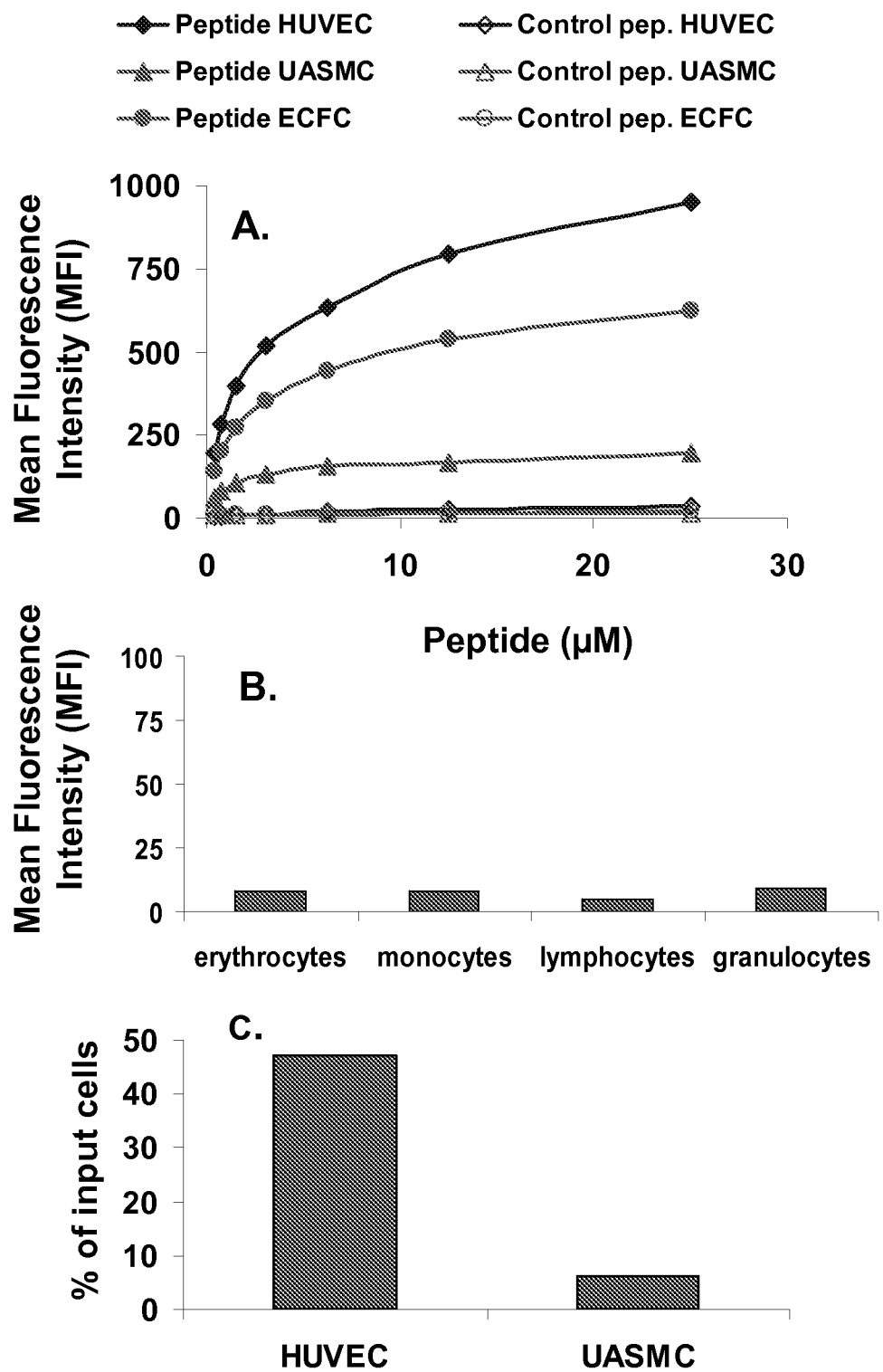
FIGS. 16A-16C are graphs showing the ability of cell binding peptide SEQ ID NO: 4 to bind endothelial cells compared to other cell types. The cell binding peptide was incubated with human umbilical vein endothelial cells (HUVECs), endothelial colony forming cells (ECFCs), umbilical artery smooth muscle cells (UASMCs) or whole blood cells. The data in FIGS. 16A & 16B show that SEQ ID NO: 4 cross-reacted strongly with ECFCs and HUVECs, weakly with UASMCs, and had no cross-reactivity with peripheral blood cells. The cell binding peptide was assayed for its ability to selectively isolate endothelial cells versus smooth muscle cells in the presence of whole blood. The data in FIG. 16C show that the cell binding peptide isolated 8-fold more HUVECs compared to UASMCs.

By way of non-limiting example, in one embodiment, two different binding peptides are covalently attached to a substrate comprising amino groups using the chemical scheme shown in FIG. 13. In this embodiment, the amino groups on the substrate are modified with maleimido groups. The modified substrate is then reacted with a binding peptide comprising both a thiol group and an aldehyde group to covalently attach the binding peptide to the substrate through the thiol group. Next, the substrate-binding peptide conjugate is reacted with another binding peptide having a hydrazine group, to give a second covalent bond through the aldehyde-hydrazine (see FIG. 13). Alternatively, in one embodiment, the same chemical scheme is utilized but with the substrate modified with a thiol group and the binding peptide modified with the maleimido group. In addition to using this scheme to covalently attach different binding peptides, the scheme is also useful for attaching the same binding peptide.

In one embodiment, the presently disclosed subject matter provides cell binding peptides. In one embodiment, the cell binding peptides comprise a sequence selected from the group consisting of SEQ ID NOs: 1-20. In one embodiment, the cell binding peptides comprise a sequence selected from the group consisting of SEQ ID NOs: 1-16, conservatively substituted variants of SEQ ID NOs: 1-16, and variants having at least 70% sequence identity to SEQ ID NOs: 1-16, wherein the variant cell binding peptide substantially retains the ability to bind cells consisting of SEQ ID NOs: 1-20. The cell binding peptides bind to one or more of fibroblasts, endothelial cells, or stem cells.

In one embodiment, the presently disclosed subject matter provides platelet derived growth factor (PDGF) binding peptides. In one embodiment, the PDGF peptides comprise a sequence selected from the group consisting of SEQ ID NOs:

25, 28-33, 36, 38, 39, and peptide sequence motifs #1-5; conservatively substituted variants of SEQ ID NOs: 25, 28-33, 36; and variants having at least 70% sequence identity to SEQ ID NOs: 25, 28-33, 36; wherein the variant PDGF binding peptide substantially retains the ability to bind PDGF.

In one embodiment, the presently disclosed subject matter provides growth differentiation factor (GDF) binding peptides previously published in US Patent Application Publication No. US 2009/0098175 A1 comprising a sequence set forth in SEQ ID NOs: 40-43, conservatively substituted variants of SEQ ID NOs: 40-42, variants having at least 70% sequence identity to SEQ ID NOs: 40-42, wherein the variant GDF binding peptide substantially retains the ability to bind GDF.

In one embodiment, the binding peptides comprise one or more modifications to the N-terminus, peptide C-terminus, or within the peptide amino acid sequence. In one embodiment the modification is selected from the group consisting of aldehyde group, hydroxyl group, thiol group, amino group, amino acids, lysine, cysteine, acetyl group, polymers, synthetic polymers, polyethers, poly(ethylene glycol) ("PEG"), an 11 unit polyethylene glycol ("PEG10"), and a 1 unit polyethylene glycol ("mini-PEG" or "MP"), and combinations thereof.

In one embodiment, the presently disclosed subject matter provides an implantable device for tissue repair comprising a polymer having a covalently attached binding peptide. In one embodiment, the binding peptide is a cell binding peptide that binds one or more of stem cells, fibroblasts, or endothelia cells. In one embodiment the binding peptide is a cell binding peptide and one or more growth factor binding peptides. In one embodiment, the binding peptide is a growth factor binding peptide. In one embodiment, the growth factor binding peptide is a PDGF binding peptide or a GDF binding peptide. In one embodiment, the tissue for repair comprises any one or more of tendon, muscle, connective tissue, ligament, cardiac tissue, vascular tissue, or dermis.

In one embodiment, the implantable device comprising the polymer is selected from the group consisting of a gel, a hydrogel, an injectable material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft or mesh for breast reconstruction, a composite surgical mesh comprising a synthetic polymer and a biopolymer, and derivatives and combinations thereof. In one embodiment, the polymer is a biopolymer selected from the group consisting of a collagen, an injectable collagen, a keratin, a silk, a polysaccharide, a dextran, an agarose, a cellulose derivative, an oxidized cellulose, an oxidized regenerated cellulose, a carboxymethylcellulose, a hydroxypropylmethylcellulose, a chitosan, a chitin, a hyaluronic acid, and derivatives and combinations thereof. In one embodiment, the polymer is a synthetic polymer selected from the group consisting of polymaleic anhydride having molecular weight of about 5,000 Dalton or less and a block co-polymer of polymaleic anhydride having molecular weight of about 5,000 Dalton or less and a co-polymer comprising a biodegradable functionality, wherein the co-polymer is selected from the group consisting of polylactic acid, polyglycolic acid, polylactic-co-glycolic acid, polycaprolactone, poly-3-hydroxybutyrate, poly(p-dioxanone) and copolymers thereof, polyhydroxyalkanoate, poly(propylene fumarate), poly(ortho esters), and polyanhydrides, and combinations thereof. In one embodiment, the binding peptide is attached to the polymer with or without a spacer.

In one embodiment, the presently disclosed subject matter provides a method for tissue repair comprising delivering to a subject an implantable device for tissue repair, wherein the implantable device comprises a polymer having a covalently attached binding peptide, wherein the implantable device serves as a scaffold for tissue repair. In one embodiment, the tissue for repair comprises any one or more of tendon, muscle, connective tissue, ligament, cardiac tissue, vascular tissue, or dermis. In one embodiment, the binding peptide is a cell binding peptide that binds one or more of stem cells, fibroblasts, or endothelial cells. In one embodiment the binding peptide is a cell binding peptide and one or more growth factor binding peptides. In one embodiment, the binding peptide is a growth factor binding peptide. In one embodiment, the growth factor binding peptide is a PDGF binding peptide or a GDF binding peptide.

In one embodiment, the presently disclosed subject matter provides a method for capturing cells onto an implantable device for tissue repair comprising contacting a sample comprising cells with the implantable device, wherein the implantable device comprises a polymer having a covalently attached cell binding peptide, and wherein the cells comprised in the sample are captured onto the implantable device through binding to the attached cell binding peptide. In one embodiment, the binding peptide is a cell binding peptide that binds one or more of stem cells, fibroblasts, or endothelia cells. In one embodiment, the sample comprising cells comprises allogeneic stem cells, bone marrow, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof. In one embodiment, the polymer further comprises an attached growth factor binding peptide and the sample comprising cells comprises a growth factor, wherein the growth factor comprised in the sample is captured onto the implantable device through binding to the attached growth factor binding peptide.

A method for tissue repair comprising contacting a sample comprising cells with an implantable device comprising a polymer having a covalently attached cell binding peptide, wherein the cells comprised in the sample are captured onto the implantable device through binding to the attached cell binding peptide, and delivering to a subject the implantable device for tissue repair. In one embodiment, the tissue for repair comprises any one or more of tendon, muscle, connective tissue, ligament, cardiac tissue, vascular tissue, or dermis. In one embodiment, the cell binding peptide binds one or more of stem cells, fibroblasts, or endothelia cells. In one embodiment, the sample comprising cells comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof. In one embodiment, the polymer further comprises an attached growth factor binding peptide and the sample comprising cells comprises a growth factor, wherein the growth factor comprised in the sample is captured onto the implantable device through binding to the attached growth factor binding peptide.

A method for capturing growth factors onto an implantable device for tissue repair comprising contacting a sample comprising growth factors with the implantable device, wherein the implantable device comprises a polymer having one or more covalently attached growth factor binding peptides, wherein the growth factor binding peptide is a PDGF binding peptide or a GDF binding peptide, and wherein the growth factor comprised in the sample is captured onto the implantable device through binding to the attached growth factor binding peptide. In one embodiment, the sample comprising growth factor comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof.

A method for tissue repair comprising contacting a sample comprising growth factor with an implantable device comprising a polymer having one or more covalently attached growth factor binding peptides, wherein the growth factor binding peptide is a PDGF binding peptide or a GDF binding peptide, wherein the growth factor comprised in the sample is captured onto the implantable device through binding to the attached growth factor binding peptide, and delivering to a subject the implantable device for tissue repair. In one embodiment, the tissue for repair comprises any one or more of tendon, muscle, connective tissue, ligament, cardiac tissue, vascular tissue, or dermis. In one embodiment, the sample comprising growth factor comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, recombinant GDF, recombinant PDGF, or a homogeneous or heterogeneous population of cultured cells, or combinations or derivatives thereof.

The following examples are provided to further describe certain aspects of the presently disclosed subject matter and are not intended to limit the scope of the presently disclosed subject matter.

EXAMPLES

Example 1

Identification of Cell Binding Peptides by Phage Display

Peptides that bind human mesenchymal stem cells (MSCs) were identified by phage display biopanning. MSCs were culture amplified from plated bone marrow aspirate (LONZA, <4 passages). After biopanning, individual plaques were picked, grown overnight, and tested for MSC binding activity using flow cytometry according to the following procedure. Phage supernatant was incubated with MSCs for 30 min on ice. Cells were washed twice with Dulbecco's Phosphate Buffered Saline (DPBS) containing 2% FBS, then incubated with 50 ul of anti-M13 antibody labeled with the fluorophore phycoerythrin (PE). After 30 minutes on ice, cells were washed twice with DPBS containing 2% FBS and binding data acquired on a BD FACSARRAY flow cytometer. For the phage displaying MSC binding activity, DNA sequences were analyzed and translated into peptide sequences using Vector NTI DNA Analysis software (see FIG. 14 and Table 1; SEQ ID NOs: 1-15).

TABLE 1

Stem Cell Binding Peptides

| SEQ ID NO: | Amino acid sequence (single letter code) |
|---|---|
| 1 | SSMYFSPLHTWQSAPSTSGAE |
| 2 | SSFRFQRLEDWNYPSNTDNAE |
| 3 | SSGYMQFGHLLDWTGSPSGSR |
| 4 | SSFWDVCQGDGTCYGGGSR |
| 5 | VANPFTYLSAWSNPL |
| 6 | ETLIFSKLGQWGNSLS |
| 7 | GYMQFGHLLDWTGSP |
| 8 | SVYRFDSLTTWSSNQ |
| 9 | GSWSFGTLGPWSSSQ |
| 10 | WLGNFNALTDWPTDS |
| 11 | TSGFFGSLDTWPPTL |
| 12 | NYWNFGPLEDYS |
| 13 | SVLHFHPMKSYD |
| 14 | NSIYFSPLRDYQ |
| 15 | GHFEYGRLQSIL |

In addition to the cell binding sequences in Table 1 above, a consensus stem cell binding sequence was designed based on the sequences for the stem cell binders shown in FIG. 14. Specifically, the following sequence: SSFRFGPLGTWNYP-STDNAE (SEQ ID NO: 16) was designed based on sequences in FIG. 14 (SEQ ID NOs: 5-15) which showed a high level of stem cell binding activity, and the observation that non-binding sequences contain a larger number of negatively charged residues in the amino and carboxyl terminal regions, and a larger number of positively charged residues in the central region, than the sequences showing stem cell binding activity.

In addition to consensus cell binding sequence (SEQ ID NO: 16), the following sequence motifs SEQ ID NOs: 17-18 were generated based on the stem cell binding activity observed for the peptide sequences in Table 1 and FIG. 14:

SEQ ID NO: 17:
$X_1X_2FX_4X_5LX_7X_8WX_{10}X_{11}X_{12}X_{13}X_{14}$, wherein "$X_1$" is F, M, L, Y, W, or N; wherein "$X_2$" is R, Q, P, I, Y or S; wherein "$X_4$" is G, S, Q, T, or D; wherein "$X_5$" is P, R, Y, K, H, or S; wherein "$X_7$" is G, H, E, S, L, or T; wherein "$X_8$" is T, D, A, Q, or P; wherein "$X_{10}$" is N, Q, S, G, or T; wherein "$X_{11}$" is Y, S, N, or G; wherein "$X_{12}$" is P, A, S, or N; wherein "$X_{13}$" is S, P, L, or Q; and wherein "$X_{14}$" is T, S, or N.

SEQ ID NO: 18:
$X_1X_2X_3X_4X_5X_6X_7X_8X_9X_{10}X_{11}X_{12}X_{13}X_{14}$, wherein "$X_1$" is F, W, L, Y, M, or I; wherein "$X_2$" is N, Y, R, P, Q, I, F, or E; wherein "$X_3$" is F or Y; wherein "$X_4$" is G, S, T, Q, N, H, or D; wherein "$X_5$" P, R, Y, T, S, K, H, or A; wherein "$X_6$" is L or M; wherein "$X_7$" is T, G, E, S, R, Q, L, K, H, or D; wherein "$X_8$" is D, T, S, Q, P, or A; wherein "$X_9$"

is W, Y, or I; wherein "$X_{10}$" is P, N, Q, S, G, L, D, or T; wherein "$X_{11}$" is Y, S, N, T, P, or G; wherein "$X_{12}$" is P, A, S, T, D, or N; wherein "$X_{13}$" is S, P, L, or Q; and wherein "$X_{14}$" is S or N.

Mutagenesis of Cell Binding Peptide Sequence SEQ ID NO: 4.

A focused phage display library was generated around the SEQ ID NO: 4 sequence with each nucleotide position varying in identity at a ratio of 91:3:3:3, with the original nucleotide being the dominant form. This is considered a form of "light" mutagenesis, retaining the majority of residue identities with a few amino acid identity changes. The construction of this "degenerate" phage library was performed according to the methods described in Kay et al., 1996. Individual phage were picked from the degenerate phage library and binding to MSCs was assessed by flow cytometry as described herein above. Forty eight phage "binders" (binding comparable to wild type SEQ ID NO: 4) and 48 phage "non-binders" (phage binding reduced to level of a control without a polypeptide insert) were re-amplified, retested, and submitted for DNA sequencing to determine the insert amino acid sequences.

Based on these results, the following first cell binding sequence motif was generated:

SEQ ID NO: 19:
$X_1$-$Z_2$-$Z_3$-$X_4$-$X_5$-C-$X_7$-$X_8$-$X_9$-G-T-C-$X_{13}$-G-G-G, wherein "$X_1$" is S, N, T, I, V, or G; wherein "$Z_2$" and "$Z_3$" are F, W, or Y; wherein "$X_4$" is D, E, W, N, Q, or G; wherein "$X_5$" is V, M, or A; wherein "X," is Q, P, E, L, H, R, or A; wherein "$X_8$" is G, A, V, or R; wherein "$X_9$" is D, N, or E; and wherein "$X_{13}$" is Y, W, or H.

Further, based on these results, the following second cell binding sequence motif was generated:

SEQ ID NO: 20:
$X_1$-$X_2$-W-$X_4$-$X_5$-C-$X_7$-$X_8$-$X_9$-G-T-C-$X_{13}$-G-G-G, wherein "$X_1$" is S, N, T, I, V, or G; wherein "$X_2$" is F or Y; wherein "$X_4$" is D, E, W, N, Q, or G; wherein "$X_5$" is V, M, or A; wherein "X," is Q, P, E, L, H, R, or A; wherein "$X_8$" is G, A, V, or R; wherein "$X_9$" is D, N, or E; and wherein "$X_{13}$" is Y, W, or H.

Example 2

Generation of Synthetic Binding Peptides

Peptide Synthesis.

Binding peptide sequences were synthesized using standard solid-phase peptide synthesis techniques on a SYMPHONY Peptide Synthesizer (PROTEIN TECHNOLOGIES, Tucson, Ariz.) using standard Fmoc chemistry (HBTU/HOBT activation, 20% piperidine in DMF for Fmoc removal). N-α-Fmoc-amino acids (with orthogonal side chain protecting groups; NOVABIOCHEM). After all residues were coupled, simultaneous cleavage and side chain deprotection was achieved by treatment with a trifluoroacetic acid (TFA) cocktail. Crude peptide was precipitated with cold diethyl ether and purified by high-performance liquid chromatography on a WATERS Analytical/Semi-preparative HPLC unit on VYDAC C18 silica column (preparative 10 μm, 250 mm×22 mm) using a linear gradient of water/acetonitrile containing 0.1% TFA. Homogeneity of the synthetic peptides was evaluated by analytical RP-HPLC (VYDAC C18 silica column, 10 μm, 250 mm×4.6 mm) and the identity of the peptides confirmed with MALDI-TOF-MS. Biotinylated peptides were generated similarly, with a GSSGK(biotin) sequence or other spacer group added to the C-terminus of the peptide.

Example 3

Cell Binding Peptide Specificity

The synthetic biotinylated cell binding peptide SEQ ID NO: 4 was examined for its ability to specifically bind MSCs compared to a number of other cells types including adipose-derived mesenchymal stem cells (ASCs), dermal fibroblasts, rodent MSCs, red blood cells, monocytes, lymphocytes and granulocytes. The cell binding peptide was biotinylated as described herein at Example 2. Cultured cells of each type were either purchased (ASCs and dermal fibroblasts) or isolated from rodent bone marrow (rodent MSCs) or human blood. Cells were first harvested and resuspended at $10^6$/mL in PBS+2% fetal bovine serum (FBS). An aliquot of cells (50 μL) was incubated in 50 μL of peptide solution (25 μM in PBS+FBS) for 30 min at 4° C. Cells were then washed twice in PBS+FBS with 300×g centrifugation for 5 min between washes. Fluorescently-tagged neutravidin (Neutravidin-PE from INVITROGEN) was then added to the cells to label biotinylated peptide bound to cells. Neutravidin-PE was diluted 1:250 from stock and applied at 50 μL to cells. Cells were then washed in PBS+FBS, and acquired on a BD FACSARRAY. Peptide reactivity was then measured as percent positively relative to Neutravidin-PE staining without the addition of biotinylated peptide. Cell binding peptide SEQ ID NO: 4 was observed to have high binding to human MSCs, human ASCs and dermal fibroblasts (see FIG. 15).

The synthetic biotinylated binding peptide SEQ ID NO: 4 was further examined for its ability to bind endothelial cells compared to other cell types (see FIG. 16). Biotinylated cell binding peptide SEQ ID NO: 4 (10 μM) was incubated with 25,000 cultured cells (human umbilical vein endothelial cells (HUVECs), endothelial colony forming cells (ECFCs; LONZA), umbilical artery smooth muscle cells (UASMCs) or whole blood cells from freshly collected human blood for 30 min at 4° C. Cells were washed twice and cell-bound peptide was detected with Neutravidin-PE (INVITROGEN) for 30 min at 4° C. Cells were then washed, resuspended and fixed in 2% paraformaldehyde, and acquired on a BD FACSARRAY. The data in FIGS. 16A & 16B show that SEQ ID NO: 4 cross-reacted strongly with ECFCs and HUVECs, weakly with UASMCs, and had no cross-reactivity with peripheral blood cells. ECFCs are clonally expanded cells isolated from human umbilical cord blood, and are considered highly proliferative endothelial progenitor cells (EPCs) based on their clonogenic and proliferative potential. In another experiment, binding peptide SEQ ID NO: 4 was assayed for its ability to selectively isolate endothelial cells versus smooth muscle cells in the presence of whole blood. HUVECs or UASMCs were incubated in the presence of medium containing 20% whole blood and binding peptide SEQ ID NO: 4-conjugated magnetic beads (via biotin-SA) for 30 min. The solutions containing the bead-peptide-cell complexes were then passed through a MILTENYI LS column in a magnetic field. The column was washed, and the remaining peptide-bound cells were then released from the magnetic field and counted. The data in FIG. 16C show that binding peptide SEQ ID NO: 4 isolated 8-fold more HUVECs compared to UASMCs.

Example 4

Capture of Cultured MSCs with Cell Binding
Peptide Attached to a Substrate

Figure 17:
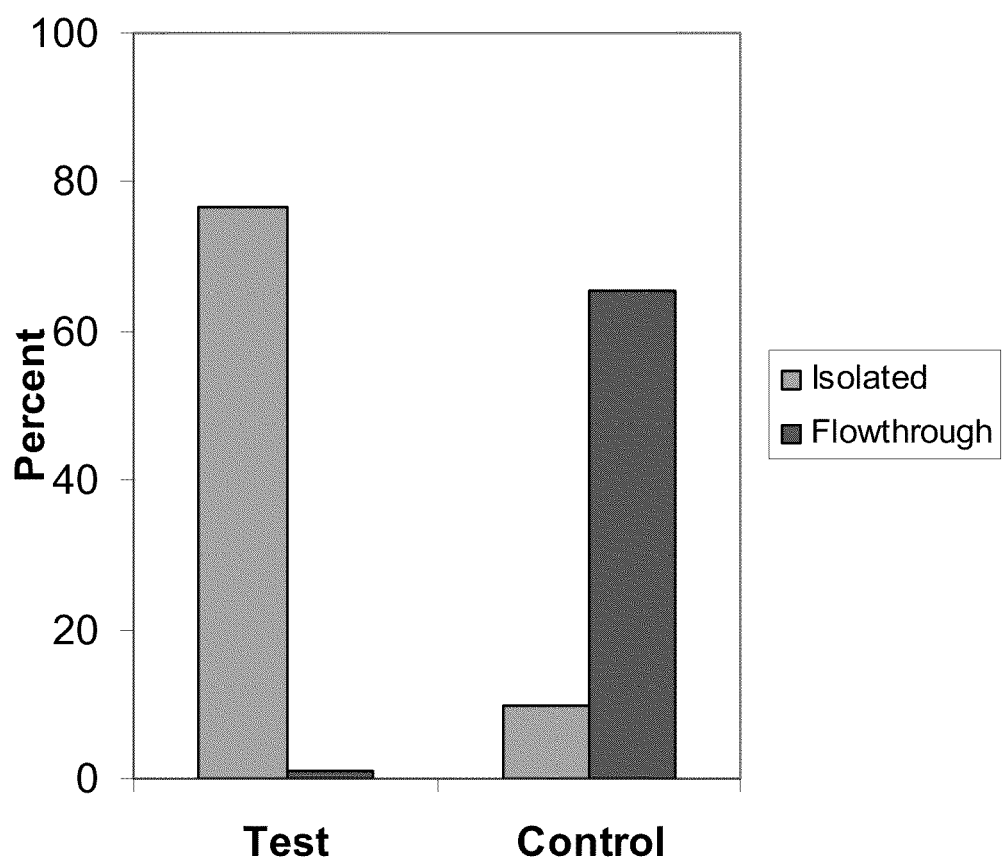
FIG. 17 is a bar graph showing the ability of biotinylated stem cell binding peptide SEQ ID NO: 4 ("test") to capture human MSCs from a homogeneous cultured cell population relative to a non-binding control peptide ("control"). The capture of MSCs bound to biotinylated peptide was performed with MILTENYI BIOTEC Streptavidin microbeads loaded into LS columns.

In this experiment the ability of the biotinylated cell binding peptide SEQ ID NO: 4 to capture human MSCs from a homogeneous cultured cell population was examined. The cell binding peptide SEQ ID NO: 4 was biotinylated as described herein at Example 2. The cell binding peptide SEQ ID NO: 4, and a non-binding control peptide, were added to separate 300 µl volumes of MILTENYI BIOTEC Streptavidin microbeads at a concentration of 20 µM. These beads are made from iron filings, coated with a dextran coating which is functionalized with streptavidin moieties. Peptide was incubated with beads for 45 min on ice. The 300 µl of peptide coated microbeads were added to pre-equilibrated LS columns outside of the magnetic field to evenly distribute the magnetic beads throughout the columns. Columns were then placed into a magnetic field, and excess peptide was washed away with buffer while retaining the peptide coated microbeads. Cultured and expanded human MSCs from bone marrow aspirate (160,000 cells; LONZA) were added to each LS column and allowed to pass through by gravity flow. Flowthrough was collected and cycled through the columns 5 times, after which the columns were washed with 5 ml buffer. Bound cells were eluted by removing columns from the magnetic field and flushing with 5 ml buffer into 15 ml conical tubes. The collected flowthrough with 5 ml wash and eluted cells were spun down, resuspended in a smaller volume, and counted by hemacytometer (see FIG. 17). The data in FIG. 17 show capture of approximately 70% of the MSCs by the cell binding peptide SEQ ID NO: 4 compared to only about 10% capture by the control peptide.

Example 5

Figures 18A, 18B, 18C:
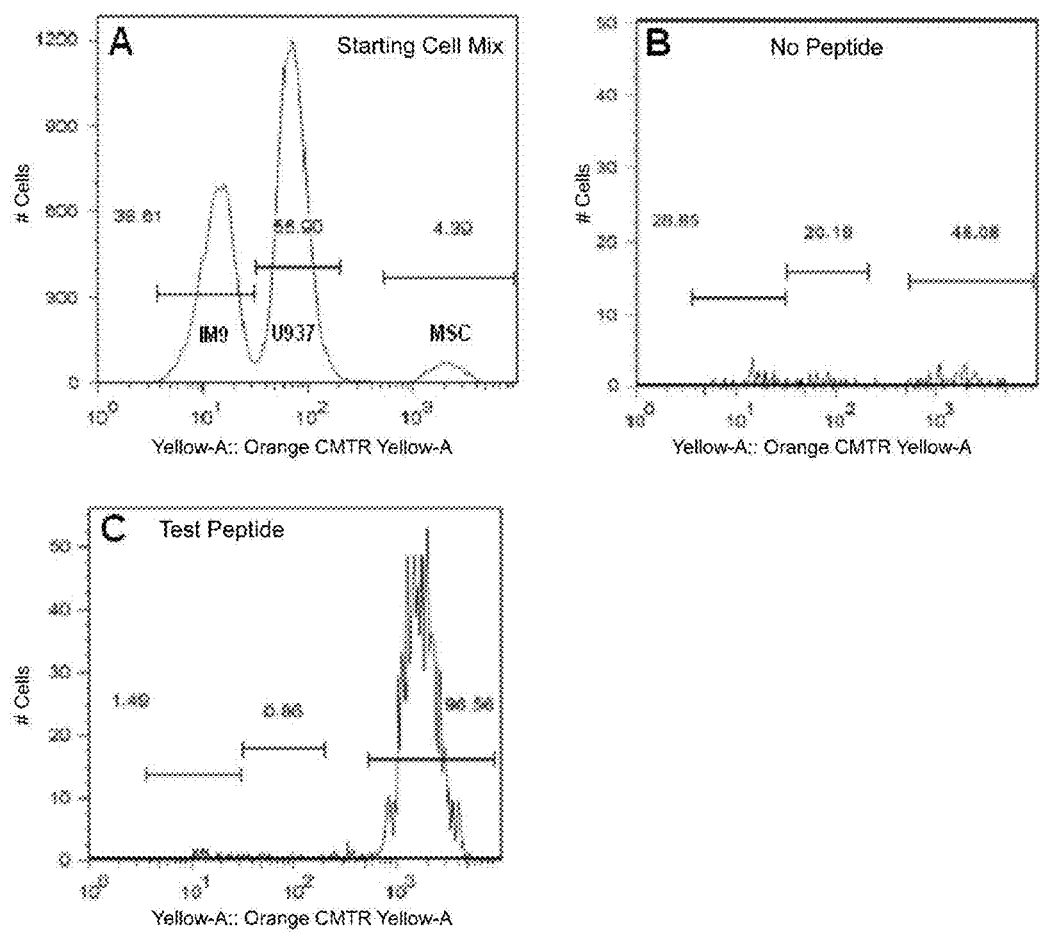
FIGS. 18A-18C are flow cytometry histograms of cells showing selective capture of MSCs on biotinylated stem cell binding peptide SEQ ID NO: 16 ("test"; panel C) attached to CELLECTION magnetic beads. The CELLECTION beads have streptavidin coupled to a magnetic particle through a DNA linker. Three different cell types, human MSCs, IM-9, and U937 cells were differentially labeled with CELLTRACKER dye and mixed in a ratio such that the MSCs represented ~4% of the starting cell mixture (the percentage of each cell type in the starting mixture was 38% IM9, 56% U937, and 4% MSC (panel A). Panel B is a no peptide control.

Capture of MSCs from a Mixed Cell Population with
Cell Binding Peptide Attached to a Substrate In this experiment, biotinylated cell binding peptide, SEQ ID NO: 16, was attached to CELLECTION magnetic beads. The CELLECTION beads have streptavidin coupled to a magnetic particle through a DNA linker. Three different cell types, human MSCs, IM-9, and U937 cells were differentially labeled with CELLTRACKER dye and mixed in a ratio such that the MSCs represented ~4% of the starting cell mixture (the percentage of each cell type in the starting mixture was 38% IM9, 56% U937, and 4% MSC). The cell binding peptide, SEQ ID NO: 16, was biotinylated as described herein at Example 2, as was a general cell binding peptide for use as a control peptide in the experiment. Magnetic particles with no peptide attached, as well as magnetic beads having attached either the cell binding peptide, SEQ ID NO: 16, or the control peptide were tested for their ability to capture human MSCs. The starting cell mixture was incubated with magnetic beads having either attached peptide or no peptide, the beads were washed, and the captured cells were released from the beads by DNase treatment. The cells were measured by flow cytometry histograms shown in 18A-18C. The starting cell mixture is shown in FIG. 18A. The magnetic beads without peptide captured little or no cells (FIG. 18B). The magnetic beads with attached cell binding peptide SEQ ID NO: 16 captured a cell population that was 96% MSCs (FIG. 18C).

Example 6

Figure 19:
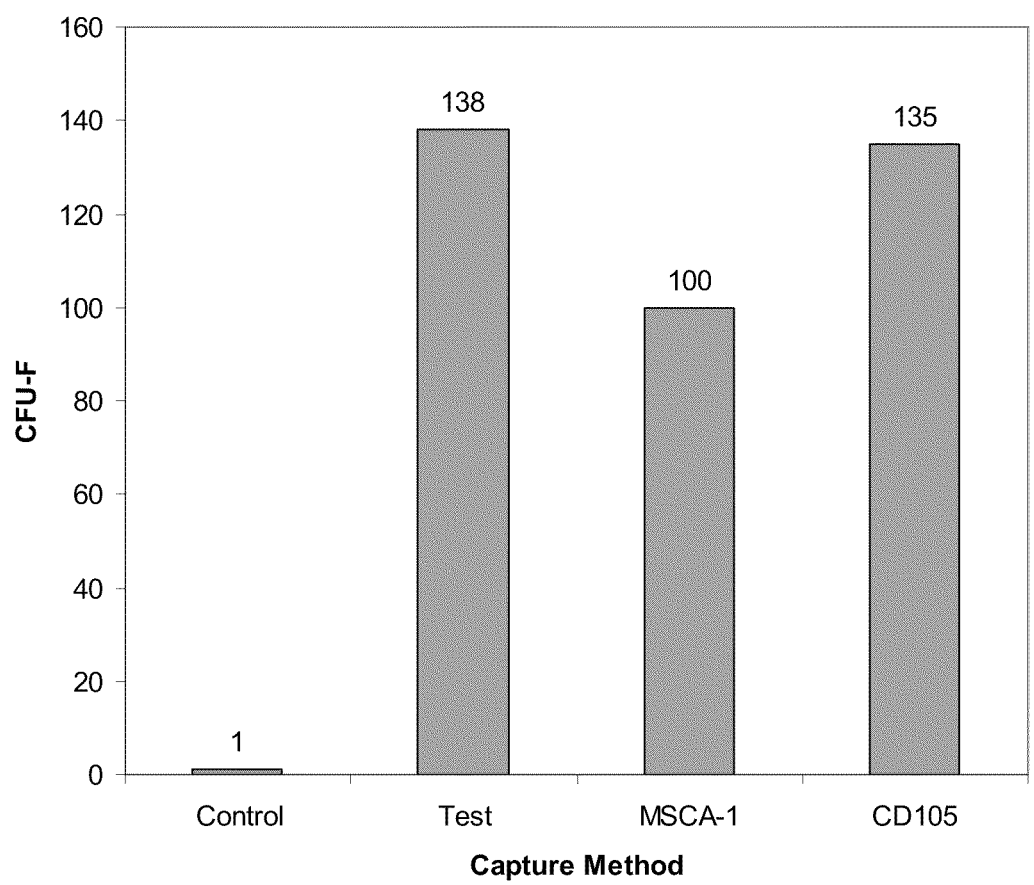
FIG. 19 is a bar graph showing the ability of biotinylated stem cell binding peptide SEQ ID NO: 4 ("test") to capture human MSCs directly from bone marrow aspirate in comparison to a negative peptide control and to two separate antibodies against the CD105 stem cell antigen (CD105) and the MSCA-1 stem cell antigen (MSCA-1), respectively. The capture of MSCs bound to biotinylated peptide was performed with MILTENYI BIOTEC Streptavidin microbeads loaded into LS columns. The y axis shows colony forming units (CFUs) counted after 14 days in culture.

Capture of MSCs from Bone Marrow Aspirate with
Cell Binding Peptide Attached to a Substrate This experiment was performed to examine the ability of cell binding peptide SEQ ID NO: 4 to capture MSCs directly from bone marrow aspirate in comparison to two separate antibodies against the CD105 I antigen (CD105) and the MSCA-1 stem cell antigen (MSCA-1). This experiment employed biotinylated peptides with streptavidin-coated MILTENYI magnetic beads. The peptides were biotinylated as described herein at Example 2. In addition to cell binding peptide SEQ ID NO: 4, a negative control peptide that does not bind to MSCs was included in the experiment. For the antibody capture experiment, magnetic beads having covalently attached CD105 or MSCA-1 antibody were employed (MILTENYI). Prior to incubation with the peptides and antibodies, bone marrow aspirate (BMA) was mixed with 5 volumes of 10 mM ammonium chloride for 1-2 min at room temperature to lyse red blood cells. The lysate was centrifuged for 5 min at 300×g and the supernatant discarded. The cell pellet was washed with wash buffer (PBS+0.5% bovine serum albumin+0.5 mM EDTA) and cells were resuspended in 25 mM peptide at a concentration of $10^8$ per mL. For peptide binding studies, the cell suspension was incubated with the biotinylated peptides for 30 min at 4° C. to allow for binding. After incubation, cells were spun down at 300×g for 5 min, and peptide solution was aspirated. Cells were then rinsed twice with wash buffer, with centrifugation between washes. Cells were resuspended in 80 µL of wash buffer per $10^7$ cells. Streptavidin-coated beads were then added at 20 µL per 80 µL of cells. The following procedure was performed for the cell binding experiment with the CD105 and MSCA-1 antibodies. First, 20 µL of magnetic beads having attached CD105 or MSCA-1 antibody were added to 80 µL of the resuspended cells. Bead and cell mixtures were then incubated for 20 min at 4° C. The mixtures were centrifuged to pellet the cells, and the cells were washed once to remove unbound beads. The cell pellet was then resuspended in 1 mL of wash buffer, and loaded into an equilibrated LS purification column attached to a MIDIMACS separator (MILTENYI). The separator contains a magnet, which causes the magnetic beads to adhere to the column, while unbound materials flow through the column. Column was then washed three times with 3 mL of wash buffer. Column was then removed from the magnet, and cell-bound beads were eluted by flushing the column with 5 mL of wash buffer in a clean 15 mL conical tube. The eluants were then plated and cultured. Colony forming units (CFUs) were counted after 14 days in culture. The results are shown in FIG. 19. MSC capture by stem cell binding peptide SEQ ID NO: 4 is as efficient as capture by either of the CD105 or MSCA-1 antibodies (FIG. 19). In contrast, no MSC capture was observed with the negative peptide control. Cells captured with this method were also examined for immunoreactivity for a number of antigens. When comparing stem cell binding peptide SEQ ID NO: 4 and CD105 isolated cells, no changes were observed for immunoreactivity for a number of antibodies including: CD29(±), CD44(+), CD73(+), CD105(+), CD166(+), CD90(+), CD45(−), and CD34 (−). These data suggest that stem cell binding peptide SEQ ID NO: 4 is capable of isolating an MSC cell population that is phenotypically similar to cells isolated by CD105 isolation.

Example 7

Covalent Attachment of Cell Binding Peptide to Collagen Substrate

Cell binding peptide SEQ ID NO: 4 was covalently attached to a collagen substrate using p-nitrophenyl chloroformate chemistry (see FIG. 1). HELISTAT collagen sponge (INTEGRA LIFE SCIENCES, Plainsboro, N.J.) was used as the collagen substrate. The cell binding peptide SEQ ID NO: 4 was modified at the carboxyl terminus with a PEG-10 spacer and a lysine residue.

Collagen Sponge Substrate Modification.

HELISTAT collagen (15 sponges, 21.6 mg) was placed in a peptide reactor vessel flushed with nitrogen. The amount of surface amines on the collagen was estimated at ~35 µmol/g based on quantitative ninhydrin assay. The vessel was charged with 10 mL anhydrous acetonitrile and DIEA (50 µL). Excess (100-fold) p-nitrophenylchloroformate (35 mg, 173 µmol) was added to the vessel and flushed with nitrogen. The reaction vessel was shaken for 4 h on a vortexer (low setting). The reaction mixture was filtered and the sponges were washed thoroughly with 10 mL of DCM, anhydrous (3×) with shaking and then dried under nitrogen. Based on quantitative ninhydrin assay, the majority of surface amines were consumed during this step. This was also confirmed by hydrolyzing a collagen sponge sample with 0.1N NaOH at 22° C. for 15 min to release the nitrophenylate ions, which were quantified spectrophotometrically at 405 nm ($\epsilon=1.7\times 10^4 M^{-1} cm^{-1}$). The collagen-pNP sponges were then reacted directly with peptide.

Peptide Coupling.

Cell binding peptide SEQ ID NO: 4 (with PEG-10-Lys modification; 4 mg) was taken in 4 mL anhydrous acetonitrile and DMF mixture (1:1) in a polypropylene tube flushed with nitrogen. DIEA (50 µL) was added to bring the pH to ~9. The collagen-pNP (11 sponges; 15.8 mg) was added to the peptide solution. The reactor was flushed with nitrogen and vortexed overnight. The yellow reaction solution was carefully collected and the sponges were thoroughly washed with anhydrous acetonitrile. The washes were carefully pooled. The sponges were flushed and dried under nitrogen. The extent of peptide loading was determined spectrophotometrically at 405 nm by quantifying the p-nitrophenylate ion displaced by the peptide. The peptide loading was determined to be 28.48 µmol peptide/g of collagen.

Soluble Collagen Substrate Modification.

In another experiment, cell binding peptide SEQ ID NO: 4 was covalently attached to a soluble collagen substrate using homobifunctional N-hydroxysuccinimide ester, $BS^3$ crosslinking reagent (THERMO SCIENTIFIC, Rockford, Ill.) (the chemistry is depicted in FIG. 3). First the peptide having a spacer and lysine residue at the carboxyl terminus was reacted with the $BS^3$ crosslinking reagent and the complex purified by HPLC. An excess of $BS^3$ was used to minimize peptide dimerization. The activated peptide was then added to soluble bovine, type I collagen (BD BIOSCIENCES, San Jose, Calif.) in a phosphate buffer (pH=8) resulting in conjugation to collagen via lysine amino groups on collagen. The reaction resulted in 80-90% of the peptide-$BS^3$ complexes coupled to the collagen.

Fibrillar Collagen Substrate Modification.

In another experiment, cell binding peptide SEQ ID NO: 4 is covalently attached to a fibrillar collagen substrate using homobifunctional N-hydroxysuccinimide ester, $BS^3$ crosslinking reagent (THERMO SCIENTIFIC, Rockford, Ill.) (the chemistry is depicted in FIG. 3). First, the peptide having a spacer and a lysine residue at the C-terminus is reacted with $BS^3$, and the resulting complex is purified by HPLC. An excess of $BS^3$ is used to minimize peptide dimerization. The $BS^3$-activated peptide is conjugated to fibrillar collagen in PBS buffer by addition of approximately 20 µmol peptide per gram of matrix. After washing and freeze-drying the material the peptide loading efficiency is evaluated, for example, by trypsin assay. Briefly, the tissues are placed in trypsin digestion buffer (50 mM Tris-HCl, 0.15 mM NaCl, 10 mM $CaCl_2$, pH 7.5) containing 10 µg/mL trypsin for 18 h at 37° C. resulting in cleavage of the peptide and release of a peptide fragment into the supernatant. An HPLC assay is used to measure the amount of peptide fragment released using a standard curve generated from trypsin digestion of unconjugated peptide.

Example 8

Covalent Attachment of Cell Binding Peptide to Decellularized Tissue Substrates Acellular Collagen-Rich Graft Substrate Modification.

Cell binding peptide SEQ ID NO: 4 was covalently attached to a variety of acellular collagen-rich graft substrates including decellularized porcine dermis as a biological cell-binding matrix for soft tissue and abdominal wall reconstruction.

Decellularization of Rat Arterial Tissue.

One use for an acellular artery substrate having a covalently attached cell binding peptide is for vascular repair as there remains an unmet need to reduce intimal hyperplasia and thrombosis in small- to medium-caliber prosthetic vascular grafts. For example, ePTFE, which is commonly used for small caliber arteries (≤6 mm), has a high incidence of failure due to intimal hyperplasia and ongoing surface thrombogenicity (Chlupac et al., Physiol Res, 2009, 58 Suppl 2:S119-39; Zilla et al., Biomaterials, 2007, 28:5009-27). The absence of a selectively permeable and thrombo-resistant endothelium is the main reason for the failure of medium to small-caliber prosthetic vascular grafts (Zhang et al., J Cell Mol Med, 2007, 11:945-57). Ingrowth of a vascular graft from neighboring endothelial cells (EC), and colonization of circulating endothelial progenitor cells (EPC) have resulted in endothelialization of vascular grafts in animal models (Zilla et al., Biomaterials, 2007, 28:5009-27; Shi et al., *Blood*, 1998, p. 362-67). Successful pre-clinical studies have not translated to the clinic in localizing these cell types to grafts to generate a non-thrombotic surface (Walter et al., *Circulation*, 2002, p. 3017-24; Werner et al., *Circ Res*. 2003, p. e17-24; Bhattacharya et al., in *Blood*, 2000, p. 581-5; Kaushal et al., in *Nat. Med.* 2001, p. 1035-40; Griese et al., in *Circulation*, 2003, p. 2710-5). Positive preclinical and clinical studies involving the seeding of cells at the luminal surface of prosthetic vascular grafts prior to implantation supports the concept that ECs and EPCs can improve functional outcomes in vivo (Bhattacharya et al., in *Blood*. 2000. p. 581-5; Deutsch et al., Surgery, 1999, 126:847-55; Meinhart et al., in *Ann Thorac Surg.* 2001. p. S327-31; Zilla et al., in *J Vasc Surg.* 1994. p. 540-8; Parikh, S. A. and E. R. Edelman, Adv Drug Deliv Rev, 2000, 42:139-61). Alternatively, mobilizing EPCs from bone marrow followed by capture of EPCs on a vascular graft represents an exciting alternative that eliminates most of the complications associated with cell seeding, and is currently being explored in the clinic with bare metal stents (Aoki et al., J Am Coll Cardiol, 2005, 45:1574-9). In animal models, small numbers of circulating EPCs have been shown to passively attach to implanted grafts and decrease neointima formation following vascular injury (Walter et al., in *Circulation*. 2002. p. 3017-24; Werner et al., in *Circ Res*. 2003. p. e17-24). Therefore, in the present experiment an acellular artery having a covalently attached endothelial cell binding peptide is generated as a small-caliber vascular graft to promote ingrowth of endothelial cells onto the graft and to capture circulating endothelial progenitor cells (EPCs) to promote endothelialization of the graft. In this experiment, rat arteries are isolated and decellularized using methods based on published procedures. For example, rats are treated with heparin (100 units/kg) and the femoral arteries, approximately 2 cm in length, are placed in sterile distilled water for about 1 h to lyse red blood cells. The graft is washed PBS. The artery is decellularized in saline containing 1% Triton 100× and 0.1% ammonium hydroxide for about 24-48 hours at 4° C. on a mechanical rotator. If necessary, the luminal surface is exposed to shear flow in the decellularizing buffer for about 1-3 hours to completely remove cellular debris. Following this procedure the grafts are placed in PBS for about 24 hours at 4° C. on a mechanical rotator, changing the buffer at least 5 times.

Peptide Attachment to Rat Arterial Tissue.

In this experiment, cell binding peptide SEQ ID NO: 4 is covalently attached to the decellularized rat artery tissue using the $BS^3$ reagent described herein above for peptide covalent attachment to soluble collagen. After purification by HPLC, the peptide-$BS^3$ complex is added to the decellularized arteries in phosphate buffer pH 8.0 for about 24 h at 4° C. on a mechanical rotator. The arteries are washed in buffer and stored a 4° C. Approximately 20 µmole peptide per gram tissue is used for the attachment chemistry and peptide loading efficiency is evaluated by trypsin assay. Briefly, the tissues are placed in trypsin digestion buffer (50 mM Tris-HCl, 0.15 mM NaCl, 10 mM $CaCl_2$, pH7.5) containing 10 µg/ml trypsin (SIGMA, MO) for about 1 h at 37° C. to yield free peptide for analysis by HPLC. Peptide concentration is determined from a standard curve generated with unconjugated peptide.

Decellularization of Porcine Dermal Tissue.

One use for an acellular porcine dermal graft substrate having a covalently attached cell binding peptide is for hernia repair as there remains an unmet need to reduce recurrence rates which can be achieved by accelerating post-operative healing. Wound breaking strength represents the amount of force a surgical wound can withstand before failing, and failure occurs when there is a deficient quantity and quality of tissue repair (Franz, M. G., Surg Clin North Am, 2008, 88:1-15, vii). Previous studies have suggested that wound repair integrity reaches a normal breaking strength in 30 days (Franz et al., J Surg Res, 2001, 97: 109-16; Robson, M. C., Surg Clin North Am, 2003, 83:557-69). Fibroblasts are responsible for collagen synthesis and deposition and recovery of wound breaking strength (Franz, M. G., Surg Clin North Am, 2008, 88:1-15, vii). Two days post surgery the inflammatory response subsides and fibroblasts infiltrate the wound, out numbering other cell types by day 4 (Dubay, D. A. and M. G. Franz, Surg Clin North Am, 2003, 83:463-81). Wounds are increasingly challenged during the recovery period as patients return to normal activity. The acellular collagen-rich graft substrate having a covalently attached cell binding peptide becomes populated with fibroblasts and vascularizes faster than other bioprosthetics, preventing infection and leaving a biologic repair. Reducing the recovery time by retaining fibroblasts at the surgical site will increase healing rates and improve repair outcomes. Porcine dermal tissue is decellularized using methods based on reports in the literature. For example, porcine skin is obtained from NAHUNTA PORK CENTER (Pikeville, N.C.) and half-thickness skin grafts are harvested using a dermatome (ROBBINS INSTRUMENTS, Chatham, N.J.). The grafts are cut in small squares and incubated for about 2 h at 4° C. in Hank's balanced salt solution (HBSS) containing 0.25% trypsin. The epidermal layer is peeled away and discarded and the dermal layer is rinsed multiple times in deionized water to reduce the salt content. To lyse cells, dermal tissues are incubated for about 1 h at RT in 0.5% sodium dodecyl sulfate (SDS), and rinsed multiple times in water. The tissue is incubated at RT for about 3 h in HBSS with gentle shaking to remove SDS and washed in water on a filter funnel. The tissue is freeze dried in a lyophilizer and stored at 4° C.

Peptide Attachment to Porcine Dermal Tissue.

In this experiment, cell binding peptide SEQ ID NO: 4 is covalently attached to the decellularized porcine dermal tissue using homobifunctional N-hydroxysuccinimide ester, $BS^3$ crosslinking reagent (THERMO SCIENTIFIC, Rockford, Ill.) (the chemistry is depicted in FIG. 3) for the attachment to soluble collagen. After purification by HPLC, the peptide-$BS^3$ complex is added to the decellularized dermis in phosphate buffer pH 8.0 for about 24 h at 4° C. on a mechanical rotator. The dermis is washed in buffer for about 1-2 h changing the buffer every 30 min, freeze dried, and stored at −20° C. Approximately 20 µmole peptide per gram tissue is used for the attachment chemistry and peptide loading efficiency is evaluated by trypsin assay. Briefly, the tissues are placed in trypsin digestion buffer (50 mM Tris-HCl, 0.15 mM NaCl, 10 mM $CaCl_2$, pH7.5) containing 10 µg/ml trypsin (SIGMA, MO) for about 1 h at 37° C. to yield free peptide that can be analyzed by HPLC. Peptide concentration is determined from a standard curve generated with unconjugated peptide.

Commercially Available Decellularized Tissues.

Cell binding peptide SEQ ID NO: 4 was covalently attached to two commercially available decellularized soft tissue matrices, PERMACOL (porcine dermis from TISSUE SCIENCE LABORATORIES, Aldershot, UK) and XENFORM (fetal bovine dermis from TEI BIOSCIEMCES, Boston, Mass.) using homobifunctional N-hydroxysuccinimide ester, $BS^3$ crosslinking reagent (THERMO SCIENTIFIC, Rockford, Ill.) (the chemistry is depicted in FIG. 3). Cell binding peptide SEQ ID NO: 4 was first modified with a spacer and lysine residue at the carboxyl terminus and activated with the $BS^3$ reagent. To 11 mg of decellularized soft tissue matrix (PERMACOL or XENFORM) was added $BS^3$-activated cell binding peptide (1.4 mg) in phosphate buffer (2.0 mL). The reaction mixture was agitated by shaking overnight at 4° C. followed by 3 h at room temperature. The peptide-matrix conjugate was isolated by vacuum filtration, washed with phosphate buffer (4×5 mL) and water (2×5 mL), and freeze dried. The samples were then subjected to trypsin digestion and analyzed using HPLC to estimate the amount of cell binding peptide covalently attached to the matrix. The amount of peptide covalently attached to the matrix ranged from 1-4 µmol peptide/g matrix.

In addition to the above experiment describing attachment of a cell binding peptide to acellular dermal matrices through the C-terminus of the peptide, cell binding peptide SEQ ID NO: 4 was also attached to the acellular matrices through the N-terminal amino group of the SEQ ID NO: 4 that also contained a C-terminal biotin group. By attaching the biotinylated peptide, the distribution of the peptide on the acellular dermal matrixes was demonstrated visually as follows. Small pieces of the acellular dermal matrix (PERMACOL or XENFORM) approximately 3 mm×3 mm were incubated in TBST buffer solution (10 mM Tris-HCL, 150 mM NaCl, 0.01% Tween-20, pH 8.0) to swell for 2 hours at room temperature.

The solution was discarded and replaced with TBST supplemented with 0.5% bovine serum albumin (TBST/BSA). This buffer was aspirated and replaced with a solution of 0.4 µg/ml neutravidin conjugated with horseradish peroxidase in TBST. The acellular dermis samples were mixed in this solution for 1 h at room temperature. The neutravidin-HRP solution was aspirated and samples were washed by mixing in TBST/BSA for 30 min at room temperature. This step was repeated twice more. Detection of neutravidin-HRP bound to peptide was performed using 3-3'-diaminobenzidine and hydrogen peroxide (SIGMAFAST DAB), which generates an insoluble brown product. The wash solution was removed and the acellular dermal matrix samples were placed on a microscope slide and incubated with DAB/peroxide. Color was allowed to develop for 5 min and photographed under tungsten light. The presence of staining on the acellular dermal matrices to which biotinylated cell binding peptide SEQ ID NO: 4 was attached and lack of discernable staining in the control samples indicates that the cell binding peptide was covalently attached over the entire surface of the acellular dermal matrices (data not shown).

Example 9

Figures 20A, 20B:
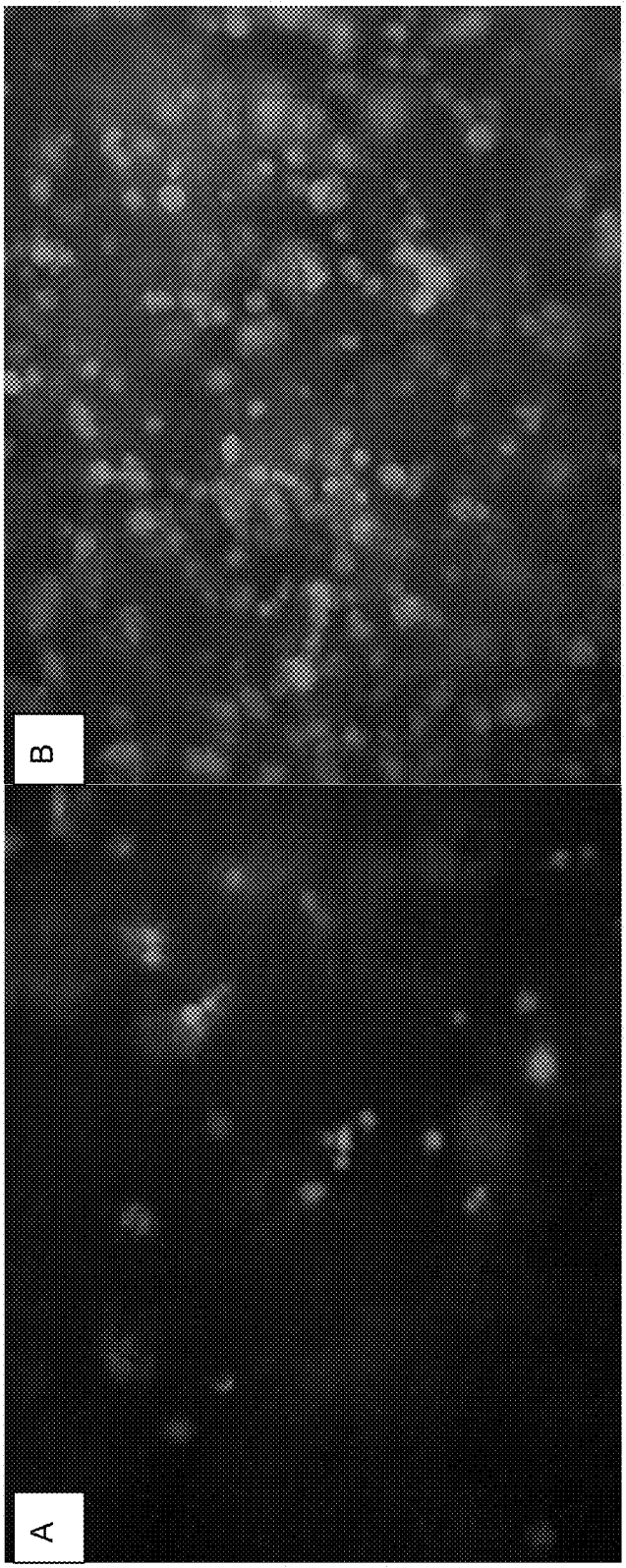
FIGS. 20A and 20B are images showing the ability of a collagen sponge having covalently attached stem cell binding peptide SEQ ID NO: 4 (panel A) to capture cultured human MSCs labeled with fluorescent CELLTRACKER Green dye compared to an unmodified collagen sponge (panel B). The stem cell binding peptide SEQ ID NO: 4 was modified at the carboxyl terminus with a PEG-10 spacer and a lysine residue. After contact with MSCs, sponges were transferred and incubated with 2% fetal bovine serum. Sponge images (16 ms, 10×) were taken after a 19 hour incubation.

Capture of Cultured MSCs with a Cell Binding Peptide Covalently Attached to Collagen This experiment measured the ability of collagen sponge having covalently attached stem cell binding peptide SEQ ID NO: 4 to capture cultured human MSCs compared to unmodified collagen sponge. The cell binding peptide SEQ ID NO: 4 was modified at the carboxyl terminus with a PEG-10 spacer and a lysine residue. The modified cell binding peptide SEQ ID NO: 4 was covalently attached to the collagen sponge as described in Example 6. For the MSC capture experiment, human MSCs were labeled with fluorescent CELLTRACKER Green dye. Unmodified and peptide modified HELISTAT sponge coupons (d=5 mm, thickness=2.5 mm) were used in the experiment. The sponge coupons were pre-wetted in PBS+2% FBS. Sponge coupons were transferred to a suspension of human MSCs (~25,000 cells in 1 ml PBS+2% FBS). The sponge coupons were incubated with the cells for ~3 hr at RT rotating. Images were taken of the sponge coupons immediately after the incubation with cells and again after a transfer to and 19 hr incubation in 1 ml PBS+2% FBS (see FIGS. 20A-20B). The images of the peptide modified (right panel) and unmodified (left panel) sponge coupons shown in FIGS. 20A and 20B demonstrate the significantly improved ability of the peptide modified sponges to capture and retain MSCs. In addition, release of MSCs from the sponges was quantified by measuring both fluorescence and cell count following centrifugation of the sponges to release unbound MSCs (data not shown). Further, after the 19 hr incubation the sponge coupons were digested with collagenase to liberate the remaining bound cells, and the cells were similarly quantified (data not shown). For the peptide modified sponges, approximately 10% of the MSCs were detected in the sponge effluent following incubation with the cells, while approximately 40% of the MSCs were detected in the sponge effluent for the unmodified sponge coupons. Very few cells were detected in the sponge effluent after the 19 hr incubation (1 ml PBS+2% FBS) for either the peptide modified or unmodified sponges. However, after collagenase digestion of the collagen sponges to liberate bound cells, approximately 90% of the total cell count was detected for the peptide modified sponge and approximately 60% of the total cell count was detected for the unmodified sponge. Accordingly, the collagen sponges covalently modified with stem cell binding peptide SEQ ID NO: 4 captured significantly more MSCs than unmodified sponges.

Example 10

Figure 21A:
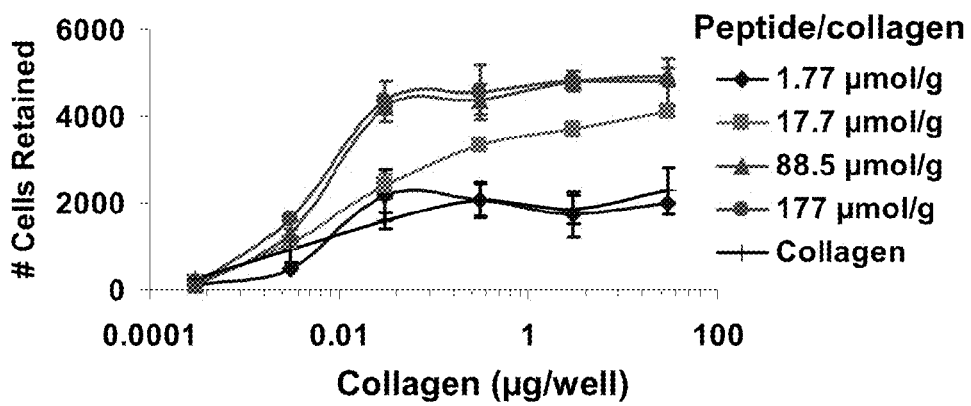
FIGS. 21A-21C demonstrate the ability of collagen having covalently attached cell binding peptide SEQ ID NO: 4 to capture and retain endothelial cells.
Figure 21B:
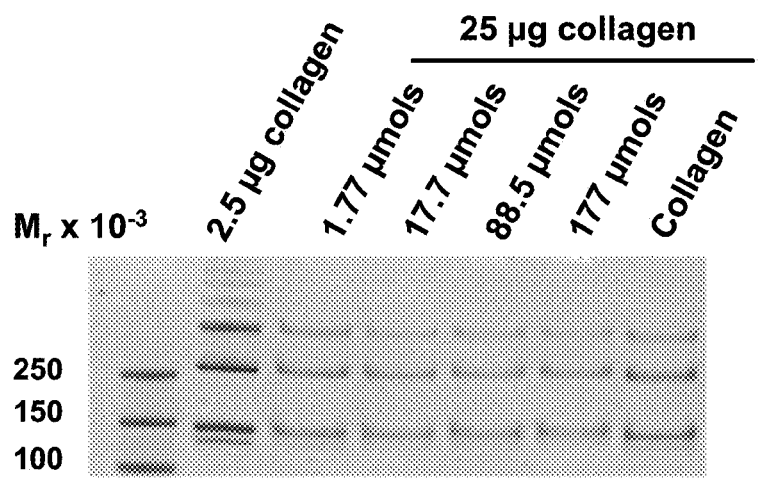
Figure 21C:
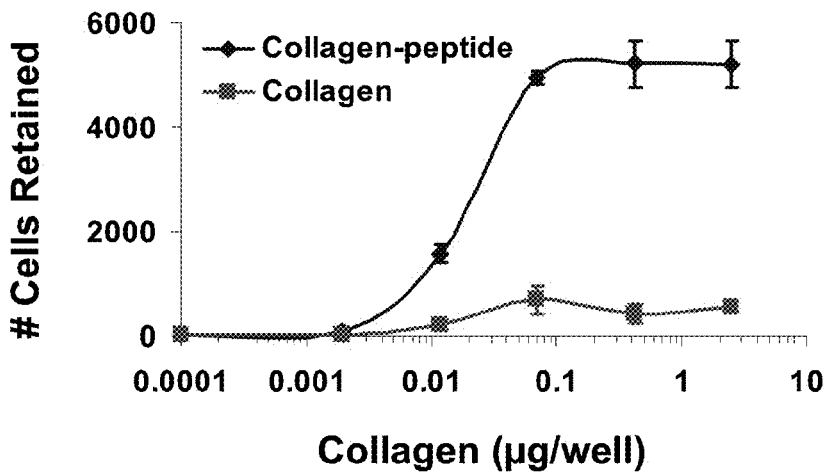

Capture of Endothelial Cells with a Cell Binding Peptide Covalently Attached to Collagen This experiment measured the ability of collagen having covalently attached cell binding peptide SEQ ID NO: 4 (demonstrated to bind to stem cells, fibroblasts, and endothelial cells in Example 3 to capture and retain HUVECs. FIG. 21A shows HUVEC capture by collagen having covalently attached cell binding peptide SEQ ID NO: 4 (generated according to Example 6 using $BS^3$ reagent). Briefly, 96-well plates were coated with increasing amounts of binding peptide-modified collagen over night at 4° C. Unbound collagen was removed and the plates were blocked in tris buffered saline containing 1% BSA for 1 hr at room temperature. After washing, 10,000 HUVECs were added per well in serum free medium for 30 min at 37° C. The plates were washed 3 times with PBS containing 2% FBS, and captured cells were detected with CELLTITER-GLO (INVITROGEN) using a luminometer and a standard curve. FIG. 21A shows a peptide dependent increase in cell retention on peptide-modified collagen, with a 3-fold increase in cell retention for the peptide-modified collagen over unmodified collagen. The 96 well plates were coated with 25 µg of collagen and the data in FIG. 21B show that the collagen coating was similar for all the samples shown in FIG. 21A. For FIG. 21B, the collagen was extracted in gel loading buffer, separated by PAGE, and total protein was stained with SIMPLYBLUE (INVITROGEN). FIG. 21C shows evaluation of HUVEC retention by peptide-modified collagen in the plate format. Plates with captured HUVECs were prepared as described in FIG. 20A. After washing they were incubated with agitation at RT for 1 hour in PBS containing 1% FBS, washed and then retained cells were detected with CELLTITER-GLO. The graph in FIG. 21C shows that after 1 hour with agitation in PBS containing 2% FBS, peptide-modified collagen retained 7-fold more HUVECs than unmodified collagen.

Example 11

Figures 22A, 22B:
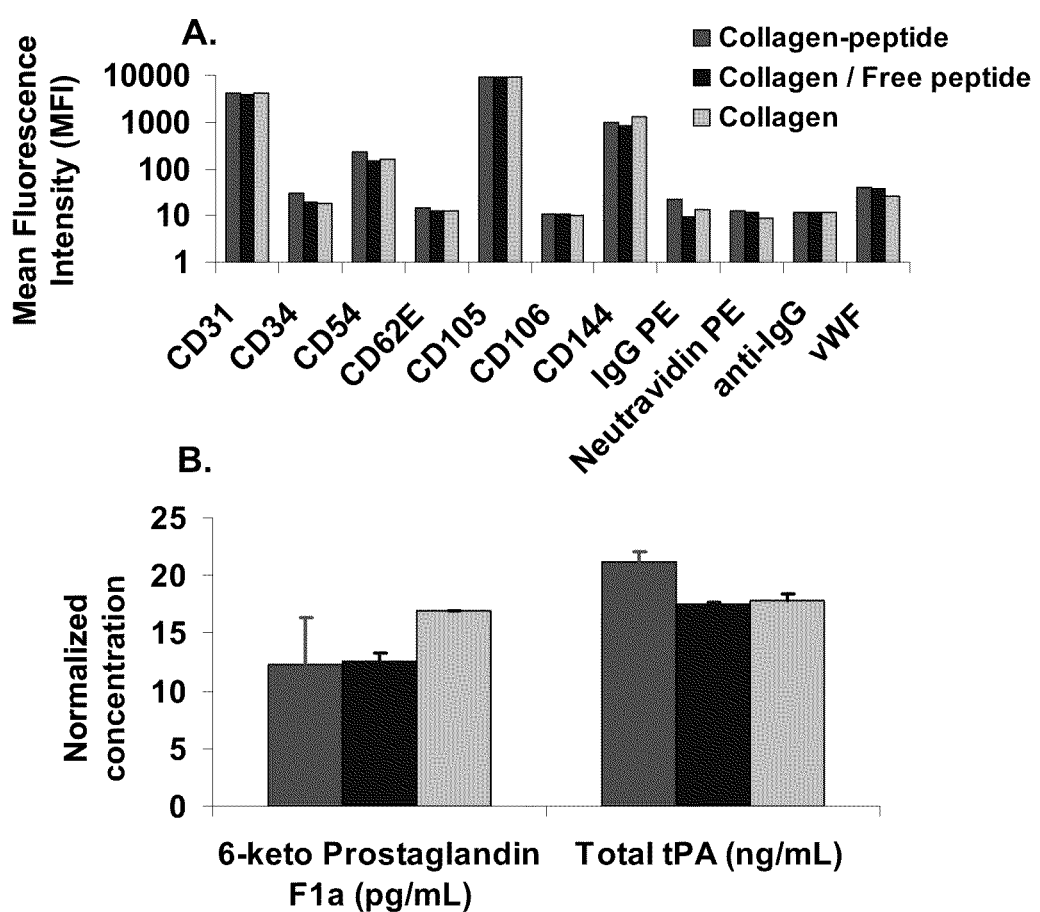
FIGS. 22A-22B are graphs showing that the phenotype, viability, and anti-thrombogenic protein expression profiles for endothelial cells are not altered in the presence of collagen modified with cell binding peptide SEQ ID NO: 4. Cells cultured in the presence of peptide-modified collagen, collagen with free peptide, or collagen alone for 24 hours maintained their endothelial cell phenotype and their ability to secrete anti-thrombogenic proteins.

Cell Binding Peptide Modified-Collagen Binds Endothelial Cells without Altering Phenotype Once immobilized on a vascular graft, endothelial cells must retain their characteristic properties of promoting endothelialization. Therefore, the phenotype, viability, and anti-thrombogenic protein expression profiles were evaluated for endothelial cells in the presence of collagen modified with the endothelial cell binding peptide SEQ ID NO: 4 (generated according to Example 7 using $BS^3$ reagent). Cells cultured in the presence of peptide-modified collagen, collagen with free peptide or collagen alone for 24 hours maintained their endothelial cell phenotype and their ability to secrete anti-thrombogenic proteins. Specifically, HUVECs were plated on SEQ ID NO: 4 peptide-modified collagen, collagen with 10 µM free SEQ ID NO: 4 peptide or collagen alone for 24 hours. Flow cytometry was performed using a BD FACSARRAY, and ELISAs were performed according to manufacturers instructions. (FIGS. 22A & 22B). Tissue-type Plasminogen Activator (t-PA) and 6-keto Prostaglandin F1a protein expression levels secreted in this assay are aligned with other reports on cultured HUVECS (Kimura and Yokoi-Hayashi, Biochim Biophys Acta, 1996, 1310:1-4; Merhi-Soussi et al., J Leukoc Biol, 2000, 68:881-9).

Figure 23:
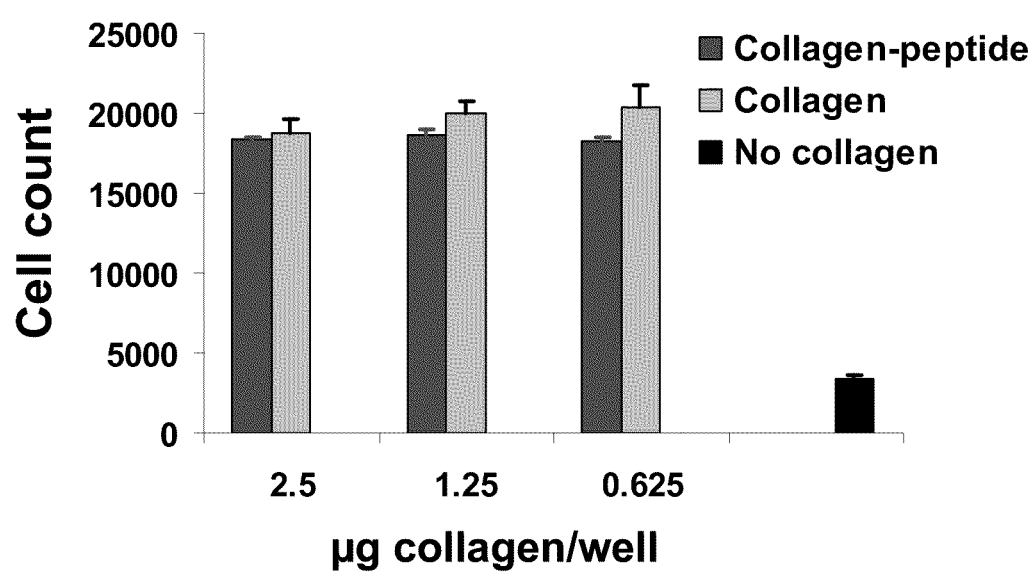
FIG. 23 is a graph showing that HUVECs colonize and proliferate equally on unmodified and SEQ ID NO: 4 cell binding peptide-modified collagen.

In addition, the following experiment was performed to show that HUVECs can colonize and proliferate on cell binding peptide SEQ ID NO: 4-modified collagen. In 96-well plates 7,000 HUVECs were plated on peptide-modified soluble collagen or unmodified collagen for 48 hours at 37° C. Plates were removed and washed and the remaining attached cells were detected using CELLTITER-GLO on a luminomenter. The graph in FIG. 23 shows that HUVECs colonize and proliferate equally on unmodified and cell binding peptide-modified collagen (FIG. 23).

Figure 24:
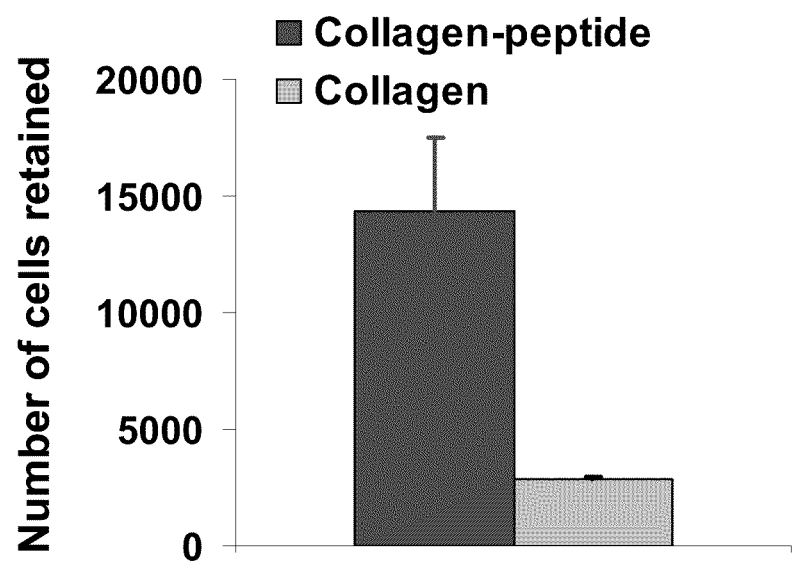
FIG. 24 is a graph showing HUVEC retention by SEQ ID NO: 4 cell binding peptide-modified- and unmodified-collagen sponges. After 20 hours of incubation with the HUVECs, the cell binding peptide-modified sponge retained 5-fold more cells than the unmodified collagen sponge.

The presentation of cell binding peptide-modified collagen to endothelial cells in a plate format may be very different than an acellular, collagen-rich artery. Therefore, cell binding peptide-modified HELISTAT collagen sponges were used to better model the proposed vascular graft application. The cell binding peptide-modified HELISTAT collagen sponges were generated according to Example 7. HUVEC retention was compared for cell binding peptide-modified- and unmodified-collagen sponges. Briefly, peptide-modified or unmodified collagen sponges were rehydrated in serum free medium containing 50,000 CELLTRACKER GREEN labeled HUVECs. The sponges were incubated at RT rotating in PBS containing 2% FBS. At 1, 2, and 20 h the samples were placed in a new tube with fresh buffer. After the 20 h incubation, the sponges were digested with 100 U collagenase for 16 h and the remaining cells enumerated. After 20 hours with agitation, the cell binding peptide-modified sponge retained 5-fold more cells than the unmodified collagen sponge (FIG. 24).

Figure 25:
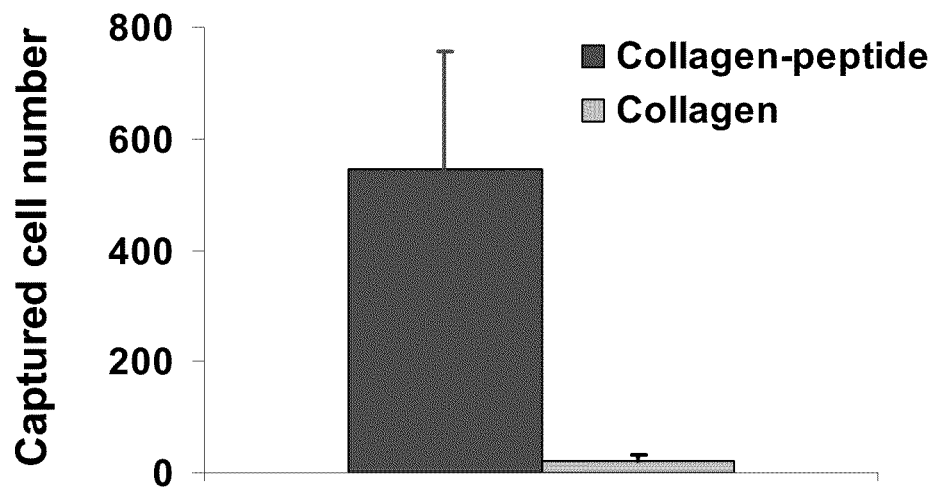
FIGS. 25A-25B are graphs showing the ability of collagen modified with cell binding peptide SEQ ID NO: 4 to capture cells in flow or under shear stress. Glass cover-slips were coated with peptide modified collagen or unmodified collagen and seeded with ECFCs in flow (Panel A) or HUVECs under shear stress (Panel B).
Figure 25:
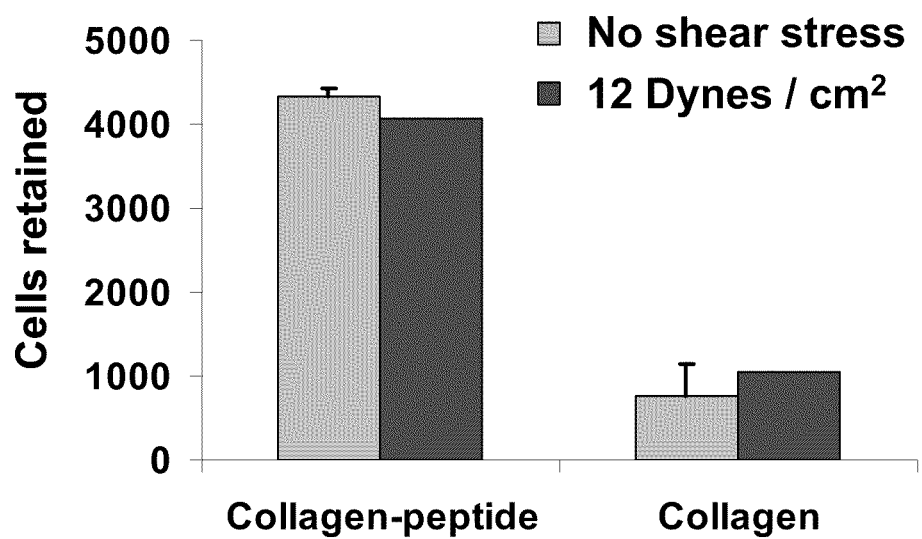

The ability of the collagen modified with endothelial cell binding peptide SEQ ID NO: 4 to capture ECFCs in flow was analyzed as follows. Glass coverslips were coated with unmodified collagen or cell binding peptide modified-collagen and mounted in a polycarbonate parallel plate flow chamber. PBS/10% FBS was circulated through a closed 150 ml system to block the coverslips. Approximately $2 \times 10^6$ ECFC were injected into the system and were circulated for 2 h at 37° C. Coverslips were washed in PBS to remove loosely adhering cells, the remaining cells on the coverslips were lysed in CELLTITERGLO (INVITROGEN, CA), and the cells enumerated by luminescence against a standard curve. The data in FIG. 25A show that the peptide modified collagen captured about 20-fold more cells than the unmodified collagen.

The ability of the collagen modified with endothelial cell binding peptide SEQ ID NO: 4 to retain HUVECs under shear stress was analyzed as follows. Glass cover-slips were coated with peptide conjugated collagen or unmodified collagen and seeded with HUVECs. Coverslips were secured in a polycarbonate slide with six 1 cm diameter wells enabling simultaneous testing of materials. A closed loop peristaltic pump was used to expose the samples to flow conditions for 30 minutes at laminar flow rates up to 12 dynes/cm$^2$ in PBS containing 2% FBS. The number of cells retained on the cover slip was determined using CELLTITER-GLO (INVITORGEN) and a luminometer. The data in FIG. 25B show that the peptide modified-collagen captured about 3-fold more cells than the unmodified collagen, and the application of shear stress did not significantly affect cell capture by peptide modified- or unmodified-collagen.

Example 12

Differentiation of MSCs Captured with Stem Cell Binding Peptide into Adipocytes, Osteoblasts, or Chondrocytes This experiment was performed to determine whether MSCs captured with a stem cell binding peptide retained the ability to differentiate into cells of mesenchymal origin.

Adipocyte Differentiation.

Figures 26A, 26B, 26C, 26D:
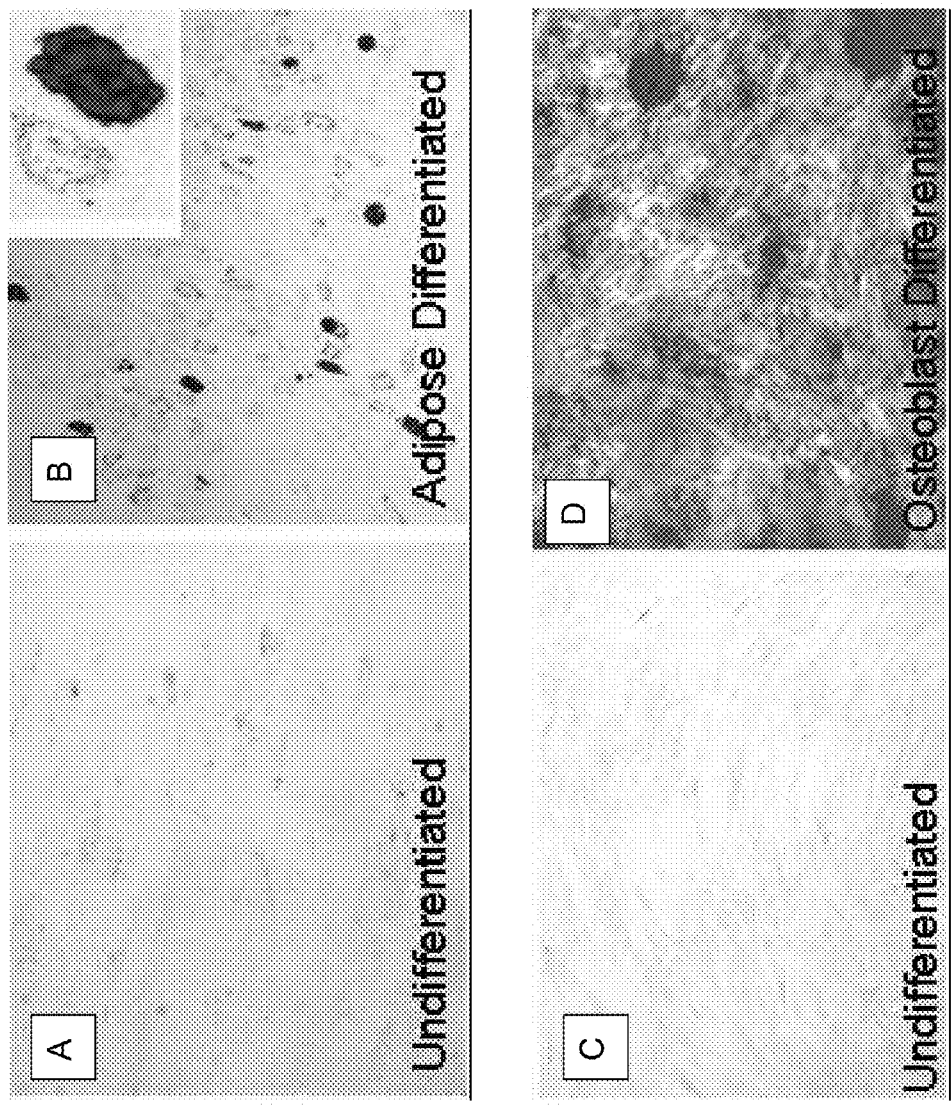
FIGS. 26A-26D are images of differentiated MSCs captured from bone marrow aspirate with stem cell binding peptide SEQ ID NO: 4. Following a 21 day incubation in adipocyte differentiation media, captured MSCs were fixed and stained with Oil Red O to determine the extent of adipogenesis. Panel A shows undifferentiated MSCs and panel B shows adipocyte differentiated MSCs. The image of the adipose differentiated cells (panel B) contains a larger magnification inset where the lipid vacuoles are clearly visible. Following a 14 day incubation in osteoblast differentiation media, the captured MSCs were stained with Alizarin Red S to reveal mineralizing osteoblasts. Panel C shows undifferentiated MSCs and panel D shows osteoblast differentiated MSCs.

After capture of MSCs using cell binding peptide SEQ ID NO: 4 with the MILTENYI magnetic system according to Example 6, the ability of the captured cells to differentiate into an adipocyte lineage was examined. The MSCs present in the MILTENYI column eluants (see Example 6) were cultured for 21 days in complete medium (DMEM, 10% FBS, 100 units/mL penicillin, 100 µg/mL streptomycin, and 2 mM glutamine) supplemented with 0.5 mM isobutyl methylxanthine, 1 µM dexamethasone, 10 µM insulin, 200 µM indomethacin, and 1% antibiotic/antimycotic. Following the 21 day incubation, the cells were fixed in 4% paraformaldehyde in PBS for 15 minutes, washed in 60% isopropanol for 5 minutes, and stained with Oil Red 0 (SIGMA) for 10 minutes to determine the extent of adipogenesis (see FIG. 26, panels A (undifferentiated MSCs) and panel B (adipocyte differentiated MSCs)). The image of the adipose differentiated cells (FIG. 26, panel B) contains a larger magnification inset where the lipid vacuoles are clearly visible. The results shown in panels A and B of FIG. 26 show that the adipogenesis pathway remains intact for the MSCs after capture from bone marrow using stem cell binding peptide SEQ ID NO: 4.

Osteoblast Differentiation.

For osteogenic differentiation, the MSCs present in the MILTENYI column eluants (see Example 6) were cultured for 14 days in complete medium supplemented with 0.1 µM dexamethasone, 50 µM ascorbate-2-phosphate, 10 mM β-glycerophosphate, and 1% antibiotic/antimycotic. Calcium mineralization was measured by Alizarin Red S (SIGMA) staining to reveal mineralizing osteoblasts (see FIG. 26, panel C (undifferentiated MSCs) and panel D (osteoblast differentiated MSCs)). The results shown in panels C and D of FIG. 26 show that the osteogenic pathway remains intact for the MSCs after capture from bone marrow using stem cell binding peptide SEQ ID NO: 4.

Chondrocyte Differentiation.

Figures 27A, 27B, 27C, 27D:
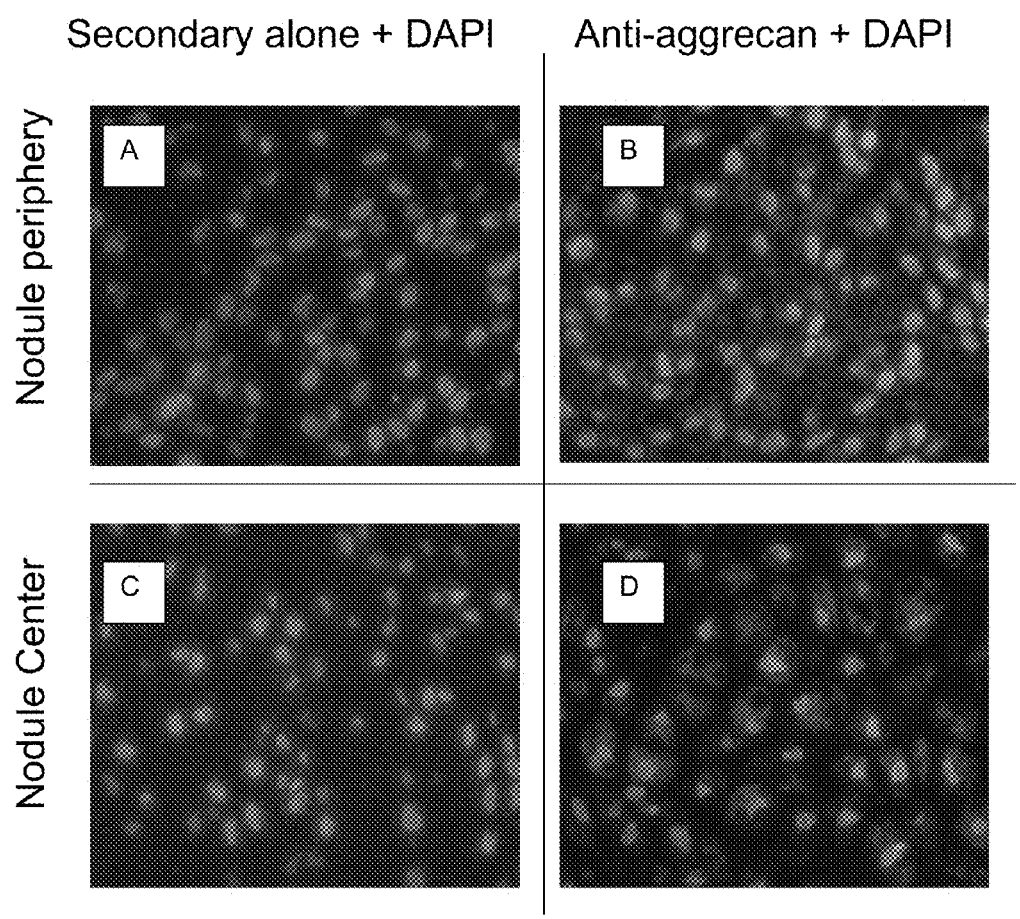
FIGS. 27A-27D are images of differentiated MSCs captured from bone marrow aspirate with a stem cell binding peptide SEQ ID NO: 4.

To examine chondrocyte differentiation, the MSCs present in the MILTENYI column eluants (see Example 6) were pelleted by centrifugation at 150×g for 5 minutes. Cells were washed once with 1 ml MACS NH CHONDRODIFF Medium without disturbing the pellet. Cells were spun again and 1 mL CHONDRODIFF Medium was added to each pellet. Every third day, medium was aspirated and replaced with fresh pre-warmed medium. After 24 days in culture, cells exposed to CHONDRODIFF medium formed cartilage plugs or nodules, whereas control cells formed only loose or small nodules. Cells were washed once with PBS and fixed in neutral buffered formalin overnight. Sections were embedded in paraffin and sectioned at 5 microns. Sections were examined by hemotoxylin and eosin staining (data not shown). Sections were further examined by immunostaining for aggrecan, a major structural component of cartilage. In FIG. 27, sections from the periphery (panels A and B) or center (panels C and D) were incubated with an antibody against aggrecan (ABCAM) (panels B and D) or with secondary detection reagents only as a control (panels A and C), then counterstained with DAPI to reveal cell nuclei. After 24 days in the culture medium, aggrecan could be detected in the nodules formed from the MSCs captured by cell binding peptide SEQ ID NO: 4. Control images of captured cells grown in the absence of differentiation medium could not be taken due to the small and loose nature of nodules.

Example 13

Enhanced Fibroblast Binding to Cell Binding Peptide-Modified Collagen

Figure 28:
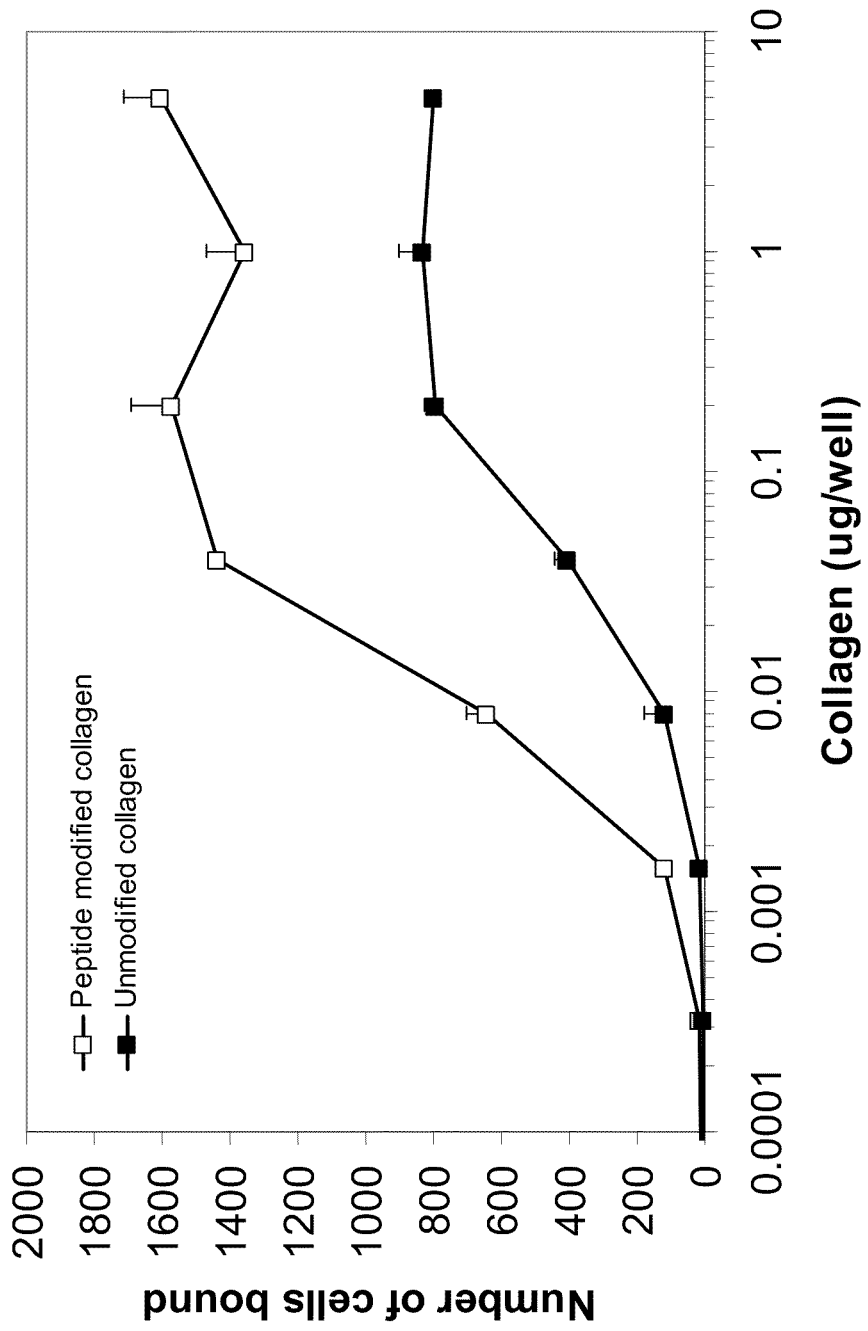
FIG. 28 is a graph showing enhanced binding of human dermal fibroblasts to cell binding peptide (SEQ ID NO: 4)-modified collagen compared to unmodified collagen. The collagen was coated on a polystyrene microtiter plate.

This example demonstrates that collagen modified with cell-binding peptide (SEQ ID NO: 4) binds more fibroblasts than unmodified collagen. The experiment was performed according to the following procedure. Cell-binding peptide (SEQ ID NO: 4) was covalently attached to soluble collagen as described herein at Example 7. 96-well plates were coated with various amounts of unmodified or the peptide-modified collagen (177 µmol peptide/g collagen) over night at 4° C. Unbound collagen was removed and the plates were blocked for 1 h. After washing, 5,000 human dermal fibroblasts were added per well in serum-free medium for 30 min at 37° C. The plates were washed, and bound cells were detected with CELLTITER-GLO (PROMEGA) using a luminometer. At 0.0025 µg collagen, fibroblast binding was increased 11-fold for the peptide-modified collagen compared to unmodified collagen (see FIG. 28). Increased cell binding was also observed at higher concentrations of the SEQ ID NO: 4 peptide-modified collagen (data not shown).

Example 14

Identification of PDGF Binding Peptides by Phage Display

Peptides that bind PDGF were identified by phage display biopanning. Enrichment of PDGF-binding phage in the selection was monitored using an ELISA-type assay with an HRP-conjugated anti-M13 antibody. After enrichment for PDGF-BB specific phage, individual phage were picked, propagated on E. coli, and tested for binding to PDGF-BB. The DNA from phage displaying peptides that displayed binding to rhPDGF-BB was analyzed, and the amino acid sequences of the displayed peptides were deduced from the DNA sequence (see Table 2; SEQ ID NOs: 21-27).

TABLE 2

Amino Acid Sequences from PDGF Phage Display

| SEQ ID NO: | Amino acid sequence (single letter code) |
|---|---|
| 21 | SSGSDPSSSWFPPPVWFSSR |
| 22 | SSLAAWYSSWGVS |
| 23 | SEATQASRNWEGIRVFLASR |
| 24 | SEWDQYYSYYLEH |
| 25 | SPWVTWYYSASSP |
| 26 | STMLSWDHVNLYYTMH |
| 27 | SPLLHWNKIQDYYRLN |

The PDGF-binding peptide sequences were then synthesized using standard solid-phase peptide synthesis techniques on a SYMPHONY Peptide Synthesizer (PROTEIN TECHNOLOGIES, Tucson, Ariz.) using standard Fmoc chemistry (HBTU/HOBT activation, 20% piperidine in DMF for Fmoc removal). N-α-Fmoc-amino acids (with orthogonal side chain protecting groups) were purchased from Novabiochem. After all residues were coupled, simultaneous cleavage and side chain deprotection was achieved by treatment with a trifluoroacetic acid (TFA) cocktail. Crude peptide was precipitated with cold diethyl ether and purified by high-performance liquid chromatography on a WATERS ANALYTICAL/Semi-preparative HPLC unit on VYDAC C18 silica column (preparative 10 µm, 250 mm×22 mm) using a linear gradient of water/acetonitrile containing 0.1% TFA. Homogeneity of the synthetic peptides was evaluated by analytical RP-HPLC (VYDAC C18 silica column, 10 µm, 250 mm×4.6 mm) and the identity of the peptides confirmed with MALDI-TOF-MS. Biotinylated peptides were generated similarly, with a GSSGK(biotin) sequence added to the C-terminus of the peptide.

Figure 29:
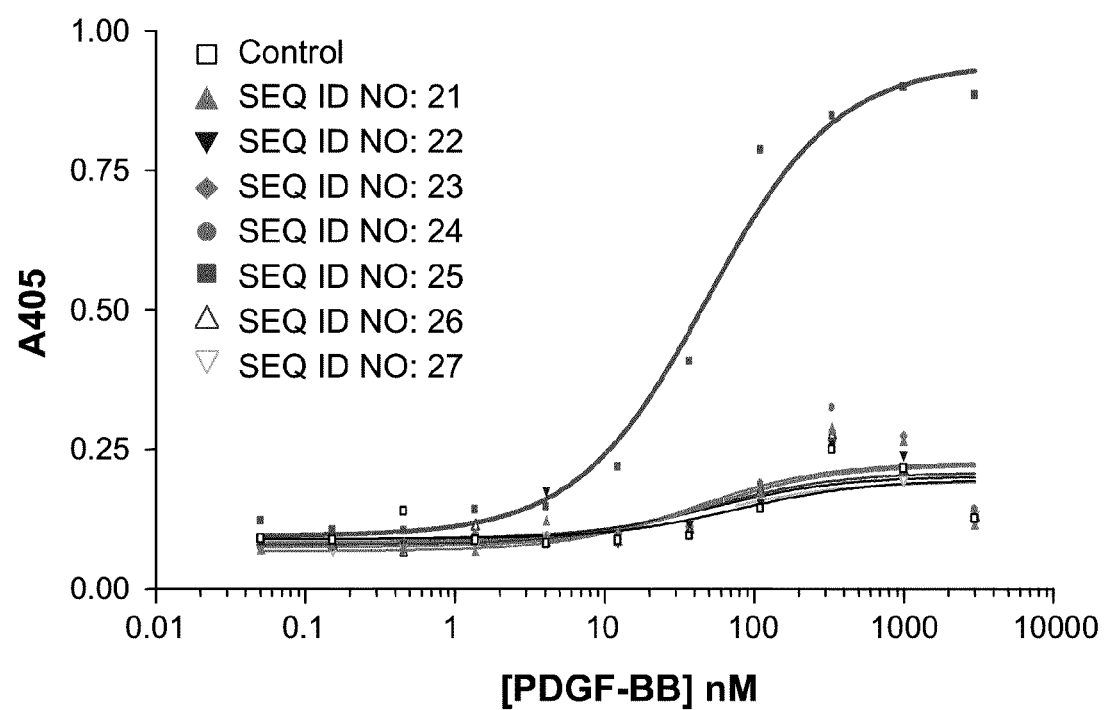
FIG. 29 is a graph showing the binding curves for PDGF-binding peptides where increasing concentrations of PDGF growth factor are examined. The numbers in FIG. 29 refer to PDGF-binding peptides SEQ ID NOs: 21-27. "Control" refers to a peptide known not to bind to PDGF.

The PDGF-BB binding peptides with the biotin moiety on their C-terminus were tested for their ability to bind the target growth factor using the following methods. Streptavidin-coated plates were first prepared by generating a 1:100 dilution of streptavidin (1 mg/mL) in 0.1M NaHCO$_3$ buffer. In each well of a 96-well IMMULON 4HBX plate, 50 µL of this solution was added (0.5 µg of streptavidin per well). Plates were incubated overnight at 4° C. Wells were blocked with 150 µL/well of bovine serum albumin (1%) in 0.1M NaHCO$_3$ buffer. Plates were either stored at 4° C. or incubated 1 hr at room temperature, if plates were to be used immediately. Prior to use plates were washed three times in TBS-T (TBS+ 0.05% Tween-20). Peptides were diluted to 0.2 µM in 100 µL of TBS-T. Peptide solution was added to each well and incubated for 45 min at room temperature. Remaining streptavidin binding sites were blocked with free biotin (0.5 mM). Plates were washed three times in TBS-T to remove unbound peptide. Growth factor solution (PDGF-BB), starting at 1 µM was run through a 2-fold dilution series to generate a range of concentrations (1 µM-1 nM) in a 50 µL volume in each well. Growth factor was added to each well and incubated for 40 min at room temperature. Plates were washed five times in TBS-T to remove unbound growth factor. Antibodies against growth factor PDGF-BB were added (ABCAM Cat#: ab15499) for 30 min at room temperature. Plates were washed with TBS-T and an alkaline phosphatase-conjugated secondary antibody (anti-mouse, 1:1000 dilution) was added to each well. To reveal immunoreactivity, 100 µL of para-nitrophenyl phosphate solution was added to each well, and optical density was recorded on a spectrophotometer. The results are shown in FIG. 29 (the numbers in FIG. 29 refer to SEQ ID NOs: 21-27). The peptide having SEQ ID NO: 25 was observed to have the best binding affinity for PDGF-BB. "Control" in FIG. 29 is a negative control peptide known not to bind PDGF. The following PDGF-binding sequence motif was generated based on the FIG. 29 results and allowing for conservative amino acid substitutions in SEQ ID NO: 25: small-small-Z-aliphatic-small-Z-Z-Z-small-aliphatic-small-small-small, wherein "small" is S, T, G, or P; wherein "Z" is Y, W, or F; and wherein "aliphatic" is A, V, I, or L (SEQ ID NO: 28).

Figure 30:
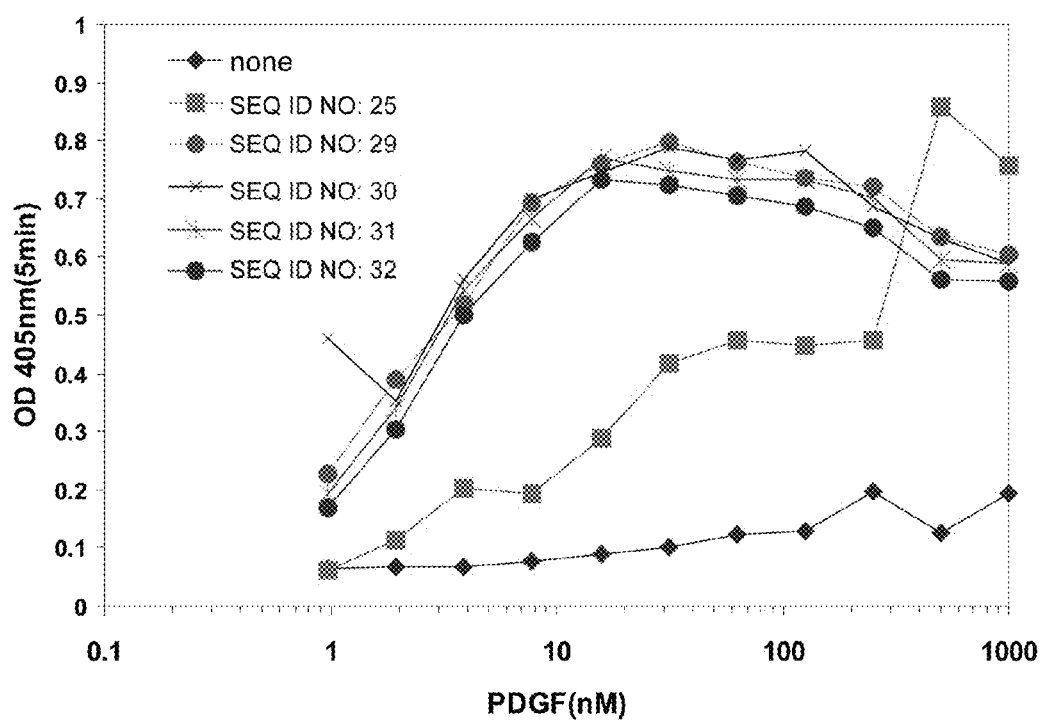
FIG. 30 is a graph showing the binding curves for PDGF-binding peptides having an N-terminal amino acid tag where increasing concentrations of PDGF growth factor are examined. The numbers in FIG. 30 refer to PDGF-binding peptides SEQ ID NOs: 25 and 30-32.

In addition to the PDGF-binding sequences identified through the phage display, additional PDGF-binding peptides were generated by synthesizing the SEQ ID NO: 25 peptide with an acidic amino acid sequence of varying lengths incorporated at the N-terminus (see Table 3). The peptides in Table 3 were synthesized as described above, and similarly tested for their ability to bind PDGF-BB using the methods described above. Unexpectedly, enhanced binding affinity for PDGF-BB was observed for the peptides with the incorporated N-terminal acidic amino acid sequence (see FIG. 30; the numbers in FIG. 30 refer to SEQ ID NOs: 25 and 29-32). The following PDGF-binding sequence motifs were generated based on the FIG. 30 results for the tagged peptides shown in Table 3: motif #1 is Tag-(SEQ ID NO: 28), wherein "Tag" is from 0-6 amino acids. Another PDGF-binding sequence motif is as follows: motif #2 is $(D/E)_{n1}$-(SEQ ID NO: 28)-$(D/E)_{n2}$, wherein D/E is aspartate or glutamate, n1 and n2 are 0-6, and at least one of n1 or n2 must be 0. Another PDGF-binding sequence motif is as follows: motif #3 is $(D/E)_{n1}$-(SEQ ID NO: 28), wherein D/E is aspartate or glutamate, n1 is 0-6. Another PDGF-binding sequence motif based on SEQ ID NO: 25 and the results in FIG. 30 is as follows: motif #4 $((D/E)_{n1}$-(SEQ ID NO: 25) wherein n1 is 0-6.

TABLE 3

PDGF Binding Peptides

| SEQ ID NO: | Amino acid sequence (single letter code) |
|---|---|
| 29 | DD-SPWVTWYYSASSP |
| 30 | DDDD-SPWVTWYYSASSP |
| 31 | DEDE-SPWVTWYYSASSP |
| 32 | DEDEDE-SPWVTWYYSASSP |

Figure 31:
FIG. 31 is a schematic depiction of truncations of PDGF binding peptide SEQ ID NO: 25 where the truncated peptides have been examined for binding to PDGF relative to the full-length sequence (indicated by a "+" or "−" symbol). The numbers in FIG. 31 refer to peptides SEQ ID NOs: 25 and 33-37.

The binding activity of the PDGF-binding peptide SEQ ID NO: 25 was further investigated by truncation analysis. Potentially the most straightforward way to limit the complexity of peptide synthesis is to reduce the number of amino acids included in the length of the peptide sequence. The peptide SEQ ID NO: 25 was shortened on both C and N termini to determine the minimal sequence required for PDGF binding (see Table 4). Each truncated peptide was synthesized with a biotin tag and, after purification, the truncated peptides were immobilized on streptavidin plates for PDGF-BB binding experiments as described above. FIG. 31 provides a schematic diagram of the truncations generated and their comparative PDGF binding capabilities compared to the SEQ ID NO: 25 peptide (the numbers in FIG. 31 refer to peptide SEQ ID NOs: 25 and 33-37). Slight decrements in binding relative to SEQ ID NO: 25 were observed in SEQ ID NO: 33 (4 residues shorter than SEQ ID NO: 25) and SEQ ID NO: 36 (2 residues shorter than SEQ ID NO: 25). The data suggest a minimum PDGF binding domain in which 4 amino acids are removed from the C terminus of SEQ ID NO: 25, i.e., SEQ ID NO: 33. The following PDGF-binding sequence motifs were generated based on the FIGS. 30 and 31 results for the tagged and truncated peptides shown in Tables 3 and 4: $Tag_1$-small-small-Z-aliphatic-small-Z-Z-Z-small-$Tag_2$ (SEQ ID NO: 38), wherein "$Tag_1$ and $Tag_2$" are $(D/E)_{0-6}$, wherein "small" is S, T, G, or P; wherein Z is Y, W, or F; wherein "aliphatic" is A, V, I, or L; and wherein at least one of $Tag_1$ or $Tag_2$ must be 0. Another PDGF-binding sequence motif based on SEQ ID NO: 33 and the FIGS. 30 and 31 results for the tagged and truncated peptides is as follows: $Tag_1$-small-small-Z-aliphatic-small-Z-Z-Z-small (SEQ ID NO: 39), wherein "$Tag_1$" is $(D/E)_{0-6}$, wherein "small" is S, T, G, or P; wherein Z is Y, W, or F; wherein "aliphatic" is A, V, I, or L. Another PDGF-binding sequence motif based on SEQ ID NO: 33 and the FIGS. 30 and 31 results for the tagged and truncated peptides is as follows: motif #5 $(D/E)_{n1}$-(SEQ ID NO: 33), wherein n1 is 0-6.

TABLE 4

PDGF Binding Peptide Truncation Analysis

| SEQ ID NO: | Amino acid sequence (single letter code) |
|---|---|
| 33 | SPWVTWYYS |
| 34 | WVTWYYSASSP |
| 35 | TWYYSASSP |
| 36 | SPWVTWYYSAS |
| 37 | SPWVTWY |

Example 15

Covalent Attachment of PDGF Binding Peptide to a Collagen Substrate

Figure 32:
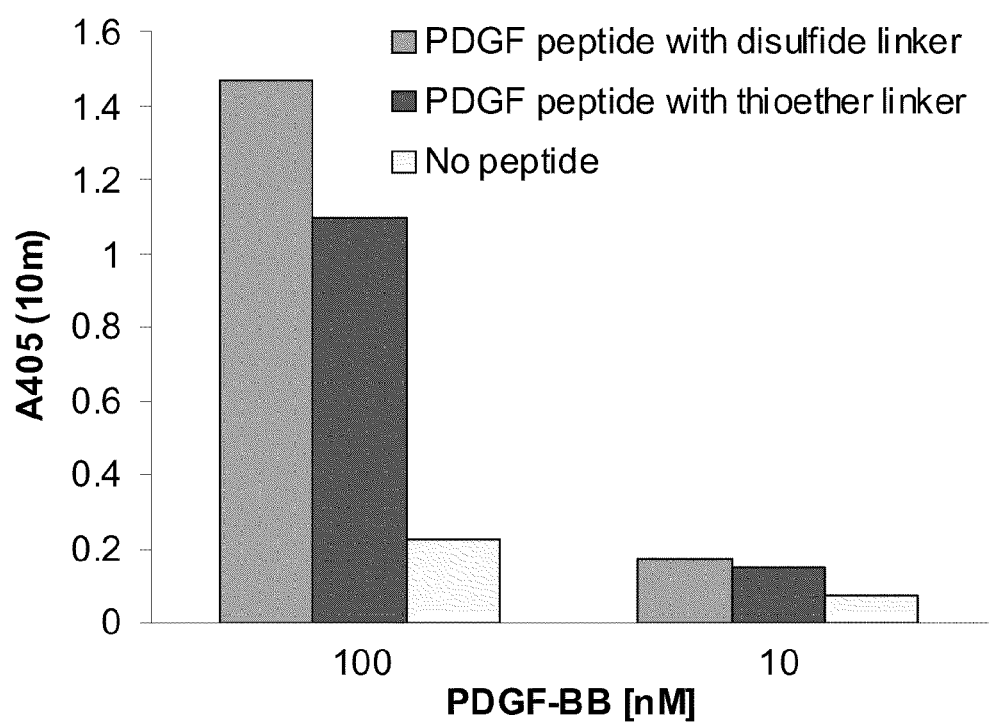
FIG. 32 is a graph showing PDGF-BB loading at 10 and 100 nM on a PDGF binding peptide (SEQ ID NO: 29)-modified collagen sponge versus an unmodified sponge control. The PDGF binding peptide-modified sponges bound significantly more PDGF-BB than the unmodified sponges.

In this experiment PDGF binding peptide (SEQ ID NO: 29) was covalently attached to a collagen sponge (HELISTAT sponge; INTEGRA LIFE SCIENCES). The PDGF binding peptide SEQ ID NO: 29 further comprising an amino acid spacer and a cysteine functional group was covalently bound to the collagen sponge using standard thioether or disulfide chemistries. The ability of the PDGF binding peptide-modified sponge to bind PDGF-BB was tested. PDGF binding peptide-modified and unmodified sponges were incubated with PDGF-BB at various concentrations for 30 min. After washing, the sponges were incubated with an antibody to PDGF-BB (ABCAM), followed by an alkaline phosphatase-linked secondary antibody (PROMEGA). Antibody that bound to PDGF-BB on the sponge was detected with the chromogenic substrate pNPP. The data in FIG. 32 show that PDGF binding peptide-modified sponge bound more PDGF-BB than unmodified sponge.

Figures 33A, 33B:
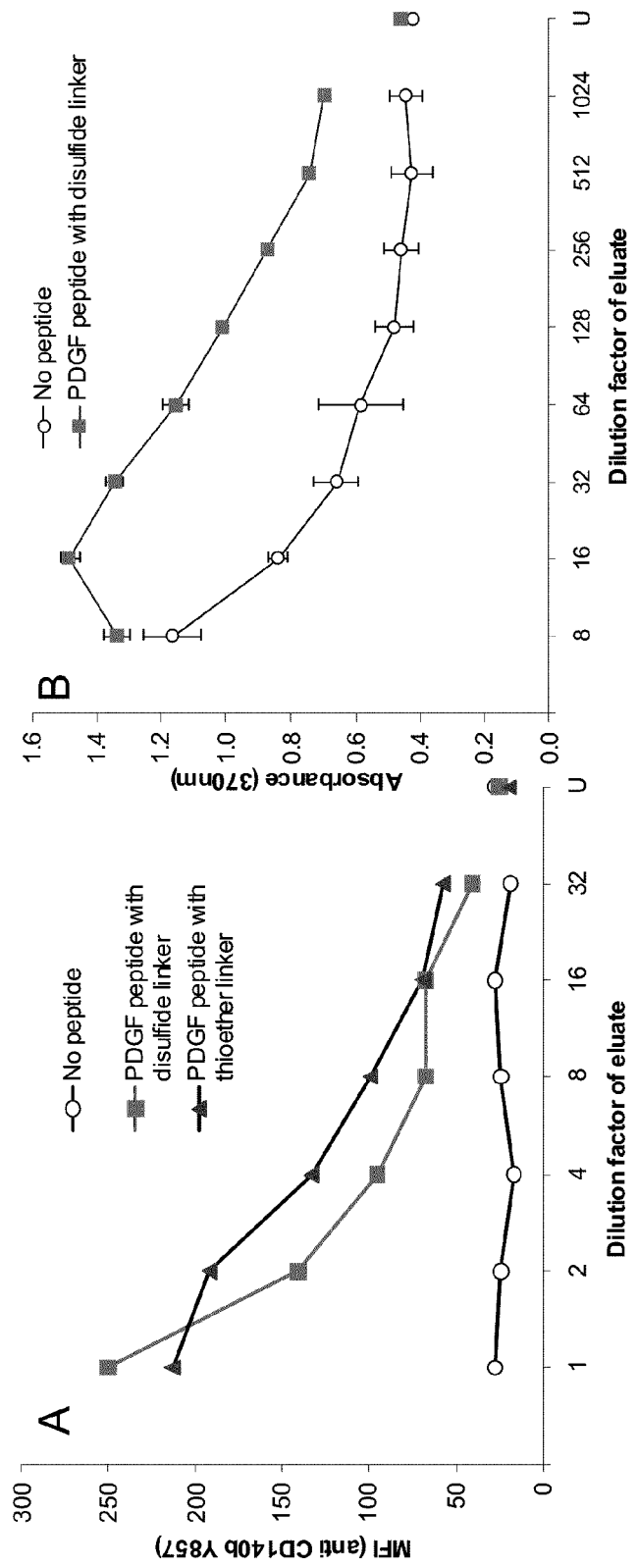
FIGS. 33A-33B are graphs showing bioactivity of PDGF-BB after binding to a PDGF binding peptide-modified sponge (SEQ ID NO: 29). Panel A) Tyrosine phosphorylation of the PDGF receptor by PDGF-BB released from PDGF binding peptide-modified or unmodified sponges by collagenase. Panel B) BrdU incorporation into NIH-3T3 cells after stimulation with PDGF-BB released by acid elution. U, unstimulated (far right point on graphs).

Next, the ability of the PDGF binding peptide-modified sponge to deliver bioactive PDGF was assessed. PDGF binding peptide-modified and unmodified collagen sponges were incubated with PDGF-BB and then washed. The remaining bound PDGF-BB was released by collagenase digestion, and the collagenase eluate was added at a range of dilutions to HEK293 cells transfected with PDGF receptor β. After washing, the cells were incubated with an antibody against phosphorylated PDGF receptor β (pY857). Tyrosine phosphorylation was assessed by flow cytometry. The eluate from the unmodified sponges did not stimulate phosphorylation of PDGF receptor β, whereas the eluate from the PDGF binding peptide-modified sponges stimulated phosphorylation of the receptor (FIG. 33A). When the remaining bound PDGF-BB was released by acid elution instead of collagenase digestion, the eluates showed a similar ability to stimulate tyrosine phosphorylation (data not shown). In addition, the biological activity of acid-eluted PDGF-BB was further assessed by measuring the ability of the eluted PDGF-BB to induce cell proliferation by measuring BrdU incorporation into NIH-3T3 cells. The eluates (n=3) were incubated with NIH-3T3 cells, and cell proliferation was measured by ELISA as incorporation of BrdU (ROCHE CELL PROLIFERATION ASSAY). The data in FIG. 33B show that the eluate from PDGF binding peptide-modified sponge stimulated cell proliferation significantly more than the eluate from unmodified sponge. Taken together, these data indicate that our PDGF binding peptide can bind and retain a bioactive form of PDGF.

Example 16

Covalent Attachment of a Binding Peptide to Polyanhydride Polymer

A binding peptide is covalently attached to polymaleic anhydride (PMA) using established methods (Pompe, et al., 2003, Biomacromolecules, 4(4):1072-9). First, a spacer, such as for example, GSSGK, is added to a terminus of the peptide and the peptide is attached to the PMA anhydride groups through the reactive terminal lysine amine group on the peptide-spacer. A schematic diagram of one example of this chemistry is shown in FIG. 6. PMA ~5,000 MW is dissolved in anhydrous dimethylformamide (DMF) and peptide is dissolved in DMF with excess diisopropylethylamine (DIEA). The peptide solution is heated with the PMA solution at 40° C. overnight, for example, and the reaction mixture quenched with water. The crude PMA-peptide conjugate is filtered and analyzed. For example, the extent of substitution on the polyanhydride polymer can be estimated by integration of $^1$H-NMR peaks from the peptide together with the integrals of key reference peaks on the polymer to provide an estimate of the level of peptide substitution. In another example, size exclusion chromatography is used by monitoring the UV absorption of the peptide along with a known amount of unconjugated PMA. The degree of peptide substitution is estimated from the mass of the lyophilized product and the UV absorbance of the peptide component.

Example 17

GDF-7 Binding Peptides

GDF binding peptides disclosed in US Patent Application Publication No. US 2009/0098175 A1 are provided, and, in particular, the following GDF binding peptides from US Patent Application Publication No. US 2009/0098175 A1 shown herein at Table 5 (SEQ ID NOs: 40-43).

TABLE 5

GDF-7 Binding Peptides

| SEQ ID NO: | Amino acid sequence |
|---|---|
| 40 | ssGPREIWDSLVGVVNPGWsr |
| 41 | ssGGVGGWALFETLRGKEVsr |

TABLE 5-continued

GDF-7 Binding Peptides

| SEQ ID NO: | Amino acid sequence |
|---|---|
| 42 | ssVAEWALRSWEGMRVGEAsr |
| 43 | WXXFE(S/T)LXGXEX |

Example 18

Covalent Attachment of Cell Binding Peptide to Dextran

Cell binding peptide SEQ ID NO: 4 having a C-terminal spacer and lysine residue was covalently attached to dextran (POLYSCIENCES, Inc, PA). Dextran (3-7M; 27.7 mg) was first oxidized by dissolving the dextran in 6 mL of PBS buffer pH 7.5, adding $NaIO_4$ (90 mg), and the vortexing in the dark for 4 hours at room temperature. The reaction mixture was dialyzed against distilled water and lyophilized to give aldehyde activated dextran as a white spongy mass. The peptide was reacted with the aldehyde activated dextran in 0.1 M sodium acetate buffer at pH 5.5 for 3 hours in the dark. Approximately 10 mg of $NaCNBH_3$ was added to the reaction and incubated overnight at room temperature in the dark. Unreacted peptide and other reagents were removed by extensive dialysis against water.

To show that peptide SEQ ID NO: 4 conjugated to soluble dextran described above retained cell binding activity, a stem cell binding competition assay was performed with free peptide SEQ ID NO: 4 by flow cytometry. The SEQ ID NO: 4 peptide-modified dextran was mixed with human MSCs and then incubated with biotinylated stem cell binding peptide SEQ ID NO: 4, the binding of which could be measured by flow cytometry using neutravidin-phycoerythrin. The SEQ ID NO: 4 peptide-modified dextran was a strong competitor of free peptide SEQ ID NO: 4 with a 50% inhibition value below 1 μM, suggesting that the covalently attached stem cell peptide retains its ability to bind MSCs and that the SEQ ID NO: 4 peptide-modified dextran has a higher affinity for MSCs (data not shown).

The foregoing description of the specific embodiments of the presently disclosed subject matter has been described in detail for purposes of illustration. In view of the descriptions and illustrations, others skilled in the art can, by applying current knowledge, readily modify and/or adapt the presently disclosed subject matter for various applications without departing from the basic concept of the presently disclosed subject matter; and thus, such modifications and/or adaptations are intended to be within the meaning and scope of the appended claims.

What is claimed is:

1. A cell binding peptide comprising a sequence selected from the group consisting of SEQ ID NO: 16 and conservatively substituted variants of SEQ ID NO: 16 having at least 85% sequence identity to SEQ ID NO: 16, wherein the variant cell binding peptide substantially retains the ability to bind cells.

2. The cell binding peptide of claim 1, wherein the cell binding peptide comprises one or more modifications to the peptide N-terminus, peptide C-terminus, or within the peptide amino acid sequence, wherein the modification is selected from the group consisting of an aldehyde group, a hydroxyl group, a thiol group, an amino group, amino acids, a lysine, a cysteine, an acetyl group, polymers, synthetic polymers, polyethers, a poly(ethylene glycol) (PEG), an 11 unit polyethylene glycol (PEG10), a 1 unit polyethylene glycol (mini-PEG or MP), and combinations thereof.

3. An implantable device for tissue repair comprising a polymer having a covalently attached cell binding peptide, wherein the cell binding peptide comprises a sequence selected from the group consisting of SEQ ID NO: 16 and conservatively substituted variants of SEQ ID NO: 16 having at least 85% sequence identity to SEQ ID NO: 16, wherein the variant cell binding peptide substantially retains the ability to bind cells.

4. The implantable device of claim 3, wherein the cell binding peptide is attached to the polymer with or without a spacer.

5. The implantable device of claim 3, wherein the cell binding peptide binds to one or more of fibroblasts, endothelial cells, and stem cells.

6. The implantable device of claim 3, wherein the polymer is a biopolymer selected from the group consisting of a collagen, an injectable collagen, a keratin, a silk, a polysaccharide, an agarose, a dextran, a cellulose derivative, an oxidized cellulose, an oxidized regenerated cellulose, a carboxymethylcellulose, a hydroxypropylmethylcellulose, a chitosan, a chitin, a hyaluronic acid, derivatives thereof, and combinations thereof.

7. The implantable device of claim 3, wherein the implantable device comprising the polymer is selected from the group consisting of a gel, a hydrogel, an injectable material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft for breast reconstruction, a mesh for breast reconstruction, a composite surgical mesh comprising a synthetic polymer and a biopolymer, derivatives thereof, and combinations thereof.

8. A method for tissue repair comprising delivering to a subject an implantable device for tissue repair, wherein the implantable device comprises a polymer having a covalently attached cell binding peptide, wherein the cell binding peptide comprises a sequence selected from the group consisting of SEQ ID NO: 16 and conservatively substituted variants of SEQ ID NO: 16 having at least 85% sequence identity to SEQ ID NO: 16, wherein the variant cell binding peptide substantially retains the ability to bind cells, and wherein the implantable device serves as a scaffold for tissue repair.

9. The method of claim 8, wherein the cell binding peptide binds to one or more of fibroblasts, endothelial cells, and stem cells.

10. The method of claim 8, wherein the polymer is a biopolymer selected from the group consisting of a collagen, an injectable collagen, a keratin, a silk, a polysaccharide, an agarose, a dextran, a cellulose derivative, an oxidized cellulose, an oxidized regenerated cellulose, a carboxymethylcellulose, a hydroxypropylmethylcellulose, a chitosan, a chitin, a hyaluronic acid, derivatives thereof, and combinations thereof.

11. The method of claim 8, wherein the implantable device comprising the polymer is selected from the group consisting of a gel, a hydrogel, an injectable material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft for breast reconstruction, a mesh for breast reconstruction, a composite surgical mesh comprising a synthetic polymer and a biopolymer, derivatives thereof, and combinations thereof.

12. The method of claim 8, wherein the tissue for repair comprises any one or more of tendon, muscle, connective tissue, ligament, cardiac tissue, vascular tissue, and dermis.

13. A method for capturing cells onto an implantable device for tissue repair, comprising: contacting a sample comprising cells with the implantable device, wherein the implantable device comprises a polymer having a covalently attached cell binding peptide, wherein the cell binding peptide is selected from the group consisting of: SEQ ID NO: 16 and conservatively substituted variants of SEQ ID NO: 16 having at least 85% sequence identity to SEQ ID NO: 16, wherein the variant cell binding peptide substantially retains the ability to bind cells, and wherein the cells comprised in the sample are captured onto the implantable device through binding to the attached cell binding peptide.

14. The method of claim 13, wherein the cell binding peptide binds to one or more of fibroblasts, endothelial cells, and stem cells.

15. The method of claim 13, wherein the sample comprising cells comprises bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, a homogeneous population of cultured cells, a heterogeneous population of cultured cells, combinations thereof, and derivatives thereof.

16. The method of claim 13, wherein the polymer is a biopolymer selected from the group consisting of a collagen, an injectable collagen, a keratin, a silk, a polysaccharide, an agarose, a dextran, a cellulose derivative, an oxidized cellulose, an oxidized regenerated cellulose, a carboxymethylcellulose, a hydroxypropylmethylcellulose, a chitosan, a chitin, a hyaluronic acid, derivatives thereof, and combinations thereof.

17. The method of claim 13, wherein the implantable device comprising the polymer is selected from the group consisting of a gel, a hydrogel, an injectable material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft for breast reconstruction, a mesh for breast reconstruction, a composite surgical mesh comprising a synthetic polymer and a biopolymer, derivatives thereof, and combinations thereof.

18. A method for tissue repair, comprising:
   a. contacting a sample comprising cells with an implantable device comprising a polymer having a covalently attached cell binding peptide, wherein the cell binding peptide is selected from the group consisting of: SEQ ID NO: 16 and conservatively substituted variants of SEQ ID NO: 16 having at least 85% sequence identity to SEQ ID NO: 16, wherein the variant cell binding peptide substantially retains the ability to bind cells, wherein the cells comprised in the sample are captured onto the implantable device through binding to the attached cell binding peptide; and
   b. delivering to a subject the implantable device for tissue repair.

19. The method of claim 18, wherein the cells are one or more of fibroblasts, endothelial cells, and stem cells.

20. The method of claim 18, wherein the sample comprising cells comprises bone marrow, bone marrow, allogeneic stem cells, adipose tissue, stromal vascular fraction of adipose tissue, blood, blood products, platelets, platelet-rich plasma (PRP), umbilical cord blood, embryonic tissues, placenta, amniotic epithelial cells, tissue punch, omentum, a homogeneous population of cultured cells, a heterogeneous population of cultured cells, combinations thereof, and derivatives thereof.

21. The method of claim 18, wherein the polymer is a biopolymer selected from the group consisting of a collagen, an injectable collagen, a keratin, a silk, a polysaccharide, an agarose, a dextran, a cellulose derivative, an oxidized cellulose, an oxidized regenerated cellulose, a carboxymethylcellulose, a hydroxypropylmethylcellulose, a chitosan, a chitin, a hyaluronic acid, derivatives thereof, and combinations thereof.

22. The method of claim 18, wherein the implantable device comprising the polymer is selected from the group consisting of a gel, a hydrogel, an injectable material, an extracellular matrix, a decellularized tissue, a dermal matrix, an acellular human dermis, an acellular porcine dermis, an acellular bovine dermis, a porcine small intestinal submucosa (SIS), an acellular myocardium, a cardiac patch, a decellularized vascular conduit, a surgical mesh, a skin graft, a dural graft, a graft for foot ulcer repair, a hernia repair graft, a graft for abdominal repair, a tendon wrap, a tendon augmentation graft, a graft for rotator cuff repair, a graft for breast reconstruction, a mesh for breast reconstruction, a composite surgical mesh comprising a synthetic polymer and a biopolymer, derivatives thereof, and combinations thereof.

23. The method of claim 18, wherein the tissue for repair comprises any one or more of connective tissue, muscle, tendon, ligament, vascular tissue, cardiac tissue, and dermis.

24. A cell binding peptide comprising SEQ ID NO: 2.

* * * * *

SEQUENCE LISTING

```
<160> NUMBER OF SEQ ID NOS: 43

<210> SEQ ID NO 1
<211> LENGTH: 21
<212> TYPE: PRT
<213> ORGANISM: Artificial sequence
<220> FEATURE:
<223> OTHER INFORMATION: Synthetic

<400> SEQUENCE: 1

Ser Ser Met Tyr Phe Ser Pro Leu His Thr Trp Gln Ser Ala Pro Ser
1               5                   10                  15

Thr Ser Gly Ala Glu
```

-continued

20

<210> SEQ ID NO 2
<211> LENGTH: 21
<212> TYPE: PRT
<213> ORGANISM: Artificial sequence
<220> FEATURE:
<223> OTHER INFORMATION: Synthetic

<400> SEQUENCE: 2

Ser Ser Phe Arg Phe Gln Arg Leu Glu Asp Trp Asn Tyr Pro Ser Asn
1               5                   10                  15

Thr Asp Asn Ala Glu
            20

<210> SEQ ID NO 3
<211> LENGTH: 21
<212> TYPE: PRT
<213> ORGANISM: Artificial sequence
<220> FEATURE:
<223> OTHER INFORMATION: Synthetic

<400> SEQUENCE: 3

Ser Ser Gly Tyr Met Gln Phe Gly His Leu Leu Asp Trp Thr Gly Ser
1               5                   10                  15

Pro Ser Gly Ser Arg
            20

<210> SEQ ID NO 4
<211> LENGTH: 19
<212> TYPE: PRT
<213> ORGANISM: Artificial sequence
<220> FEATURE:
<223> OTHER INFORMATION: Synthetic

<400> SEQUENCE: 4

Ser Ser Phe Trp Asp Val Cys Gln Gly Asp Gly Thr Cys Tyr Gly Gly
1               5                   10                  15

Gly Ser Arg

<210> SEQ ID NO 5
<211> LENGTH: 15
<212> TYPE: PRT
<213> ORGANISM: Artificial sequence
<220> FEATURE:
<223> OTHER INFORMATION: Synthetic

<400> SEQUENCE: 5

Val Ala Asn Pro Phe Thr Tyr Leu Ser Ala Trp Ser Asn Pro Leu
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: Synthetic

<400> SEQUENCE: 6

Glu Thr Leu Ile Phe Ser Lys Leu Gly Gln Trp Gly Asn Ser Leu Ser
1               5                   10                  15

<210> SEQ ID NO 7
<211> LENGTH: 15
<212> TYPE: PRT

-continued

<213> ORGANISM: Artificial sequence
<220> FEATURE:
<223> OTHER INFORMATION: Synthetic

<400> SEQUENCE: 7

Gly Tyr Met Gln Phe Gly His Leu Leu Asp Trp Thr Gly Ser Pro
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Synthetic

<400> SEQUENCE: 8

Ser Val Tyr Arg Phe Asp Ser Leu Thr Thr Trp Ser Ser Asn Gln
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic

<400> SEQUENCE: 9

Gly Ser Trp Ser Phe Gly Thr Leu Gly Pro Trp Ser Ser Ser Gln
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic

<400> SEQUENCE: 10

Trp Leu Gly Asn Phe Asn Ala Leu Thr Asp Trp Pro Thr Asp Ser
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic

<400> SEQUENCE: 11

Thr Ser Gly Phe Phe Gly Ser Leu Asp Thr Trp Pro Pro Thr Leu
1               5                   10                  15

<210> SEQ ID NO 12
<211> LENGTH: 12
<212> TYPE: PRT
<213> ORGANISM: Artificial sequence
<220> FEATURE:
<223> OTHER INFORMATION: Synthetic

<400> SEQUENCE: 12

Asn Tyr Trp Asn Phe Gly Pro Leu Glu Asp Tyr Ser
1               5                   10

<210> SEQ ID NO 13
<211> LENGTH: 12
<212> TYPE: PRT
<213> ORGANISM: Artificial sequence

```
<220> FEATURE:
<223> OTHER INFORMATION: Synthetic

<400> SEQUENCE: 13

Ser Val Leu His Phe His Pro Met Lys Ser Tyr Asp
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic

<400> SEQUENCE: 14

Asn Ser Ile Tyr Phe Ser Pro Leu Arg Asp Tyr Gln
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetic

<400> SEQUENCE: 15

Gly His Phe Glu Tyr Gly Arg Leu Gln Ser Ile Leu
1               5                   10

<210> SEQ ID NO 16
<211> LENGTH: 20
<212> TYPE: PRT
<213> ORGANISM: Artificial sequence
<220> FEATURE:
<223> OTHER INFORMATION: Synthetic

<400> SEQUENCE: 16

Ser Ser Phe Arg Phe Gly Pro Leu Gly Thr Trp Asn Tyr Pro Ser Thr
1               5                   10                  15

Asp Asn Ala Glu
            20

<210> SEQ ID NO 17
<211> LENGTH: 14
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X=F, M, L, Y, W, or N
<220> FEATURE:
<221> NAME/KEY: MISC_FEATURE
<222> LOCATION: (2)..(2)
<223> OTHER INFORMATION: X= R, Q, P, I, Y or S
<220> FEATURE:
<221> NAME/KEY: MISC_FEATURE
<222> LOCATION: (4)..(4)
<223> OTHER INFORMATION: X= G, S, Q, T, or D
<220> FEATURE:
<221> NAME/KEY: MISC_FEATURE
<222> LOCATION: (5)..(5)
<223> OTHER INFORMATION: X= P, R, Y, K, H, or S
<220> FEATURE:
<221> NAME/KEY: MISC_FEATURE
<222> LOCATION: (7)..(7)
<223> OTHER INFORMATION: X= G, H, E, S, L, or T
<220> FEATURE:
<221> NAME/KEY: MISC_FEATURE
```

```
<222> LOCATION: (8)..(8)
<223> OTHER INFORMATION: X= T, D, A, Q, or P
<220> FEATURE:
<221> NAME/KEY: MISC_FEATURE
<222> LOCATION: (10)..(10)
<223> OTHER INFORMATION: X= N, Q, S, G, or T
<220> FEATURE:
<221> NAME/KEY: MISC_FEATURE
<222> LOCATION: (11)..(11)
<223> OTHER INFORMATION: X= Y, S, N, or G
<220> FEATURE:
<221> NAME/KEY: MISC_FEATURE
<222> LOCATION: (12)..(12)
<223> OTHER INFORMATION: X= P, A, S, or N
<220> FEATURE:
<221> NAME/KEY: MISC_FEATURE
<222> LOCATION: (13)..(13)
<223> OTHER INFORMATION: X= S, P, L, or Q
<220> FEATURE:
<221> NAME/KEY: MISC_FEATURE
<222> LOCATION: (13)..(13)
<223> OTHER INFORMATION: X= T, S, or N
<220> FEATURE:
<221> NAME/KEY: misc_feature
<222> LOCATION: (14)..(14)
<223> OTHER INFORMATION: Xaa can be any naturally occurring amino acid

<400> SEQUENCE: 17

Xaa Xaa Phe Xaa Xaa Leu Xaa Xaa Trp Xaa Xaa Xaa Xaa Xaa
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = F, W, L, Y, M, or I
<220> FEATURE:
<221> NAME/KEY: MISC_FEATURE
<222> LOCATION: (2)..(2)
<223> OTHER INFORMATION: X = N, Y, R, P, Q, I, F, or E
<220> FEATURE:
<221> NAME/KEY: MISC_FEATURE
<222> LOCATION: (3)..(3)
<223> OTHER INFORMATION: X = F or Y
<220> FEATURE:
<221> NAME/KEY: MISC_FEATURE
<222> LOCATION: (4)..(4)
<223> OTHER INFORMATION: X = G, S, T, Q, N, H, or D
<220> FEATURE:
<221> NAME/KEY: MISC_FEATURE
<222> LOCATION: (5)..(5)
<223> OTHER INFORMATION: X = P, R, Y, T, S, K, H, or A
<220> FEATURE:
<221> NAME/KEY: MISC_FEATURE
<222> LOCATION: (6)..(6)
<223> OTHER INFORMATION: X = L or M
<220> FEATURE:
<221> NAME/KEY: MISC_FEATURE
<222> LOCATION: (7)..(7)
<223> OTHER INFORMATION: X = T, G, E, S, R, Q, L, K, H, or D
<220> FEATURE:
<221> NAME/KEY: MISC_FEATURE
<222> LOCATION: (8)..(8)
<223> OTHER INFORMATION: X = D, T, S, Q, P, or A
<220> FEATURE:
<221> NAME/KEY: MISC_FEATURE
<222> LOCATION: (9)..(9)
<223> OTHER INFORMATION: X = W, Y, or I
<220> FEATURE:
<221> NAME/KEY: MISC_FEATURE
<222> LOCATION: (10)..(10)
<223> OTHER INFORMATION: X = P, N, Q, S, G, L, D, or T
```

```
<220> FEATURE:
<221> NAME/KEY: MISC_FEATURE
<222> LOCATION: (11)..(11)
<223> OTHER INFORMATION: X = Y, S, N, T, P, or G
<220> FEATURE:
<221> NAME/KEY: MISC_FEATURE
<222> LOCATION: (12)..(12)
<223> OTHER INFORMATION: X = P, A, S, T, D, or N
<220> FEATURE:
<221> NAME/KEY: MISC_FEATURE
<222> LOCATION: (13)..(13)
<223> OTHER INFORMATION: X = S, P, L, or Q
<220> FEATURE:
<221> NAME/KEY: MISC_FEATURE
<222> LOCATION: (14)..(14)
<223> OTHER INFORMATION: X = S or N

<400> SEQUENCE: 18

Xaa Xaa Xaa Xaa Xaa Xaa Xaa Xaa Xaa Xaa Xaa Xaa Xaa Xaa
1               5                   10

<210> SEQ ID NO 19
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = S, N, T, I, V, or G
<220> FEATURE:
<221> NAME/KEY: MISC_FEATURE
<222> LOCATION: (2)..(3)
<223> OTHER INFORMATION: X = F, W, or Y
<220> FEATURE:
<221> NAME/KEY: MISC_FEATURE
<222> LOCATION: (4)..(4)
<223> OTHER INFORMATION: X = D, E, W, N, Q, or G
<220> FEATURE:
<221> NAME/KEY: MISC_FEATURE
<222> LOCATION: (5)..(5)
<223> OTHER INFORMATION: X = V, M, or A
<220> FEATURE:
<221> NAME/KEY: MISC_FEATURE
<222> LOCATION: (7)..(7)
<223> OTHER INFORMATION: X = Q, P, E, L, H, R, or A
<220> FEATURE:
<221> NAME/KEY: MISC_FEATURE
<222> LOCATION: (8)..(8)
<223> OTHER INFORMATION: X = G, A, V, or R
<220> FEATURE:
<221> NAME/KEY: MISC_FEATURE
<222> LOCATION: (9)..(9)
<223> OTHER INFORMATION: X = D, N, or E
<220> FEATURE:
<221> NAME/KEY: MISC_FEATURE
<222> LOCATION: (13)..(13)
<223> OTHER INFORMATION: X = Y, W, or H

<400> SEQUENCE: 19

Xaa Xaa Xaa Xaa Xaa Cys Xaa Xaa Xaa Gly Thr Cys Xaa Gly Gly Gly
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = S, N, T, I, V, or G
<220> FEATURE:
```

-continued

<221> NAME/KEY: MISC_FEATURE
<222> LOCATION: (2)..(2)
<223> OTHER INFORMATION: X = F or Y
<220> FEATURE:
<221> NAME/KEY: MISC_FEATURE
<222> LOCATION: (4)..(4)
<223> OTHER INFORMATION: X = D, E, W, N, Q, or G
<220> FEATURE:
<221> NAME/KEY: MISC_FEATURE
<222> LOCATION: (5)..(5)
<223> OTHER INFORMATION: X = V, M, or A
<220> FEATURE:
<221> NAME/KEY: MISC_FEATURE
<222> LOCATION: (7)..(7)
<223> OTHER INFORMATION: X = Q, P, E, L, H, R, or A
<220> FEATURE:
<221> NAME/KEY: MISC_FEATURE
<222> LOCATION: (8)..(8)
<223> OTHER INFORMATION: X = G, A, V, or R
<220> FEATURE:
<221> NAME/KEY: MISC_FEATURE
<222> LOCATION: (9)..(9)
<223> OTHER INFORMATION: X = D, N, or E
<220> FEATURE:
<221> NAME/KEY: MISC_FEATURE
<222> LOCATION: (13)..(13)
<223> OTHER INFORMATION: X = Y, W, or H

<400> SEQUENCE: 20

```
Xaa Xaa Trp Xaa Xaa Cys Xaa Xaa Xaa Gly Thr Cys Xaa Gly Gly Gly
1               5                   10                  15
```

<210> SEQ ID NO 21
<211> LENGTH: 20
<212> TYPE: PRT
<213> ORGANISM: Artificial sequence
<220> FEATURE:
<223> OTHER INFORMATION: Synthetic

<400> SEQUENCE: 21

```
Ser Ser Gly Ser Asp Pro Ser Ser Ser Trp Phe Pro Pro Pro Val Trp
1               5                   10                  15

Phe Ser Ser Arg
            20
```

<210> SEQ ID NO 22
<211> LENGTH: 13
<212> TYPE: PRT
<213> ORGANISM: Artificial sequence
<220> FEATURE:
<223> OTHER INFORMATION: Synthetic

<400> SEQUENCE: 22

```
Ser Ser Leu Ala Ala Trp Tyr Ser Ser Trp Gly Val Ser
1               5                   10
```

<210> SEQ ID NO 23
<211> LENGTH: 20
<212> TYPE: PRT
<213> ORGANISM: Artificial sequence
<220> FEATURE:
<223> OTHER INFORMATION: Synthetic

<400> SEQUENCE: 23

```
Ser Glu Ala Thr Gln Ala Ser Arg Asn Trp Glu Gly Ile Arg Val Phe
1               5                   10                  15

Leu Ala Ser Arg
            20
```

-continued

```
<210> SEQ ID NO 24
<211> LENGTH: 13
<212> TYPE: PRT
<213> ORGANISM: Artificial sequence
<220> FEATURE:
<223> OTHER INFORMATION: Synthetic

<400> SEQUENCE: 24

Ser Glu Trp Asp Gln Tyr Tyr Ser Tyr Tyr Leu Glu His
1               5                   10

<210> SEQ ID NO 25
<211> LENGTH: 13
<212> TYPE: PRT
<213> ORGANISM: Artificial sequence
<220> FEATURE:
<223> OTHER INFORMATION: Synthetic

<400> SEQUENCE: 25

Ser Pro Trp Val Thr Trp Tyr Tyr Ser Ala Ser Ser Pro
1               5                   10

<210> SEQ ID NO 26
<211> LENGTH: 16
<212> TYPE: PRT
<213> ORGANISM: Artificial sequence
<220> FEATURE:
<223> OTHER INFORMATION: Synthetic

<400> SEQUENCE: 26

Ser Thr Met Leu Ser Trp Asp His Val Asn Leu Tyr Tyr Thr Met His
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: Synthetic

<400> SEQUENCE: 27

Ser Pro Leu Leu His Trp Asn Lys Ile Gln Asp Tyr Tyr Arg Leu Asn
1               5                   10                  15

<210> SEQ ID NO 28
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: X = S, T, G, or P
<220> FEATURE:
<221> NAME/KEY: MISC_FEATURE
<222> LOCATION: (3)..(3)
<223> OTHER INFORMATION: X = Y, W, or F
<220> FEATURE:
<221> NAME/KEY: MISC_FEATURE
<222> LOCATION: (4)..(4)
<223> OTHER INFORMATION: X = A, V, I, or L
<220> FEATURE:
<221> NAME/KEY: MISC_FEATURE
<222> LOCATION: (5)..(5)
<223> OTHER INFORMATION: X = S, T, G, or P
<220> FEATURE:
<221> NAME/KEY: MISC_FEATURE
<222> LOCATION: (6)..(8)
<223> OTHER INFORMATION: X = Y, W, or F
<220> FEATURE:
```

```
<221> NAME/KEY: MISC_FEATURE
<222> LOCATION: (9)..(9)
<223> OTHER INFORMATION: X = S, T, G, or P
<220> FEATURE:
<221> NAME/KEY: MISC_FEATURE
<222> LOCATION: (10)..(10)
<223> OTHER INFORMATION: X = A, V, I, or L
<220> FEATURE:
<221> NAME/KEY: MISC_FEATURE
<222> LOCATION: (11)..(13)
<223> OTHER INFORMATION: X =S, T, G, or P

<400> SEQUENCE: 28

Xaa Xaa Xaa Xaa Xaa Xaa Xaa Xaa Xaa Xaa Xaa Xaa Xaa
1               5                   10

<210> SEQ ID NO 29
<211> LENGTH: 15
<212> TYPE: PRT
<213> ORGANISM: Artificial sequence
<220> FEATURE:
<223> OTHER INFORMATION: Synthetic

<400> SEQUENCE: 29

Asp Asp Ser Pro Trp Val Thr Trp Tyr Tyr Ser Ala Ser Ser Pro
1               5                   10                  15

<210> SEQ ID NO 30
<211> LENGTH: 17
<212> TYPE: PRT
<213> ORGANISM: Artificial sequence
<220> FEATURE:
<223> OTHER INFORMATION: Synthetic

<400> SEQUENCE: 30

Asp Asp Asp Asp Ser Pro Trp Val Thr Trp Tyr Tyr Ser Ala Ser Ser
1               5                   10                  15

Pro

<210> SEQ ID NO 31
<211> LENGTH: 17
<212> TYPE: PRT
<213> ORGANISM: Artificial sequence
<220> FEATURE:
<223> OTHER INFORMATION: Synthetic

<400> SEQUENCE: 31

Asp Glu Asp Glu Ser Pro Trp Val Thr Trp Tyr Tyr Ser Ala Ser Ser
1               5                   10                  15

Pro

<210> SEQ ID NO 32
<211> LENGTH: 19
<212> TYPE: PRT
<213> ORGANISM: Artificial sequence
<220> FEATURE:
<223> OTHER INFORMATION: Synthetic

<400> SEQUENCE: 32

Asp Glu Asp Glu Asp Glu Ser Pro Trp Val Thr Trp Tyr Tyr Ser Ala
1               5                   10                  15

Ser Ser Pro

<210> SEQ ID NO 33
<211> LENGTH: 9
<212> TYPE: PRT
```

<213> ORGANISM: Artificial sequence
<220> FEATURE:
<223> OTHER INFORMATION: Synthetic

<400> SEQUENCE: 33

Ser Pro Trp Val Thr Trp Tyr Tyr Ser
1               5

<210> SEQ ID NO 34
<211> LENGTH: 11
<212> TYPE: PRT
<213> ORGANISM: Artificial sequence
<220> FEATURE:
<223> OTHER INFORMATION: Synthetic

<400> SEQUENCE: 34

Trp Val Thr Trp Tyr Tyr Ser Ala Ser Ser Pro
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic

<400> SEQUENCE: 35

Thr Trp Tyr Tyr Ser Ala Ser Ser Pro
1               5

<210> SEQ ID NO 36
<211> LENGTH: 11
<212> TYPE: PRT
<213> ORGANISM: Artificial sequence
<220> FEATURE:
<223> OTHER INFORMATION: Synthetic

<400> SEQUENCE: 36

Ser Pro Trp Val Thr Trp Tyr Tyr Ser Ala Ser
1               5                   10

<210> SEQ ID NO 37
<211> LENGTH: 7
<212> TYPE: PRT
<213> ORGANISM: Artificial sequence
<220> FEATURE:
<223> OTHER INFORMATION: Synthetic

<400> SEQUENCE: 37

Ser Pro Trp Val Thr Trp Tyr
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: X = S, T, G, or P
<220> FEATURE:
<221> NAME/KEY: MISC_FEATURE
<222> LOCATION: (1)..(1)
<223> OTHER INFORMATION: X is modified with a Tag1 which is 0-6 residues
      of either D and/or E but the polypeptide can only have a Tag1 or a
      Tag2 not both
<220> FEATURE:

```
<221> NAME/KEY: MISC_FEATURE
<222> LOCATION: (3)..(3)
<223> OTHER INFORMATION: X = Y, W, or F
<220> FEATURE:
<221> NAME/KEY: MISC_FEATURE
<222> LOCATION: (4)..(4)
<223> OTHER INFORMATION: X = A, V, I, or L
<220> FEATURE:
<221> NAME/KEY: MISC_FEATURE
<222> LOCATION: (5)..(5)
<223> OTHER INFORMATION: X = S, T, G, or P
<220> FEATURE:
<221> NAME/KEY: MISC_FEATURE
<222> LOCATION: (6)..(8)
<223> OTHER INFORMATION: X = Y, W, or F
<220> FEATURE:
<221> NAME/KEY: MISC_FEATURE
<222> LOCATION: (9)..(9)
<223> OTHER INFORMATION: X is modified with a Tag2 which is 0-6 residues
      of either D and/or E but the polypeptide can only have a Tag1 or a
      Tag2 not both
<220> FEATURE:
<221> NAME/KEY: MISC_FEATURE
<222> LOCATION: (9)..(9)
<223> OTHER INFORMATION: X = S, T, G, or P

<400> SEQUENCE: 38

Xaa Xaa Xaa Xaa Xaa Xaa Xaa Xaa Xaa
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: X = S, T, G, or P
<220> FEATURE:
<221> NAME/KEY: MISC_FEATURE
<222> LOCATION: (1)..(1)
<223> OTHER INFORMATION: X is modified with Tag1 which is 0-6 residues
      of D and/or E
<220> FEATURE:
<221> NAME/KEY: MISC_FEATURE
<222> LOCATION: (3)..(3)
<223> OTHER INFORMATION: X = Y, W, or F
<220> FEATURE:
<221> NAME/KEY: MISC_FEATURE
<222> LOCATION: (4)..(4)
<223> OTHER INFORMATION: X = A, V, I, or L
<220> FEATURE:
<221> NAME/KEY: MISC_FEATURE
<222> LOCATION: (5)..(5)
<223> OTHER INFORMATION: X = S, T, G, or P
<220> FEATURE:
<221> NAME/KEY: MISC_FEATURE
<222> LOCATION: (6)..(8)
<223> OTHER INFORMATION: X = Y, W, or F
<220> FEATURE:
<221> NAME/KEY: MISC_FEATURE
<222> LOCATION: (9)..(9)
<223> OTHER INFORMATION: X = S, T, G, or P

<400> SEQUENCE: 39

Xaa Xaa Xaa Xaa Xaa Xaa Xaa Xaa Xaa
1               5

<210> SEQ ID NO 40
<211> LENGTH: 21
<212> TYPE: PRT
<213> ORGANISM: Artificial sequence
<220> FEATURE:
```

```
<223> OTHER INFORMATION: Synthetic

<400> SEQUENCE: 40

Ser Ser Gly Pro Arg Glu Ile Trp Asp Ser Leu Val Gly Val Val Asn
1               5                   10                  15

Pro Gly Trp Ser Arg
            20

<210> SEQ ID NO 41
<211> LENGTH: 21
<212> TYPE: PRT
<213> ORGANISM: Artificial sequence
<220> FEATURE:
<223> OTHER INFORMATION: Synthetic

<400> SEQUENCE: 41

Ser Ser Gly Gly Val Gly Gly Trp Ala Leu Phe Glu Thr Leu Arg Gly
1               5                   10                  15

Lys Glu Val Ser Arg
            20

<210> SEQ ID NO 42
<211> LENGTH: 21
<212> TYPE: PRT
<213> ORGANISM: Artificial sequence
<220> FEATURE:
<223> OTHER INFORMATION: Synthetic

<400> SEQUENCE: 42

Ser Ser Val Ala Glu Trp Ala Leu Arg Ser Trp Glu Gly Met Arg Val
1               5                   10                  15

Gly Glu Ala Ser Arg
            20

<210> SEQ ID NO 43
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: X = any amino acid
<220> FEATURE:
<221> NAME/KEY: MISC_FEATURE
<222> LOCATION: (6)..(6)
<223> OTHER INFORMATION: X = S or T
<220> FEATURE:
<221> NAME/KEY: MISC_FEATURE
<222> LOCATION: (8)..(8)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid
<220> FEATURE:
<221> NAME/KEY: MISC_FEATURE
<222> LOCATION: (12)..(12)
<223> OTHER INFORMATION: X = any amino acid

<400> SEQUENCE: 43

Trp Xaa Xaa Phe Glu Xaa Leu Xaa Gly Xaa Glu Xaa
1               5                   10
```